(12) United States Patent
Genieser et al.

(10) Patent No.: US 11,001,605 B2
(45) Date of Patent: May 11, 2021

(54) CYCLIC DINUCLEOTIDES CONTAINING BENZIMIDAZOLE, METHOD FOR THE PRODUCTION OF SAME, AND USE OF SAME TO ACTIVATE STIMULATOR OF INTERFERON GENES (STING)-DEPENDENT SIGNALING PATHWAYS

(71) Applicant: BIOLOG LIFE SCIENCE INSTITUTE GmbH & Co. KG, Bremen (DE)

(72) Inventors: Hans-Gottfried Genieser, Lemwerder (DE); Frank Schwede, Bremen (DE); Andreas Rentsch, Bremen (DE)

(73) Assignee: BIOLOG LIFE SCIENCE INSTITUTE GMBH & CO. KG, Bremen (DE)

( * ) Notice: Subject to any disclaimer, the term of this patent is extended or adjusted under 35 U.S.C. 154(b) by 0 days.

(21) Appl. No.: 16/339,938

(22) PCT Filed: Oct. 2, 2017

(86) PCT No.: PCT/EP2017/074966
§ 371 (c)(1),
(2) Date: Apr. 5, 2019

(87) PCT Pub. No.: WO2018/065360
PCT Pub. Date: Apr. 12, 2018

(65) Prior Publication Data
US 2020/0040028 A1    Feb. 6, 2020

(30) Foreign Application Priority Data
Oct. 7, 2016   (DE) .................... 10 2016 219 566.2

(51) Int. Cl.
*C07H 21/00*    (2006.01)
*C12P 19/40*    (2006.01)

(52) U.S. Cl.
CPC .............. *C07H 21/00* (2013.01); *C12P 19/40* (2013.01)

(58) Field of Classification Search
CPC ...................................... C07H 21/00
See application file for complete search history.

(56) References Cited

U.S. PATENT DOCUMENTS 4,482,708 A * 11/1984 Nguyen ............... C07H 19/052
435/70.5

FOREIGN PATENT DOCUMENTS

| WO | 2014179335 A1 | 11/2014 |
|---|---|---|
| WO | 2015077354 A1 | 5/2015 |
| WO | 2016096174 A1 | 6/2016 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Krenitsky et al., Biochemistry, 1981, 20, p. 3615-3621. (Year: 1981).*
Clivio et al., Chemical Reviews, 2013, 113, p. 7354-7401. (Year: 2013).*
International Search Report and Written Opinion dated Dec. 1, 2017 for corresponding PCT Application No. PCT/EP2017/074966.

* cited by examiner

*Primary Examiner* — Jonathan S Lau
(74) *Attorney, Agent, or Firm* — Polsinelli PC

(57) ABSTRACT

Cyclic dinucleotides are described, which in contrast to their natural congeners carry lipophilic nucleobases and have higher membrane permeability and increased biological activity.

17 Claims, 1 Drawing Sheet

CYCLIC DINUCLEOTIDES CONTAINING BENZIMIDAZOLE, METHOD FOR THE PRODUCTION OF SAME, AND USE OF SAME TO ACTIVATE STIMULATOR OF INTERFERON GENES (STING)-DEPENDENT SIGNALING PATHWAYS

CROSS-REFERENCE TO RELATED APPLICATIONS

This application is a national stage application (under 35 U.S.C. § 371) of PCT/EP2017/074966, filed Oct. 2, 2017, which claims benefit of priority of German Application No. 10 2016 219 566.2, filed Oct. 7, 2016, which are incorporated herein by reference in their entireties.

FIELD OF THE INVENTION

New cyclic dinucleotides with lipophilic nucleobases are described, which, in contrast to their natural congeners, have increased cell membrane permeability and higher activation potential.

The present invention has its focus on immunotherapy and consists of cyclic dinucleotides (CDNs) of the general Formula (I), as defined in the claims section of this document. In more detail, the invention described here concerns benzimidazole-containing CDNs, their pharmacologically suitable salt forms and their corresponding prodrugs, capable of the induction of the production of type 1 interferons in human and animal cells. In addition, the inventive CDNs can be used as reagents in signal transduction research and as modulators for CDN binding proteins and their isoforms. Further on, the inventive CDNs can be used as ligands for affinity chromatography, for the production of antibodies and for diagnostic applications.

BACKGROUND OF THE INVENTION

Immunotherapy is a rapidly expanding medical research field, wherein the immune system of a patient is activated, deactivated or otherwise modulated, in order to achieve a therapeutic benefit. Immunotherapeutic concepts include cells, antigens, antibodies, nucleic acids, peptides, proteins, naturally present ligands or synthetic molecules. Cytokines are small glycoproteins, which modulate the immune response via complex signalling cascades. However, for multiple reasons a direct therapeutic application of cytokines is rather limited, among others, due to their short half-life in the blood, which would lead to rather short therapeutic intervals and to high doses in cytokines.

SUMMARY OF THE INVENTION

Therefore, a more promising approach in immunotherapy is the therapeutic induction of cytokines, wherein a patient is treated with an immunomodulatory compound, which stimulates one or more therapeutically beneficial cytokine(s) in the body.

The STING protein is a transmembrane receptor protein and plays a central role in the physiological production of cytokines in the innate immune system. Activation of STING leads to the production of type 1 interferons (e.g. IFN-α and IFN-β) via the interferon regulatory factor 3 (IRF3) signalling pathway and to pre-inflammatory cytokines (IL-1α, IL-1β, TNF-α, etc.) via the nuclear factor kappa-light-chain-enhancer of activated B cells (NF-κB) signalling pathway.

At present, it is known that the human STING protein is activated by binding of 3 different categories of CDNs.
1. Exogenous 3',3-CDNs (c-diGMP, c-diAMP, 3',3'-cGAMP) from bacteria and archaea.
2. Endogenously formed 2',3'-cGAMP.
3. Synthetic CDNs, which represent chemical analogues of the natural CDNs listed above under 1. and 2.

Presently, the STING protein is explored as a promising drug target for numerous medical indications such as cancer, vaccine adjuvants and infectious diseases, and CDNs are lead structures for the development of corresponding therapeutic agents.

Some examples for CDNs as STING activators are described in US/2014/0329889, WO/2014/189805, WO/2014/093936, WO/2015/077354, WO/2015/185565, WO/2016/096174, WO/2016/096577 and WO/2016/145102. However, up to now only a limited series of analogue structures was synthesised and biologically tested and no detailed molecular interaction analyses are disclosed in reports published.

In addition, only CDNs with the nucleobases adenine, guanine, hypoxanthine and isoguanine were tested and described. These nucleobases are considerably polar heterocycles, which indeed favour water solubility, but on the other hand negatively affect membrane permeability. The poor membrane permeability of the CDNs known so far is, however, a limiting factor and a serious disadvantage for a potential therapeutic application.

Thus, the prominent task in connection with the present invention was the provision of improved CDNs in terms of increased membrane permeability and/or better biological activity.

With the present invention, this task is solved by the provision of new lipophilic benzimidazole-containing CDNs of the general Formula (I), as defined in the claims section. In this context, it can be shown in particular, that the exchange of at least one of the natural purine-based nucleobases adenine, guanine, hypoxanthine or isoguanine with a benzimidazole unit or with a substituted benzimidazole, leads to synthetic CDNs with substantially improved and so far unknown lipophilicity properties. Surprisingly, the CDNs described in this invention, with at least one benzimidazole unit show good STING-initiated interferon production, notwithstanding of the exchange of at least one purine-based nucleobase.

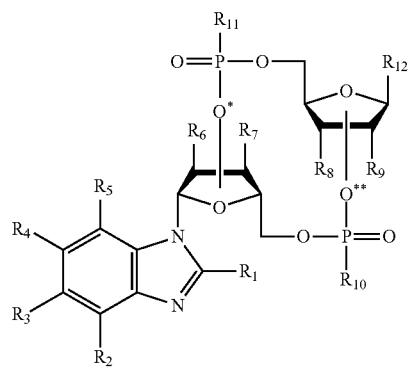

Formula (I)

Chemical Definitions and Termini Used

In the following, the chemical definitions and chemical termini used throughout the present invention to specify the new chemical entities of the present invention are listed and described in detail. They are valid for the whole description of the invention.

"Variably connectable structural unit" and "variably connectable structural units":

Whenever a chemical structure is shown or described, wherein a ring system contains side chains or substituents, which are designated as "variably connectable structural unit" or "variably connectable structural units", as shown in the following exemplary formula:

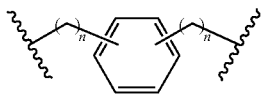

this structural unit or these structural units can replace any of the hydrogen atoms, connected to the ring system.

The entirety of replaceable hydrogen atoms comprises all hydrogen atoms, regardless whether these are explicitly depicted or implied by the structure shown or by the description.

All variants of substitutions resulting from this definition are in included by the terms "variably connectable structural unit" and "variably connectable structural units", provided that they describe chemically stable compounds or provided that no limitations are mentioned within this document.

For the above formula the described definitions result in three specific structures, shown in the formula hereinafter:

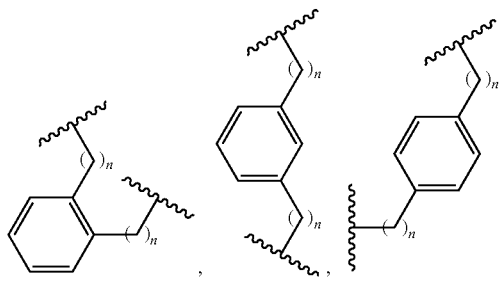

With respect to the cyclic ribose system and deviant from the previous definition, variably connectable structural unit(s) can only substitute the residue R at positions, commonly designated as position 2' and position 3'.

Deviant as well from the previous definition, the residues R in 2'-position and 3'-position of the ribose system are not limited to hydrogen atoms, but can be specified as described for $R_6$-$R_9$.

In the following Formula:

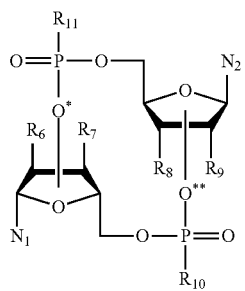

with the variably connectable structural unit(s) * and **, the substitution of $R_6$ or $R_7$ and $R_8$ or $R_9$, respectively, leads to the following specific structures:

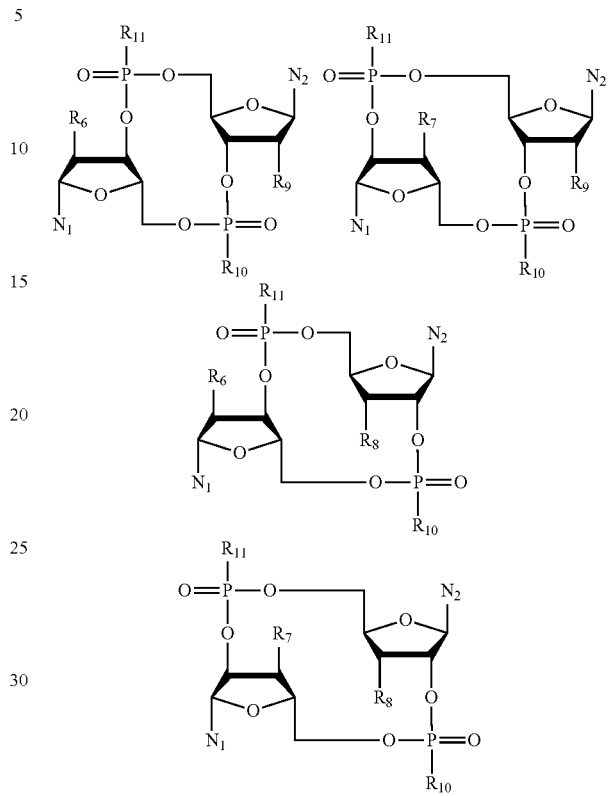

These specific structures shown above represent the inventive CDNs with the specific connections c[$N_1$(3',5')p$N_2$(3',5')p], c[$N_1$(2',5')p$N_2$(3',5')p], c[$N_1$(3',5')p$N_2$(2',5')p], c[$N_1$(2',5')p$N_2$(2',5')p], wherein $N_1$ and $N_2$ are the corresponding nucleobases, following the definition that $N_1$ is a benzimidazole unit of the structure

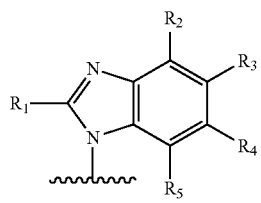

and that $N_2$=$R_{12}$, and $N_2$ can be equal or unequal to $N_1$.

In case of any doubt, the residues $R_1$, $R_2$, $R_3$, $R_4$, $R_5$, $R_6$, $R_7$, $R_8$, $R_9$, $R_{10}$ and $R_{11}$ are defined in claim 1.

In the natural occurring CDNs both, $R_{10}$ and $R_{11}$, are oxygen and the double bond to phosphate is delocalised between both exocyclic oxygen atoms. In aqueous solution at physiological pH natural CDNs carry two negative charges, due to their two phosphate units each with a single negative charge.

Each negative charge is delocalised between the two exocyclic oxygen atoms of the respective phosphate units and has corresponding counter cations, such as for example $Na^+$ or $K^+$.

In the present invention all phosphate structures are shown as free acid forms with localised double bond between oxygen and phosphorus. Indeed the localisation of the above mentioned double bond will be determined by the nature of the residues $R_{10}$ and $R_{11}$.

Thus, the structural formulas shown in this document do not mirror the exact distribution of electrons and charges at the phosphate moieties but only serve for clarity.

If $R_{10}$ and $R_{11}$ are not oxygen the phosphorus atom has four different ligands and is hence chiral. For discrimination of the resulting two stereoisomeric forms, the Rp-/Sp nomenclature according to Cahn-Ingold-Prelog is used throughout this document; while "p" indicates that the rules refer to phosphorus as the chiral centre. The inventive compounds include structures wherein both, $R_{10}$ and $R_{11}$, can be sulphur or a borano ($BH_3$) group, resulting in phosphorothioates and boranophosphates, respectively.

As a consequence, the inventive compounds can contain either one or two phosphorothioate units, one or two boranophosphate units or one phosphorothioate and one boranophosphate unit.

Due to the phosphorus-induced chirality, an exemplary CDN of the invention containing two phosphorothioate units with the general formula $c[N_1(2',5')pS-N_2(3',5')pS]$ comprises four different stereoisomers which can be specified as follows: $c[N_1(2',5')pS[Rp]—N_2(3',5')pS[Sp]]$, $c[N_1(2',5')pS[Rp]-N_2(3',5')pS[Rp]]$, $c[N_1(2',5')pS[Sp]-N_2(3',5')pS[Rp]]$ and $c[N_1(2',5')pS[Sp]-N_2(3',5')pS[Sp]]$, wherein $N_1$ and $N_2$ represent the two nucleobases, which can be different or identical ($N_1 \neq N_2$ or $N_1 = N_2$). In case of a stated general abbreviation $c[N_1(2',5')pS-N_2(3',5')pS]$, this definition refers to all 4 stereoisomeric forms thereof.

Analogously, in case of CDNs of the invention containing two boranophosphate units of the exemplary general formula $c[N_1(2',5')pB-N_2(3',5')pB]$, the following four specific stereoisomers are included: $c[N_1(2',5')pB[Rp]-N_2(3',5')pB[Sp]]$, $c[N_1(2',5')pB[Rp]-N_2(3',5)pB[Rp]]$, $d[N_1(2',5')pB[Sp]-N_2(3',5')pB[Rp]]$ and $c[N_1(2',5')pB[Sp]-N_2(3',5')pB[Sp]]$, wherein $N_1$ and $N_2$ represent the two nucleobases, which can be different or identical ($N_1 \neq N_2$ or $N_1 = N_2$).

In case the compounds of the invention contain one phosphorothioate unit and one boranophosphate unit exemplary described by the general term "$c[N_1(3',5')pB-N_2(2',5')pS]$" analogously the following four stereoisomeric forms are included: $c[N_1(3',5')pB[Rp]-N_2(2',5')pS[Sp]]$-$c[N_1(3',5')pB[Rp]-N_2(2',5')pS[Rp]]$, $c[N_1(3',5')pB[Sp]-N_2(2',5')pS[Rp]]$, $c[N_1(3',5')pB[Sp]-N_2(2',5')pS[Sp]]$, wherein $N_1$ and $N_2$ represent the two nucleobases, which can be different or identical ($N_1 \neq N_2$ or $N_1 = N_2$).

In case the inventive compounds contain only one phosphorothioate unit exemplary described by the general term "$c[N_1(2',5')pS-N_2(3',5')p]$", only the two following stereoisomeric forms are included: $c[N_1(2',5')pS[Rp]-N_2(3',5')p]$, $c[N_1(2',5')pS[Sp]-N_2(3',5')p]$, wherein $N_1$ and $N_2$ represent the two nucleobases, which can be different or identical ($N_1 \neq N_2$ or $N_1 = N_2$).

Analogously, in case the inventive compounds contain only one boranophosphate unit exemplary described by the general term "$c[N_1(2',5')pB-N_2(3',5')p]$", only the two following stereoisomeric forms are included: $c[N_1(2',5')pB[Rp]-N_2(3',5')p]$, $c[N_1(2',5')pB[Sp]-N_2(3',5')p]$, wherein $N_1$ and $N_2$ represent the two nucleobases, which can be different or identical ($N_1 \neq N_2$ or $N_1 = N_2$).

A person skilled in the art knows, that only physiological acceptable salt forms of the inventive CDNs will be used, especially if they are intended for medical applications.

The documents WO 2017/027645 A1 and WO 2017/027646 A1 describe cyclic dinucleotides as well. However, they were published only after the priority date of this application and do not disclose the generic formulas or corresponding single compounds of the present invention In the following, the terms are defined, which are used for the description of the present invention. These definitions are valid for the entire description of this invention.

Halogen means F, Cl, Br, and I.

Alkyl is an alkyl group, represented by a hydrocarbon chain with 1 to 28 carbon atoms, preferably 1 carbon atoms, with or without (integrated) hetero atoms, preferably, but not limited to, O, S, Si, N, Se, B, while the connection with the general structure according to Formula (I), if not defined differently, is made via carbon.

An alkyl group within this document can be linearly saturated and is preferably methyl, ethyl, propyl, butyl or pentyl, however, without being limited to it, or can be linearly unsaturated and comprises preferably 2 to 20 carbon atoms and is further preferably ethylene, propylene, butylene and pentylene, however, without being limited to it, or can be saturated and branched and then contains at least three carbon atoms and is preferably, isopropyl, sec. butyl or tert.-butyl, however, without being limited to it, or can be unsaturated and branched and then contains at least three carbon atoms and is preferably isopropenyl, isobutenyl, isopentenyl or 4-methyl-3-pentenyl, however, without being limited to it, or can be cyclic and saturated and then contains preferably 3-8 ring atoms and is preferably, cyclopentyl, cyclohexyl, cycloheptyl, piperidino or piperazino, however, without being limited to it, or can be unsaturated and cyclic and then contains preferably 3-8 ring atoms.

Within this document the term "saturated" means a hydrocarbon, which has neither C—C double bonds nor C—C triple bonds.

In the case of substituted and saturated alkyl groups, however, one or more multiple bonds between carbon and oxygen, carbon and sulphur or carbon and nitrogen can be present, which can be involved in a keto-enol or an imine-enamine tautomerism.

An alkyl group as it is named throughout this document can be unsubstituted or further substituted.

Potential substituents comprise one or more (unsubstituted) alkyl groups, halogen-substituted alkyl groups, halogen atoms, substituted and unsubstituted aryl groups, substituted and unsubstituted heteroaryl groups, amino-, oxo-, nitro-, cyano-, azido-, hydroxy-, mercapto-, keto-, carboxy-, carbamoyl-, epoxy-, methoxy-, methylthio or ethynyl groups, however, without being limited to it.

If alkyl, as defined above, contains a polyethylene glycol chain (PEG), the preferred number of carbon atoms can increase by the number of PEG carbon atoms, while the PEG chain preferably contains 1 to 500 ethylene glycol groups ($—(CH_2CH_2O)_n—$ with n=1 to 500).

In this case, $-(EO)_n—$ can be used as abbreviation for $—(CH_2CH_2O)_n—$, while the number of PEG units can either be as indicated in the given example or be in the range of 1-500.

Aralkyl describes an alkyl group, as defined above, which is connected to an unsubstituted or substituted, aromatic or heteroaromatic hydrocarbon, which consists of one or more aromatic ring systems, each with 3-8 ring atoms.

Substituents for the alkyl as well as for the aryl part consist of one or more halogen atoms, alkyl or halogenalkyl groups, substituted or unsubstituted aryl groups, substituted or unsubstituted heteroaryl groups, amino, nitro, cyano, azido, hydroxy, mercapto, carboxy, methoxy, methylthio groups, however, without being limited to it.

Aryl describes an unsubstituted or substituted, aromatic or heteroaromatic hydrocarbon, which consists of one or more aromatic ring systems, each with 3-8 ring atoms. Substituents consist of, but are not limited to, one or more halogen atoms, alkyl or halogenalkyl groups, substituted or unsubstituted aryl groups, substituted or unsubstituted heteroaryl groups, amino, nitro, cyano, azido, hydroxy, mercapto, carboxy, methoxy, methylthio groups, however, without being limited to it.

Acyl describes a —C(O)-alkyl group, wherein the specification of the alkyl group has been defined above.

Aracyl describes a —C(O)-aryl group, wherein the specification of the aryl group has been defined above.

Carbamoyl describes a —C(O)—NH2 group, wherein both hydrogen atoms independently from each other can be substituted by alkyl, aryl or aralkyl groups and wherein the specifications of the alkyl, aryl and aralkyl groups have been defined above.

O-Acyl describes a —O—C(O)-alkyl group, wherein the specification of the acyl group has been defined above.

O-Alkyl describes an alkyl group, which is connected via oxygen, wherein the specification of the alkyl group has been defined above.

O-Aracyl describes a —OC(O)-aryl group, wherein the specification of the aryl group has been defined above.

O-Aralkyl describes an aralkyl group, which is connected via oxygen, wherein the specification of the aralkyl group has been defined above.

O-Aryl describes an aryl group, which is connected via oxygen, wherein the specification of the aryl group has been defined above.

O-Carbamoyl describes a carbamoyl group, which is connected via oxygen, wherein the specification of the carbamoyl group has been defined above.

S-Alkyl describes an alkyl group, which is connected via sulphur, wherein the specification of the alkyl group has been defined above.

S-Aryl describes an alkyl group, which is connected via sulphur, wherein the specification of the aryl group has been defined above.

S-Aralkyl describes an aralkyl group, which is connected via sulphur, wherein the specification of the aralkyl group has been defined above.

NH-Alkyl and N-Bisalkyl describe one and two alkyl groups, respectively, which are connected via nitrogen, wherein the specification of an alkyl group has been defined above.

NH-Aryl and N-Bisaryl describe one and two aryl groups, respectively, which are connected via nitrogen, wherein the specification of an aryl group has been defined above.

NH-Carbamoyl describes a carbamoyl group, which is connected via nitrogen, wherein the specification of the carbamoyl group has been defined above.

Amido-alkyl describes an alkyl group, which is connected via a NH—C(O)— bond, wherein the specification of the alkyl group has been defined above.

Amido-aryl describes an aryl group, which is connected via a NH—C(O)— bond, wherein the specification of the aryl group has been defined above.

Amido-aralkyl describes an aralkyl group, which is connected via a NH—C(O)— bond, wherein the specification of the aralkyl group has been defined above.

DEFINITION OF FORMULAS, FIGURES AND TABLES

Figure 1:
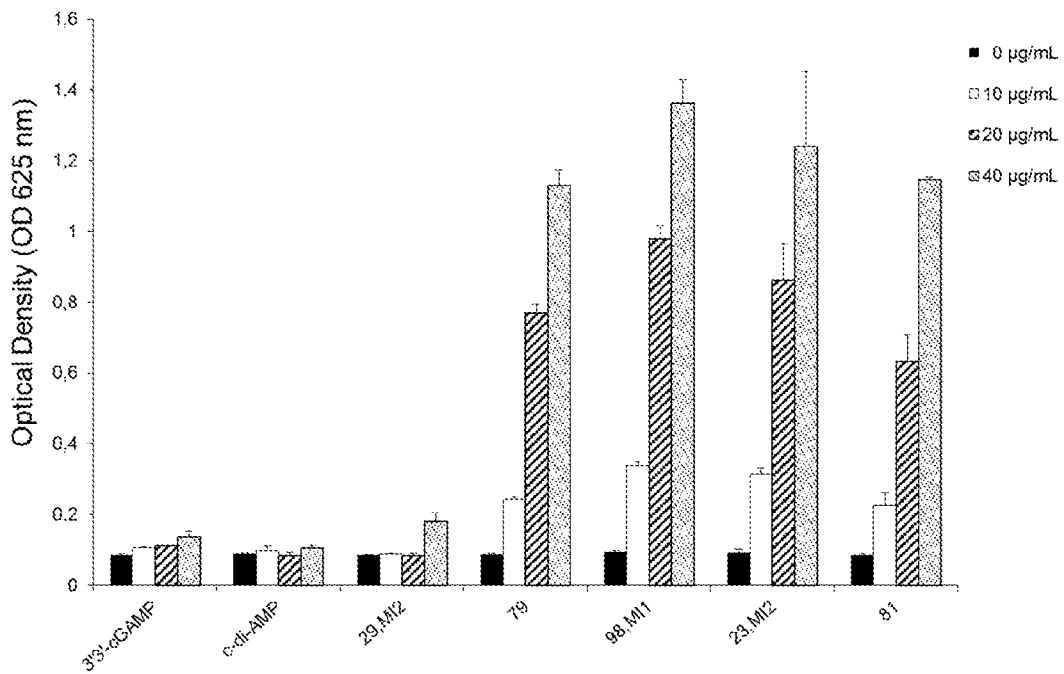
FIG. 1 is a graph depicting optical density as compared to various compounds according to aspects of the invention.

Formula (I): General depiction of the constitution of the new, inventive compounds (compare claim 1).

Synthesis 1: Synthesis of Cyclic (adenosine-(3'→5')-monophosphate-benzimidazole riboside-(3'→5')-monophosphate) (c[A(3',5')p-BI(3',5')p]).

Legend for Synthesis 1: Synthetic steps: a) pyridinium trifluoroacetate/$H_2O$; b) tert.-butylamine; c) dichloroacetic acid/$H_2O$; d) A, pyridine; e) tert-butylhydroperoxide; f) dichloroacetic acid/$H_2O$; g) 2-chloro-5,5-dimethyl-1,3,2-dioxaphosphorinane-2-oxide; h) iodine, $H_2O$; I) methylamine/ethanol; j) triethylamine trihydrofluoride.

Synthesis 2: Synthesis of Cyclic (5,6-dichlorobenzimidazole riboside-(3'→5')-monophosphorothioate-5,6-dichlorobenzimidazole riboside-monophosphorothioate) (c[DCIBI(3',5')pS-DCIBI(3',5')pS]).

Legend for Synthesis 2: Synthetic steps: a) pyridinium trifluoroacetate/$H_2O$; b) tert.-butylamine; c) dichloroacetic acid/$H_2O$; d) A, pyridine; e) 3-((N,N-dimethylaminomethylidene)amino)-3H-1,2,4-dithiazole-5-thione (DDTT); f) dichloro acetic acid/$H_2O$; g) 2-chloro-5,5-dimethyl-1,3,2-dioxaphosphorinane-2-oxide; h) 3-H-1,2-benzodithiol-3-one; I) methylamine/ethanol; j) triethylamine trihydrofluoride.

Synthesis 3: Synthesis of Cyclic (guanosine-(2'→5')-monophosphorothioate-5,6-dichlorobenzimidazole riboside-(3'→5')-monophosphorothioate) (c[G(2',5')pS-DCIBI(3',5')pS]).

Legend for Synthesis 3: Synthetic steps: a) pyridinium trifluoroacetate/$H_2O$; b) tert.-butylamine; c) dichloroacetic acid/$H_2O$; d) A, pyridine; e) 3-((N,N-dimethylaminomethylidene)amino)-3H-1,2,4-dithiazole-5-thione (DDTT); f) dichloroacetic acid/$H_2O$; g) 2-chloro-5,5-dimethyl-1,3,2-dioxaphosphorinane-2-oxide; h) 3-H-1,2-benzodithiol-3-one; I) methylamine/ethanol; j) triethylamine trihydrofluoride.

Synthesis 4: Biological activity of new inventive CDNs by means of THP1-Blue™ cells and SEAP reporter.

Legend for Synthesis 4: THP1-Blue™ cells ((THP1-ISG); InvivoGen, catalogue number: thp-isg; concentration: $5 \times 10^5$/ml, 180 µl/well (96-well-plate) were incubated with inventive CDNs in different concentrations (0 µg/ml; 10 µg/ml; 20 µg/ml; 40 µg/ml) in medium (RPMI-1640, 2 mM L-glutamine, 1.5 g/l sodium bicarbonate, 4.5 g/l glucose, 10 mM HEPES, 1 mM sodium pyruvate, 10% FCS, 100 µg/ml Zeocin™, 110 µg/ml Normocin™, Pen-Strep 50 U/ml) for 24 hours at 37° C. in 5% $CO_2$. The quantification was performed with SEAP detection reagent QUANTI-Blue™ (InvivoGen; catalogue number: rep-qb1; incubation time: 30 min at 37° C. in 5% $CO_2$) by optical density (OD) determination at 625 nm.

Synthesis 5: Biological activity of new inventive CDNs by means of THP1-Blue™ cells and THP1 Dual™ KO STING cells, respectively, as control cells and SEAP reporter.

Legend for Synthesis 5: THP1-Blue™ cells ((THP1-ISG); InvivoGen, catalogue number: thp-isg; concentration: $5\times10^5$/ml, 180 µl/well (96-well-plate) and THP1 Dual™ KO STING cells ((STING KO) InvivoGen, catalogue number: thpd-kostg; concentration: $5\times10^5$/ml, 180 µl/well (96-well-plate) were incubated with inventive CDNs (concentration 40 µg/ml each) in medium (RPMI-1640, 2 mM L-glutamine, 1.5 g/l sodium bicarbonate, 4.5 g/l glucose, 10 mM HEPES, 1 mM sodium pyruvate, 10% FCS, 100 µg/mL Zeocin™, 110 µg/mL Normocin™, Pen-Strep 50 U/mL) for 24 hours at 37° C. in 5% $CO_2$. For incubations with THP1 Dual™ KO STING cells, 10 µg/ml of blasticidin were added to the medium. Quantification was performed with SEAP detection reagent QUANTI-Blue™ (InvivoGen; catalogue number: rep-qb1; incubation time: 15 min at 37° C. in 5% $CO_2$) by optical density (OD) determination at 625 nm.

Table 1: Abbreviations, names and structures of the new inventive compounds.

Table 2: HPLC Retention times and lipophilicity data (log $k'_0$) of new inventive CDNs.

DETAILED DESCRIPTION OF EMBODIMENTS OF THE INVENTION

The benzimidazole-containing cyclic dinucleotides according to this invention are compounds of the Formula (I)

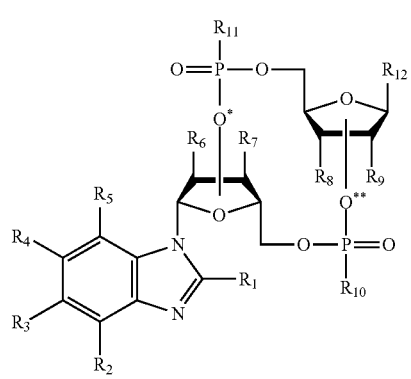

Formula (I)

wherein the oxygen marked with one asterisk (*) is connected as $R_6$ or $R_7$ and the oxygen marked with two asterisks (**) is connected as $R_8$ or $R_9$;
and wherein $R_1$ is
H, Cl, Br, I, F, $N_3$, $NO_2$, OH, SH, $NH_2$, $CF_3$, alkyl, aryl, aralkyl, acyl, aracyl, S-alkyl, S-aryl, S-aralkyl, S-acyl, S-aracyl, S(O)-alkyl, S(O)-aryl, S(O)-aralkyl, S(O)-acyl, S(O)-aracyl, $S(O)_2$-alkyl, $S(O)_2$-aryl, $S(O)_2$-aralkyl, $S(O)_2$-acyl, $S(O)_2$-aracyl, $NR_{13}R_{14}$ (wherein $R_{13}$ and $R_{14}$ can independently be H, alkyl, aryl or aralkyl), 2-furyl, 3-furyl, 2-bromo-5-furyl, (2-furyl)thio, (3-(2-methyl)furyl)thio, (3-furyl)thio, 2-thienyl, 3-thienyl, (5-(1-methyl)tetrazolyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, (7-(4-methyl)coumarinyl)thio, (4-(7-methoxy)coumarinyl)thio, (2-naphtyl)thio, 4-pyridyl, (4-pyridyl)thio, 2-pyridylthio, 5-amino-3-oxopentylamino, 8-amino-3,6-dioxooctylamino, 19-amino-4,7,10,13,16-pentaoxanonadecylamino, 17-amino-9-aza-heptadecylamino, 4-(N-methylanthranoyl)aminobutylamino, dimethylamino, diethylamino, 4-morpholino, 1-piperidino or 1-piperazino or the residue $R_1$ is as defined in the following Groups 1 or 2:

Group 1:

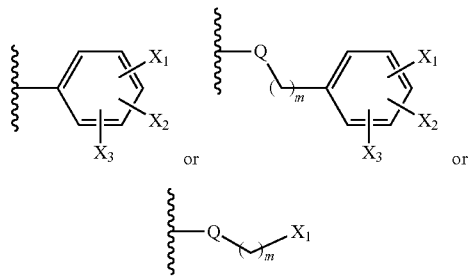

wherein
m=0-6;
Q=S, S(O), $S(O)_2$, O, NH, $CH_2$ or C(O);
$X_1$, $X_2$ and $X_3$ are independently of each other H, OH, $NH_2$, $N_3$, SH, CN, $NO_2$, F, Cl, Br, I, $(CH_2)_nCH_3$ (with n=0-5), i-Pr, t-Bu, (with n=0-5), $(CH_2)_nCH=CH_2$ (with n=0-5), $CH_2OH$, $(CH_2)_nOCH_3$ (with n=1-2), $CH_2N(CH_3)_2$, $O(CH_2)_nCH_3$ (with n=0-5), 01-Pr, OCy, OCyp, OBn, $OC(O)CH_3$, OC(O)Ph, $OCF_3$, $N(CH_3)_2$, $NH(CH_2)_nCH_3$ (with n=0-5), NHC(O)t-Bu, NHC(O)Ph, NHC(O)Ot-Bu, $NHC(O)CH_3$, $NHC(O)CH_2N_3$, $B(OH)_2$, $CF_3$, C(O)OH, $C(O)OCH_3$, O(O)Oi-Pr, C(O)Ot-Bu, C(O)OPh, C(O)OBn, $C(O)NH_2$, $C(O)N(CH_3)_2$, C(O)NHPh, C(O)NHBn, $C(O)CF_3$, $CH_2C(O)OH$, $CH_2C(O)OCH_3$, $CH_2C(O)Oi$-Pr, $CH_2C(O)Ot$-Bu, $CH_2C(O)OBn$, $S(CH_2)_nCH_3$ (with n=0-5), $S(CH_2)_nOEt$ (with n=1-4), SBn, $SO_2CH_3$, $SO_2CF_3$,

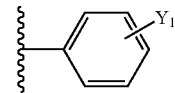

(with $Y_1$=H, SH, CN, Ph, F, $CH_3$, $OCH_3$, $SCH_3$, 4-thiophenyl, $NO_2$, pentyl),

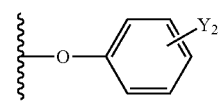

(with $Y_2$=H, SH, F),

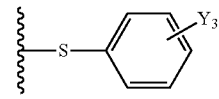

(with $Y_3$=H, SH),

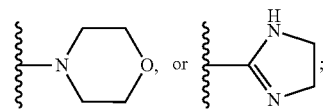

Group 2:

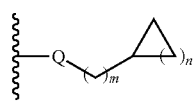

wherein
m=0-6;
n=1-6;
Q=S, S(O), S(O)$_2$, O or NH;
R$_2$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_3$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_4$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_5$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_6$ or R$_7$ is H, OH, NH$_2$, F, O—CH$_3$, S—CH$_3$, OCH$_2$C≡C, OCH$_2$CH=CH$_2$, O-acyl, O-aracyl, O—C(O)NH—(CH$_2$)$_6$NH$_2$ or O—(N'-methylanthraniloyl), while the other residue R$_6$ or R$_7$ represents the connection with the oxygen marked with one asterisk (*)
R$_8$ or R$_9$ is H, OH, NH$_2$, F, O—CH$_3$, S—CH$_3$, OCH$_2$C≡C, OCH$_2$CH=CH$_2$, O-acyl, O-aracyl, O—C(O)NH—(CH$_2$)$_6$NH$_2$ or, O—(N'-methylanthraniloyl), while the other residue R$_6$ or R$_7$ represents the connection with the oxygen marked with two asterisks (**)
R$_{10}$ is OH, SH, borano (BH$_3$), S-PAS, O-PAS, S-BAS or O-BAS,
  wherein PAS is a photo-activatable protecting group, preferably o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl) methyl (BCMCM-caged),
  and wherein BAS is a bio-activatable protecting group, preferably methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl;
R$_{11}$ is OH, SH, borano (BH$_3$), S-PAS, O-PAS, S-BAS or O-BAS,
  wherein PAS is a photo-activatable protecting group, preferably o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl) methyl (BCMCM-caged),
  and wherein BAS is a bio-activatable protecting group, preferably methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, 4-benzoyloxybenzyl;
R$_{12}$ is

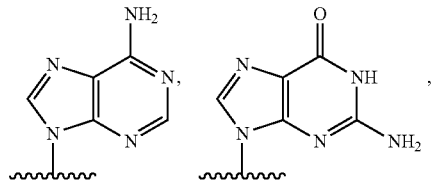

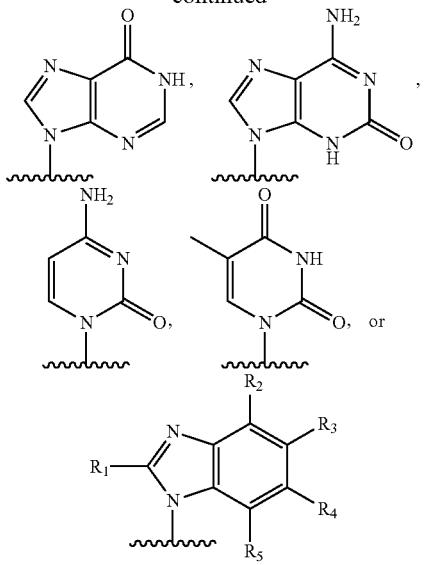

while R$_1$ up to R$_5$ are defined as described above.
wherein R$_{12}$ has the structure

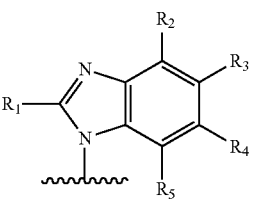

and one, two, three, four or all residues R$_1$, R$_2$, R$_3$, R$_4$ and R$_5$ are equal or unequal to the other residue with the same index.

All synthetic CDNs described so far in the literature carry solely the nucleobases adenine, guanine, hypoxanthine or isoguanine, with purine or substituted purine bases.

CDNs with these nucleobases all have in common a considerably high polarity, which leads to poor membrane permeability of the resulting CDNs.

In order to remedy this drawback of the well-known CDNs, the present invention solves the problem by exchange of at least one of the polar nucleobases adenine, guanine, hypoxanthine or isoguanine by a lipophilic structural unit. Surprisingly, such inventive modified CDNs still bind to the STING receptor protein and/or activate STING-modulated signalling pathways.

Surprising as well is the fact that the inventive substitution of a CDN nucleobase with a benzimidazole unit leads to much higher lipophilicity, although this structural element differs only slightly from the purine parent structure.

Especially, by means of a published and commonly accepted HPLC gradient system (example 18) it can be shown, that the new inventive CDNs which contain at least one unsubstituted or substituted benzimidazole nucleobase have considerably higher lipophilicity.

It is commonly accepted that increased lipophilicity correlates directly with improved membrane permeability.

Unexpected and surprising as well are the properties of the new inventive CDNs with respect to the activation of the STING-regulated signalling pathways in commonly accepted and literature-known biological cell systems, as described in Examples 19 to 22.

In more detail, many of the inventive CDNs show biological activity with respect to the STING-induced dimerisation of IRF3, the STING-induced phosphorylation of IRF3 and the STING-induced phosphorylation of TBK1 (Example 19), the STING-modulated increase of the β-interferone production (Example 20), the increase of the mRNA formed for α and β interferone (Example 21) and the amount of β-interferone secreted (Example 22).

Thus, despite the fact, that at least one of the native nucleobases or nucleobase analogues were exchanged against one or two unsubstituted or substituted benzimidazole units, the new benzimidazole-containing CDNs do not lead to partial or complete inactivity, but surprisingly are still capable to activate STING-dependent signalling processes.

For the reasons mentioned above the result that quite a number of the inventive CDNs are capable to bind to the STING protein with good affinities, as measured by means of Isothermal Titration calorimetry (ITC) and described in Example 23, was surprising as well. The affinities recorded for several of the inventive CDNs were in the same range or even better, as those obtained from the natural CDNs.

Preferred Inventive Compounds of the General Formula (I)

Preferred is the previously defined compound of the Formula (I), wherein $R_{10}$ or $R_{11}$ is SH and which is described by the general abbreviation c[$N_1$(2',5')pS-$N_2$(3',5')p], c[$N_1$(2',5')pS-$N_2$(2',5')p], c[$N_1$(3',5')pS-$N_2$(2',5')p] or c[$N_1$(3',5')pS-$N_2$(3',5')pS] (as defined previously).

Preferred as well is the previously defined compound of the Formula (I), wherein $R_{10}$ or $R_{11}$ is SH and which is described by the general abbreviation c[$N_1$(2',5')p-$N_2$(3',5')pS], c[$N_1$(2',5')p-$N_2$(2',5')S], c[$N_1$(3',5')p-$N_2$(2',5')pS] or c[$N_1$(3',5')p-$N_2$(3',5')pS] (as defined previously).

Preferred as well is the previously defined compound of the Formula (I), wherein $R_{10}$ or $R_{11}$ is $BH_3$ and which is described by the general abbreviation c[$N_1$(2',5')pB-$N_2$(3',5')pB], c[$N_1$(2',5')pB-$N_2$(2',5')p], c[$N_1$(3',5')pB-$N_2$(2',5')p] or c[$N_1$(3',5')pB-$N_2$(3',5')pB] (as defined previously).

Preferred as well is the previously defined compound of the Formula (I), wherein $R_{10}$ or $R_{11}$ is $BH_3$ and which is described by the general abbreviation c[$N_1$(2',5')p-$N_2$(3',5')pB], c[$N_1$(2',5')p-$N_2$(2',5')B], c[$N_1$(3',5')p-$N_2$(2',5')pB] or c[$N_1$(3',5')p-$N_2$(3',5')pB] (as defined previously).

Preferred as well is the previously defined compound of the Formula (I), wherein $R_{10}$ and $R_{11}$ is $BH_3$ and which is described by the general abbreviation c[$N_1$(2',5')pB-$N_2$(3',5')pB], c[$N_1$(2',5')pB-$N_2$(2',5')pB], c[$N_1$(3',5')pB-$N_2$(2',5')pB] or c[$N_1$(3',5')pB-$N_2$(3',5')pB] (as defined previously).

Preferred as well is the previously defined compound of the Formula (I), wherein $R_{10}$ or $R_{11}$ is SH and and corresponding $R_{11}$ or $R_{10}$ is $BH_3$ which is described by the general abbreviation c[$N_1$(2',5')pS-$N_2$(3',5')pB], c[$N_1$(2',5')pS-$N_2$(2',5')pB], c[$N_1$(3',5')pS-$N_2$(2',5')pB] or c[$N_1$(3',5')pS-$N_2$(3',5')pB] (as defined previously).

Preferred as well is the previously defined compound of the Formula (I), wherein $R_{10}$ or $R_{11}$ is $BH_3$ and and corresponding $R_{11}$ or $R_{10}$ is SH and which is described by the general abbreviation c[$N_1$(2',5')pB-$N_2$(3',5')pS], c[$N_1$(2',5')pB-$N_2$(2',5')pS], c[$N_1$(3',5')pB-$N_2$(2',5')pS] oder c[$N_1$(3',5')pB-$N_2$(3',5')pS] (as defined previously).

Further preferred is the previously defined compound of the Formula (I), wherein $R_{10}$ and $R_{11}$ is SH and which is described by the general abbreviation c[$N_1$(2',5')pS-$N_2$(3',5')pS], c[$N_1$(2',5')pS-$N_2$(2',5')pS], c[$N_1$(3',5')pS-$N_2$(2',5')pS] or c[$N_1$(3',5')pS-$N_2$(3',5')pS] (as defined previously).

Further preferred is the previously defined compound of the Formula (I), wherein the phosphate bridges of the variably connectable structural unit are connected via $R_8$ and $R_7$ and lead to structures, which are commonly designated as "3',5'-3',5'-" connected.

Further preferred is the previously defined compound of the Formula (I), wherein the phosphate bridges of the variably connectable structural unit are connected via $R_8$ and $R_7$ and lead to structures, which are commonly designated as "2',5'-3',5'-" connected.

In an additional special embodiment the previously defined compound of the Formula (I) is a structure, wherein $R_2$ is $CH_3$.

In an additional special embodiment the previously defined compound of the Formula (I) is a structure, wherein $R_2$ is $NO_2$.

In an additional special embodiment the previously defined compound of the Formula (I) is a structure, wherein $R_2$ is $NH_2$.

In an additional special embodiment the previously defined compound of the Formula (I) is a structure, wherein $R_2$ is Cl.

In an additional special embodiment the previously defined compound of the Formula (I) is a structure, wherein each, $R_3$ and $R_4$ are $CH_3$.

In an additional special embodiment the previously defined compound of the Formula (I) is a structure, wherein each, $R_3$ and $R_4$ are O—$CH_3$.

In an additional special embodiment the previously defined compound of the Formula (I) is a structure, wherein each, $R_3$ and $R_4$ are $NO_2$.

In an additional special embodiment the previously defined compound of the Formula (I) is a structure, wherein each, $R_3$ and $R_4$ are Cl.

In an additional special embodiment the previously defined compound of the Formula (I) is a structure, wherein each, $R_3$ and $R_4$ are Cl and wherein $R_1$ is not H.

In an additional special embodiment the previously defined compound of the Formula (I) is a structure, wherein each, $R_1$, $R_3$ and $R_4$ are Cl.

In an additional special embodiment the previously defined compound of the Formula (I) is a structure, wherein $R_1$ is $CF_3$ and wherein each, $R_3$ and $R_4$ are Cl.

In an additional special embodiment the previously defined compound of the Formula (I) is a structure, wherein each, $R_6$ or $R_7$ and $R_8$ or $R_9$ are OH.

In an additional special embodiment the previously defined compound of the Formula (I) is a structure, wherein $R_6$ or $R_7$ is F and $R_8$ or $R_9$ are OH.

In an additional special embodiment the previously defined compound of the Formula (I) is a structure, wherein $R_6$ or $R_7$ is OH and $R_8$ or $R_9$ are F.

In an additional special embodiment the previously defined compound of the Formula (I) is a structure, wherein each, $R_6$ or $R_7$ and $R_8$ or $R_9$ are F.

Any meaningful combination out of the embodiments described above are within the scope of this invention as well Especially preferred are embodiments of the invention based on statements given above and as defined in one of the claim 2, 3, 4, 5, 6 or 7.

Especially preferred are the inventive compounds which are listed and depicted in Table 1 and defined in claim 8.

It should be noted that, in case of any doubt, for the entire present description of the invention and especially for the compounds listed in Table 1, the depicted structure is valid.

It should further be noted that the compounds listed in Table 1 are depicted in the free acid form. The present invention, however, comprises physiologically acceptable salt forms as well, with cations such as—but not limited to—$Na^+$, $K^+$, $Li^+$, $NH_4^+$, $Et_3NH^+$ and $(i\text{-}Pr)_2EtNH^+$ or mixed forms out of the previously listed ions.

TABLE 1

Abbreviations, names and structures of the new, inventive compounds

| # | Compound | Structure |
|---|---|---|
| 1 | c[BI(3',5')pBI(3',5')p] cyclic (benzimidazole riboside-(3' –> 5')-monophosphate-benzimidazole riboside-(3' –> 5')-monophosphate) | 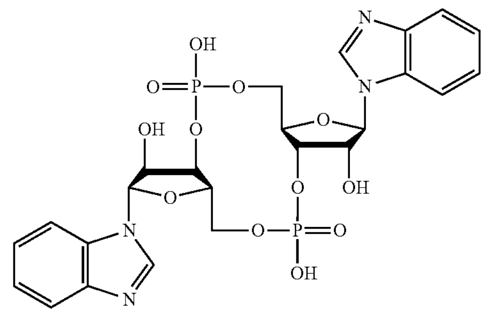 |
| 2 | c[BI(2',5')pBI(3',5')p] cyclic (benzimidazole riboside-(2' –> 5')-monophosphate-benzimidazole riboside-(3' –> 5')-monophosphate) | 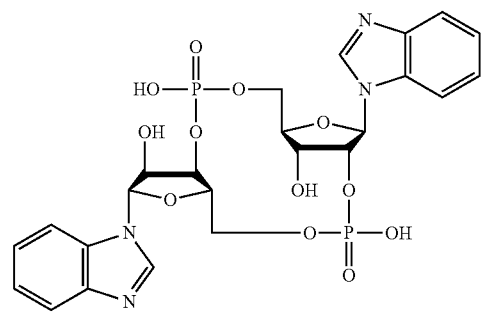 |
| 3 | c[BI(2',5')pBI(2',5')p] cyclic (benzimidazole riboside-(2' –> 5')-monophosphate-benzimidazole riboside-(2' –> 5')-monophosphate) | 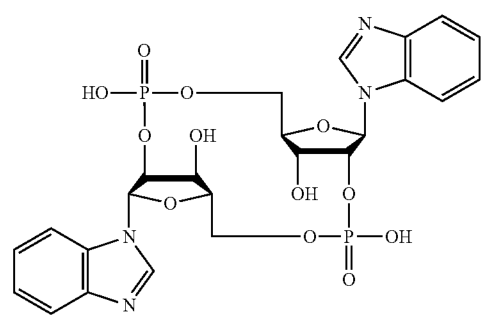 [SMILES: O=P1(O)OC[C@H]2O[C@@H](n3cnc4ccccc43)[C@@H](OP(=O)(O)OC[C@H]3O[C@@H](n4cnc5ccccc54)C(O1)[C@H]3O)C2O] |
| 4 | c[BI(3',5')pS-BI(3',5')pS] cyclic (benzimidazole riboside-(3' –> 5')-monophosphorothioate-benzimidazole riboside-(3' –> 5')-monophosphorothioate) | 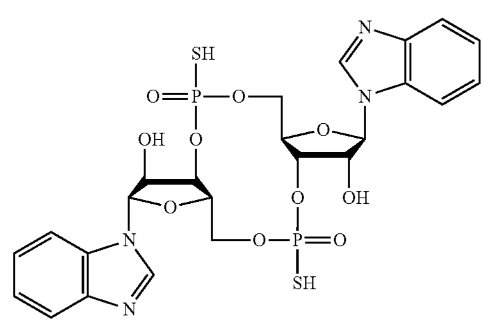 |

TABLE 1-continued

Abbreviations, names and structures of the new, inventive compounds

| # | Compound | Structure |
|---|----------|-----------|
| 5 | c[BI(2',5')pS-BI(3',5')pS] cyclic (benzimidazole riboside-(2' -> 5')-monophosphorothioate-benzimidazole riboside-(3' -> 5')-monophosphorothioate) | 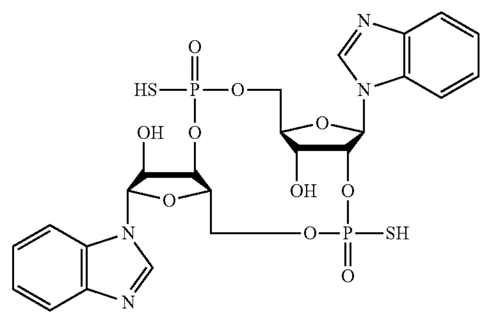 |
| 6 | c[BI(2',5')pS-BI(2',5')pS] cyclic (benzimidazole riboside-(2' -> 5')-monophosphorothioate-benzimidazole riboside-(2' -> 5')-monophosphorothioate) | 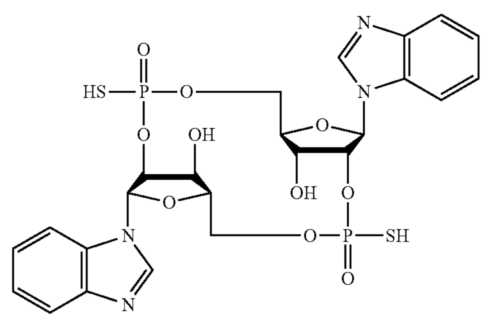 [SMILES: O=P1(S)OC[C@H]2O[C@@H](n3cnc4ccccc43)[C@@H](OP(=O)(S)OC[C@H]3O[C@@H](n4cnc5ccccc54)C(O1)[C@H]3O)C2O] |
| 7 | c[DClBI(3',5')pDClBI(3',5')p] cyclic (5,6-dichlorobenzimidazole riboside-(3' -> 5')-monophosphate-5,6-dichlorobenzimidazole riboside-(3' -> 5')-monophosphate) | 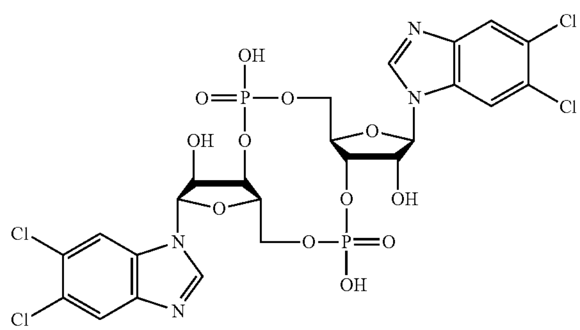 |
| 8 | c[DClBI(2',5')pDClBI(3',5')p] cyclic (5,6-dichlorobenzimidazole riboside-(2' -> 5')-monophosphate-5,6-dichlorobenzimidazole riboside-(3' -> 5')-monophosphate) | 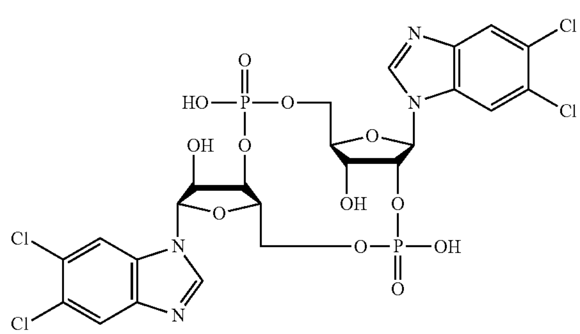 |

TABLE 1-continued

Abbreviations, names and structures of the new, inventive compounds

| # | Compound | Structure |
|---|---|---|
| 9 | c[DClBI(2',5')pDClBI(2',5')p] cyclic (5,6-dichlorobenzimidazole riboside-(2' -> 5')-monophosphate-5,6-dichlorobenzimidazole riboside-(2' -> 5')-monophosphate) | 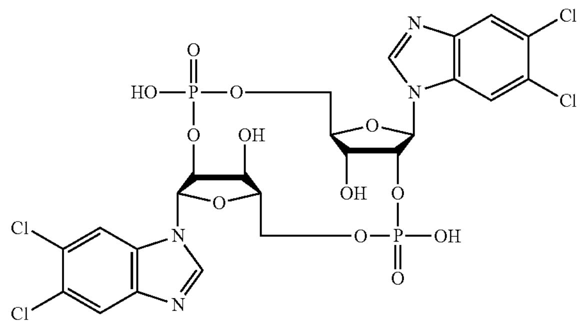 [SMILES: O=P1(O)OC[C@H]2O[C@@H](n3cnc4cc(Cl)c(Cl)cc43)[C@@H](OP(=O)(O)OC[C@H]3O[C@@H](n4cnc5cc(Cl)c(Cl)cc54)C(O1)[C@H]3O)C2O] |
| 10 | c[DClBI(3',5')pS-DClBI(3',5')pS] cyclic (5,6-dichlorobenzimidazole riboside-(3' -> 5')-monophosphorothioate-(5,6-dichlorobenzimidazole riboside-(3' -> 5')-monophosphorothioate) | 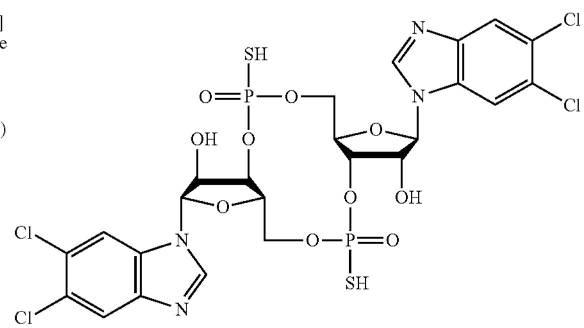 |
| 11 | c[DClBI(2',5')pS-DClBI(3',5')pS] cyclic (5,6-dichlorobenzimidazole riboside-(2' -> 5')-monophosphorothioate-(5,6-dichlorobenzimidazole riboside-(3' -> 5')-monophosphorothioate) | 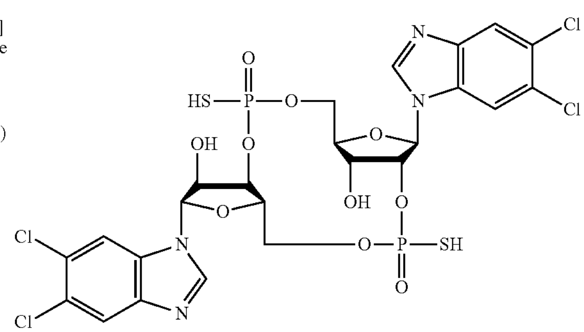 |
| 12 | c[DClBI(2',5')pS-DClBI(2',5')pS] cyclic (5,6-dichlorobenzimidazole riboside-(2' -> 5')-monophosphorothioate-(5,6-dichlorobenzimidazole riboside-(2' -> 5')-monophosphorothioate) | 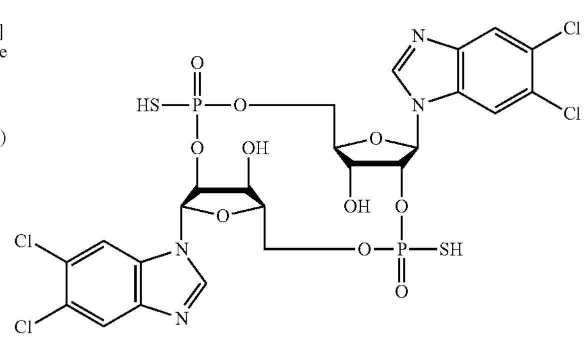 |

TABLE 1-continued

Abbreviations, names and structures of the new, inventive compounds

| # | Compound | Structure |
|---|---|---|
| 13 | c[TClBI(3',5')pTClBI(3',5')p] cyclic (2,5,6-trichlorobenzimidazole riboside-(3' –> 5')-monophosphate-2,5,6-trichlorobenzimidazole riboside-(3' –> 5')-monophosphate) | 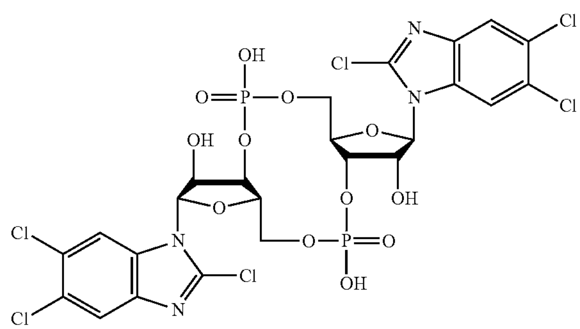 |
| 14 | c[TClBI(2',5')pTClBI(3',5')p] cyclic (2,5,6-trichlorobenzimidazole riboside-(2' –> 5')-monophosphate-2,5,6-trichlorobenzimidazole riboside-(3' –> 5')-monophosphate) | 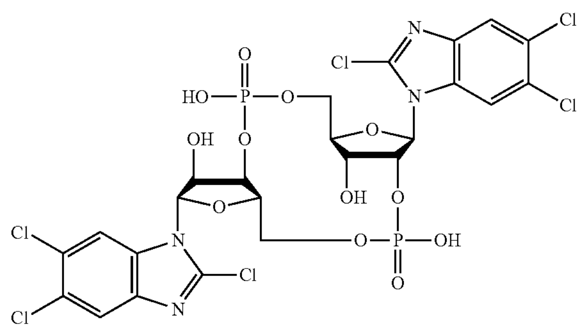 |
| 15 | c[TClBI(2',5')pTClBI(2',5')p] cyclic (2,5,6-trichlorobenzimidazole riboside-(2' –> 5')-monophosphate-2,5,6-trichlorobenzimidazole riboside-(2' –> 5')-monophosphate) | 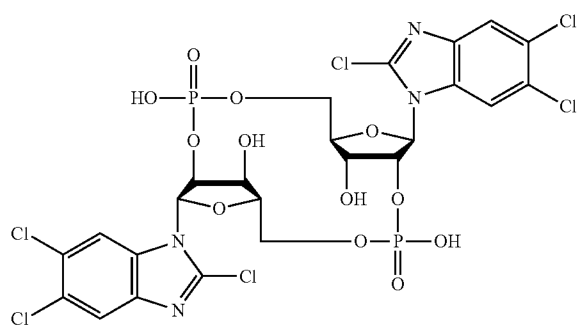 [SMILES: O=P1(O)OC[C@H]2O[C@@H](n3c(Cl)nc4cc(Cl)c(Cl)cc43)[C@@H](OP(=O)(O)OC[C@H]3O[C@@H](n4c(Cl)nc5cc(Cl)c(Cl)cc54)C(O1)[C@H]3O)C2O] |
| 16 | c[TClBI(3',5')pS-TClBI(3',5')pS] cyclic (2,5,6-trichlorobenzimidazole riboside-(3' –> 5')-monophosphorothioate-2,5,6-trichlorobenzimidazole riboside-(3' –> 5')-monophosphorothioate) | 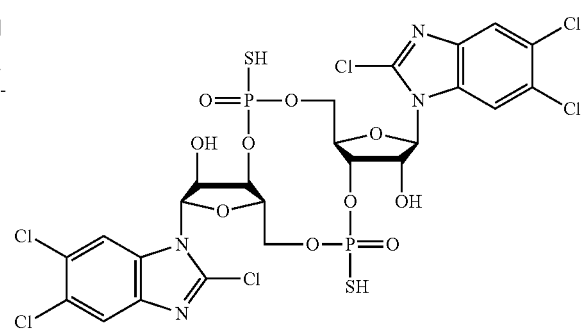 |

TABLE 1-continued

Abbreviations, names and structures of the new, inventive compounds

| # | Compound | Structure |
|---|---|---|
| 17 | c[TClBI(2',5')pS-TClBI(3',5')pS] cyclic (2,5,6-trichlorobenzimidazole riboside-(2' -> 5')-monophosphorothioate-2,5,6-trichlorobenzimidazole riboside-(3' -> 5')-monophosphorothioate) | 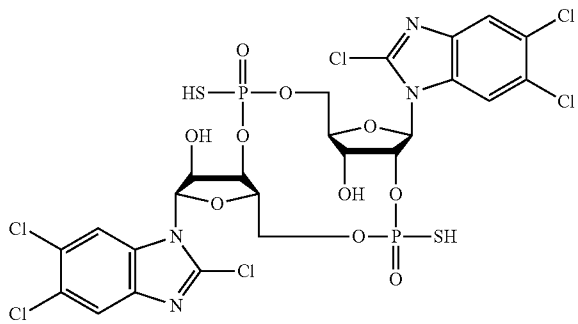 |
| 18 | c[TClBI(2',5')pS-TClBI(2',5')pS] cyclic (2,5,6-trichlorobenzimidazole riboside-(2' -> 5')-monophosphorothioate-2,5,6-trichlorobenzimidazole riboside-(2' -> 5')-monophosphorothioate) | 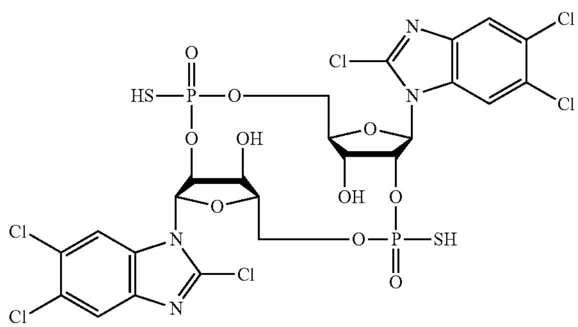 [SMILES: O=P1(S)OC[C@H]2O[C@@H](n3c(Cl)nc4cc(Cl)c(Cl)cc43)[C@@H](OP(=O)(S)OC[C@H]3O[C@@H](n4c(Cl)nc5cc(Cl)c(Cl)cc54)C(O1)[C@H]3O)C2O] |
| 19 | c[G(3',5')pBI(3',5')p] cyclic (guanosine-(3' -> 5')-monophosphate-benzimidazole riboside-(3' -> 5')-monophosphate) | 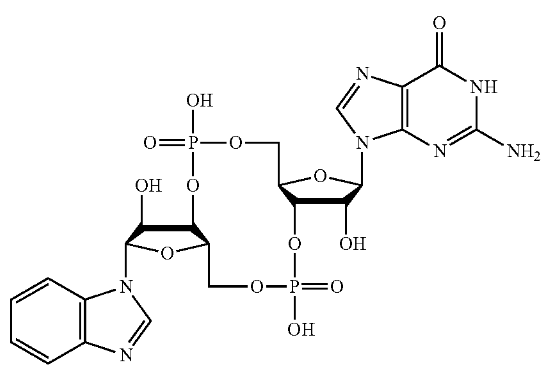 |
| 20 | c[G(2',5')pBI(3',5')p] cyclic (guanosine-(2' -> 5')-monophosphate-benzimidazole riboside-(3' -> 5')-monophosphate) | 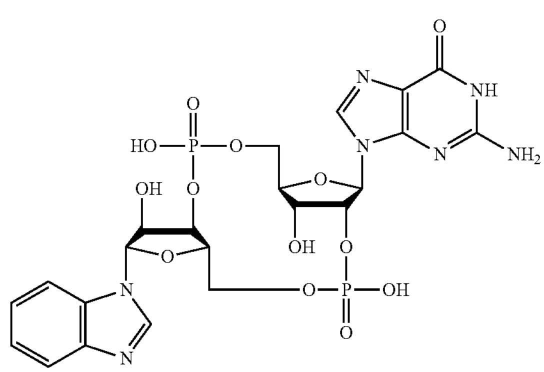 |

TABLE 1-continued

Abbreviations, names and structures of the new, inventive compounds

| # | Compound | Structure |
|---|---|---|
| 21 | c[G(2',5')pBI(2',5')p] cyclic (guanosine-(2' –> 5')-monophosphate-benzimidazole riboside-(2' –> 5')-monophosphate) | 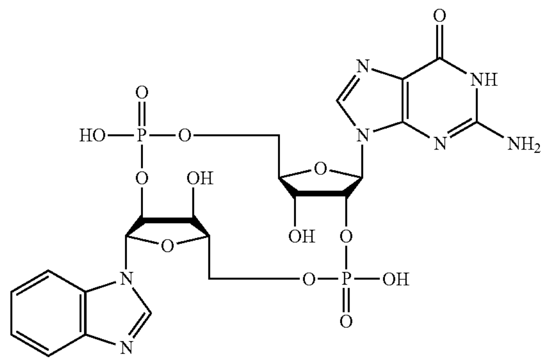 [SMILES: Nc1nc2c(ncn2[C@@H]2O[C@@H]3COP(=O)(O)OC4[C@@H](O)[C@@H](COP(=O)(O)O[C@H]2C3O)O[C@H]4n2cnc3ccccc32)c(=O)[nH]1] |
| 22 | c[G(3',5')pS-BI(3',5')pS] cyclic (guanosine-(3' –> 5')-monophosphorothioate-benzimidazole riboside-(3' –> 5')-monophosphorothioate) | 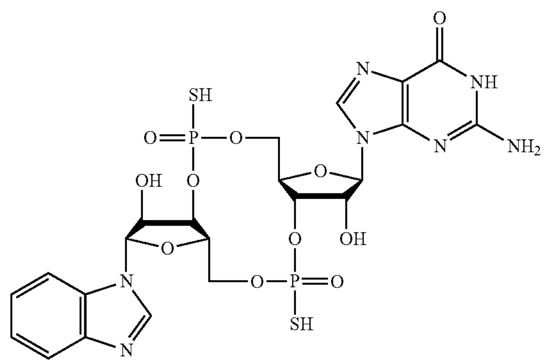 |
| 23 | c[G(2',5')pS-BI(3',5')pS] cyclic (guanosine-(2' –> 5')-monophosphorothioate-benzimidazole riboside-(3' –> 5')-monophosphorothioate) | 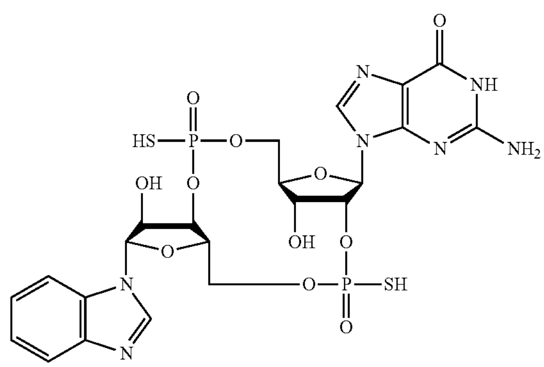 |
| 24 | c[G(2',5')pS-BI(2',5')pS] cyclic (guanosine-(2' –> 5')-monophosphorothioate-benzimidazole riboside-(2' –> 5')-monophosphorothioate) | 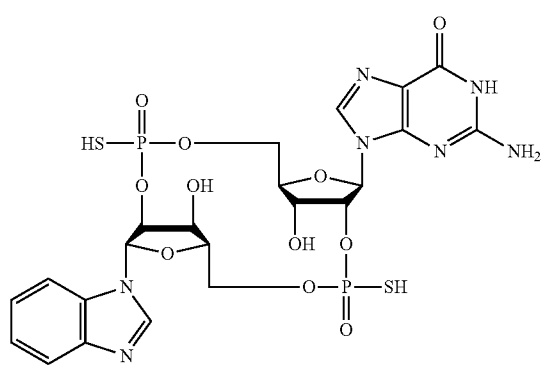 |

TABLE 1-continued

Abbreviations, names and structures of the new, inventive compounds

| # | Compound | Structure |
|---|---|---|
| 25 | c[G(3',5')pDClBI(3',5')p] cyclic (guanosine-(3' -> 5')-monophosphate-5,6-dichlorobenzimidazole riboside-(3' -> 5')-monophosphate) | 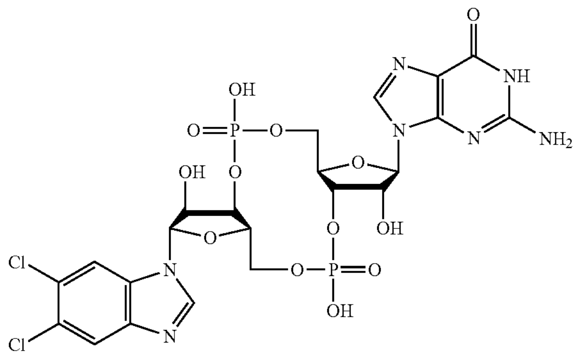 |
| 26 | c[G(2',5')pDClBI(3',5')p] cyclic (guanosine-(2' -> 5')-monophosphate-5,6-dichlorobenzimidazole riboside-(3' -> 5')-monophosphate) | 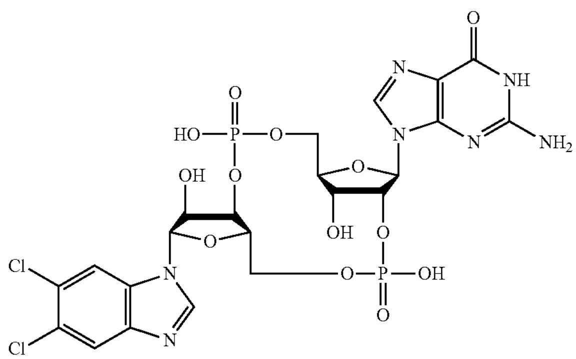 |
| 27 | c[G(2',5')pDClBI(2',5')p] cyclic (guanosine-(2' -> 5')-monophosphate-5,6-dichlorobenzimidazole riboside-(2' -> 5')-monophosphate) | 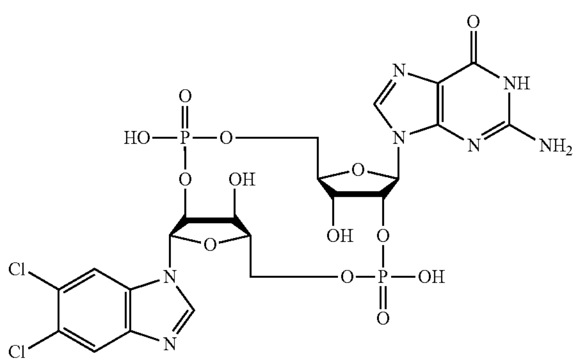 [SMILES: Nc1nc2c(ncn2[C@@H]2O[C@@H]3COP(=O)(O)OC4[C@@H](O)[C@@H](COP(=O)(O)O[C@H]2C3O)O[C@H]4n2cnc3cc(Cl)c(Cl)cc32)c(=O)[nH]1] |
| 28 | c[G(3',5')pS-DClBI(3',5')pS] cyclic (guanosine-(3' -> 5')-monophosphorothioate-5,6-dichlorobenzimidazole riboside-(3' -> 5')-monophosphorothioate) | 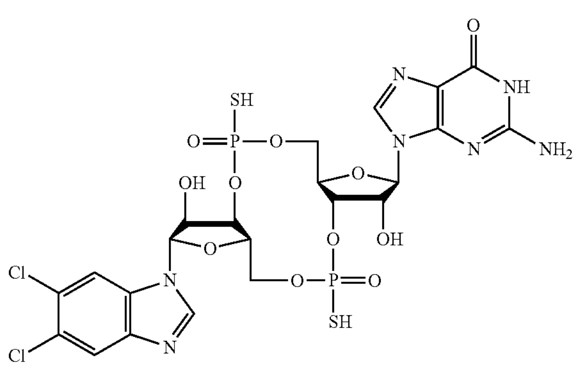 |

TABLE 1-continued

Abbreviations, names and structures of the new, inventive compounds

| # | Compound | Structure |
|---|---|---|
| 29 | c[G(2',5')pS-DClBI(3',5')pS] cyclic (guanosine-(2' -> 5')-monophosphorothioate-5,6-dichlorobenzimidazole riboside-(3' -> 5')-monophosphorothioate) | 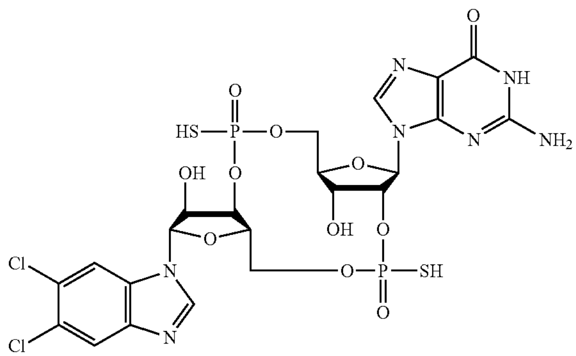 |
| 30 | c[G(2',5')pS-DClBI(2',5')pS] cyclic (guanosine-(2' -> 5')-monophosphorothioate-5,6-dichlorobenzimidazole riboside-(2' -> 5')-monophosphorothioate) | 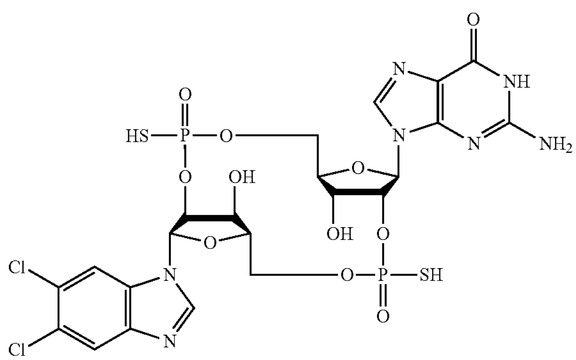 [SMILES: Nc1nc2c(ncn2[C@@H]2O[C@@H]3COP(=O)(S)OC4[C@@H](O)[C@@H](COP(=O)(S)O[C@H]2C3O)O[C@H]4n2cnc3cc(Cl)c(Cl)cc32)c(=O)[nH]1] |
| 31 | c[G(3',5')pTClBI(3',5')p] cyclic (guanosine-(3' -> 5')-monophosphate-2,5,6-trichlorobenzimidazole riboside-(3' -> 5')-monophosphate) | 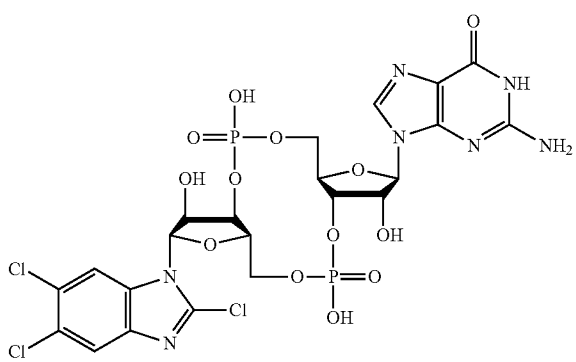 |
| 32 | c[G(2',5')pTClBI(3',5')p] cyclic (guanosine-(2' -> 5')-monophosphate-2,5,6-trichlorobenzimidazole riboside-(3' -> 5')-monophosphate) | 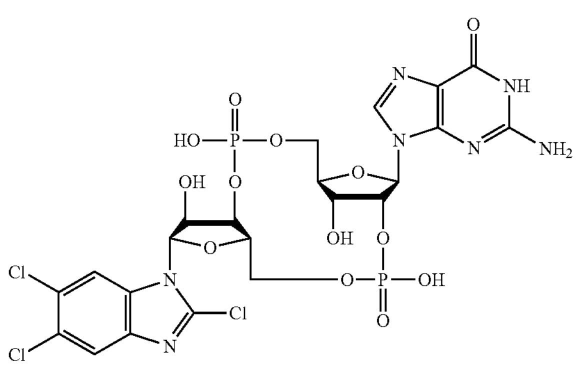 |

TABLE 1-continued

Abbreviations, names and structures of the new, inventive compounds

| # | Compound | Structure |
|---|----------|-----------|
| 33 | c[G(2',5')pTClBI(2',5')p] cyclic (guanosine-(2' –> 5')-monophosphate-2,5,6-trichlorobenzimidazole riboside-(2' –> 5')-monophosphate) | 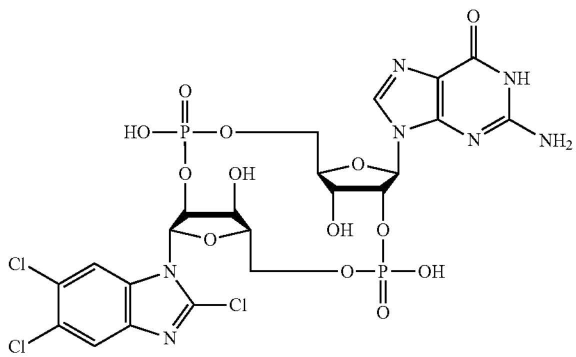 |
| 34 | c[G(3',5')pS-TClBI(3',5')pS] cyclic (guanosine-(3' –> 5')-monophosphorothioate-2,5,6-trichlorobenzimidazole riboside-(3' –> 5')-monophosphorothioate) | 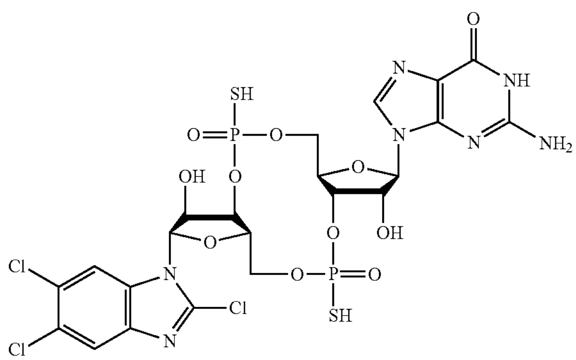 |
| 35 | c[G(2',5')pS-TClBI(3',5')pS] cyclic (guanosine-(2' –> 5')-monophosphorothioate-2,5,6-trichlorobenzimidazole riboside-(3' –> 5')-monophosphorothioate) | 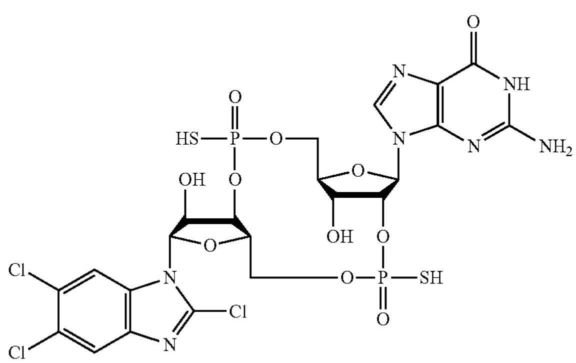 |
| 36 | c[G(2',5')pS-TClBI(2',5')pS] cyclic (guanosine-(2' –> 5')-monophosphorothioate-2,5,6-trichlorobenzimidazole riboside-(2' –> 5')-monophosphorothioate) | 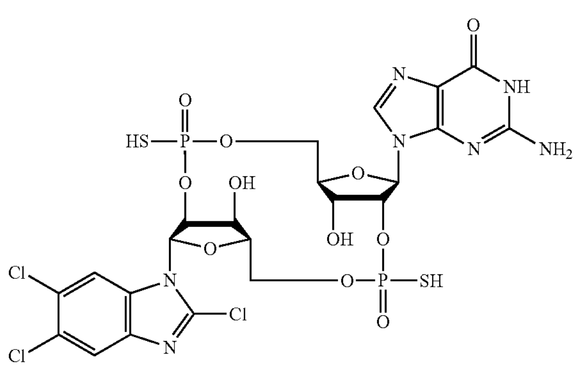 [SMILES: Nc1nc2c(ncn2[C@@H]2O[C@@H]3COP(=O)(S)OC4[C@@H](O)[C@@H](COP(=O)(S)O[C@H]2C3O)O[C@H]4n2c(Cl)nc3cc(Cl)c(Cl)cc32)c(=O)[nH]1] |

TABLE 1-continued

Abbreviations, names and structures of the new, inventive compounds

| # | Compound | Structure |
|---|---|---|
| 37 | c[A(3',5')pBI(3',5')p] cyclic (adenosine-(3' -> 5')-monophosphate-benzimidazole riboside-(3' -> 5')-monophosphate) | 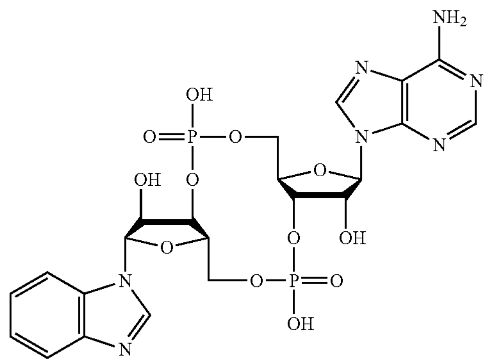 |
| 38 | c[A(2',5')pBI(3',5')p] cyclic (adenosine-(2' -> 5')-monophosphate-benzimidazole riboside-(3' -> 5')-monophosphate) | 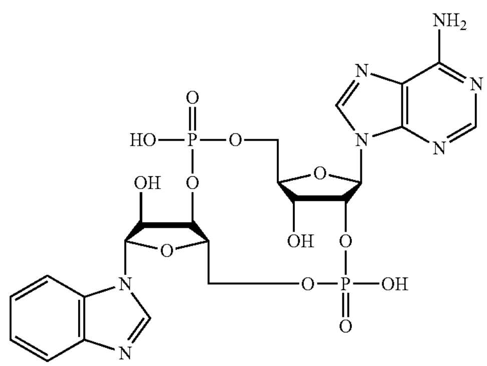 |
| 39 | c[A(2',5')pBI(2',5')p] cyclic (adenosine-(2' -> 5')-monophosphate-benzimidazole riboside-(2' -> 5')-monophosphate) | 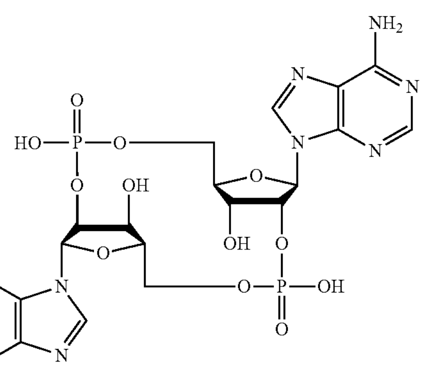 |
| 40 | c[A(3',5')pS-BI(3',5')pS] cyclic (adenosine-(3' -> 5')-monophosphorothioate-benzimidazole riboside-(3' -> 5')-monophosphorothioate) | 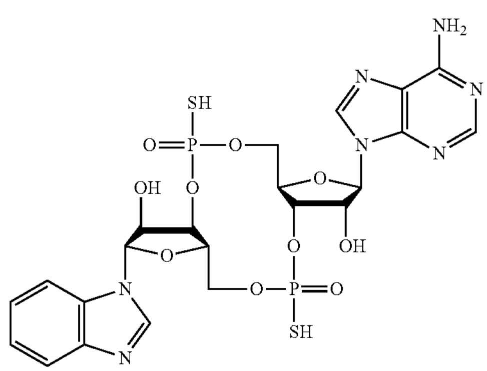 |

TABLE 1-continued

Abbreviations, names and structures of the new, inventive compounds

| # | Compound | Structure |
|---|---|---|
| 41 | c[A(2',5')pS-BI(3',5')pS] cyclic (adenosine-(2' –> 5')-monophosphorothioate-benzimidazole riboside-(3' –> 5')-monophosphorothioate) | 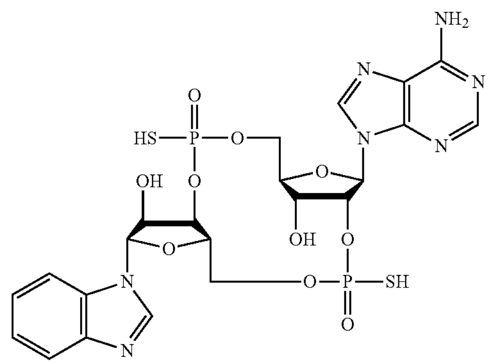 |
| 42 | c[A(2',5')pS-BI(2',5')pS] cyclic (adenosine-(2' –> 5')-monophosphorothioate-benzimidazole riboside-(2' –> 5')-monophosphorothioate) | 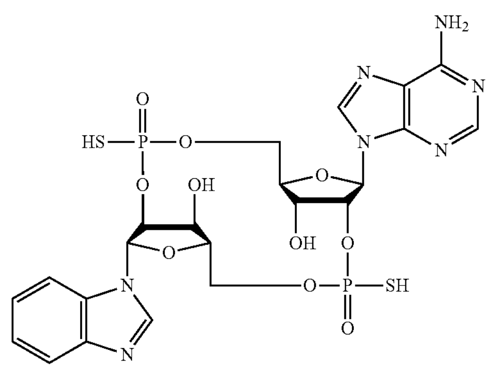 [SMILES: Nc1ncnc2c1ncn2[C@@H]1O[C@@H]2COP(=O)(S)OC3[C@@H](O)[C@@H](COP(=O)(S)O[C@H]1C2O)O[C@H]3n1cnc2ccccc21] |
| 43 | c[A(3',5')pDClBI(3',5')p] cyclic (adenosine-(3' –> 5')-monophosphate-5,6-dichlorobenzimidazole riboside-(3' –> 5')-monophosphate) | 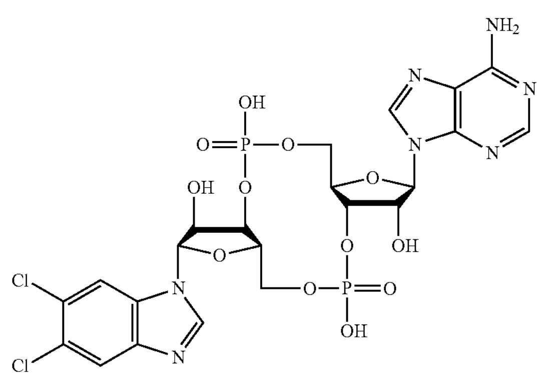 |
| 44 | c[A(2',5')pDClBI(3',5')p] cyclic (adenosine-(2' –> 5')-monophosphate-5,6-dichlorobenzimidazole riboside-(3' –> 5')-monophosphate) | 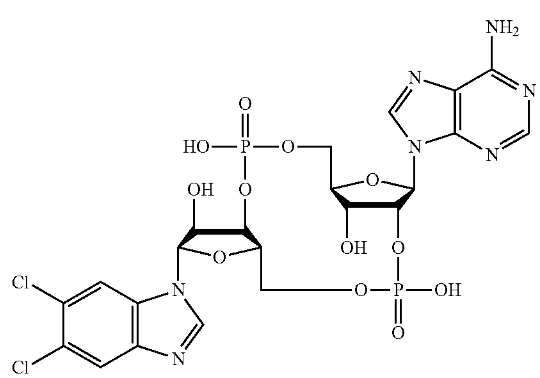 |

TABLE 1-continued

Abbreviations, names and structures of the new, inventive compounds

| # | Compound | Structure |
|---|---|---|
| 45 | c[A(2',5')pDClBI(2',5')p] cyclic (adenosine-(2' -> 5')-monophosphate-5,6-dichlorobenzimidazole riboside-(2' -> 5')-monophosphate) | 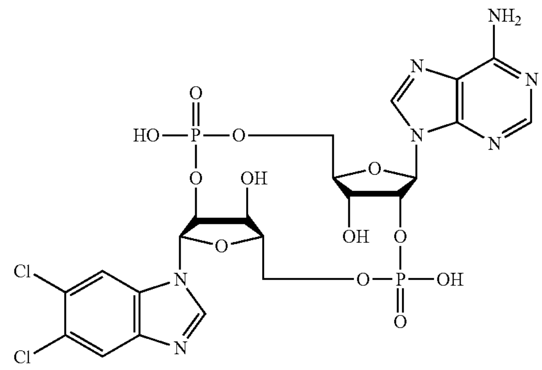 |
| 46 | c[A(3',5')pS-DClBI(3',5')pS] cyclic (adenosine-(3' -> 5')-monophosphorothioate-5,6-dichlorobenzimidazole riboside-(3' -> 5')-monophosphorothioate) | 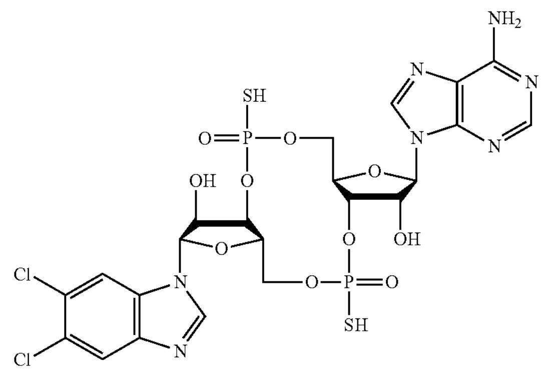 |
| 47 | c[A(2',5')pS-DClBI(3',5')pS] cyclic (adenosine-(2' -> 5')-monophosphorothioate-5,6-dichlorobenzimidazole riboside-(3' -> 5')-monophosphorothioate) | 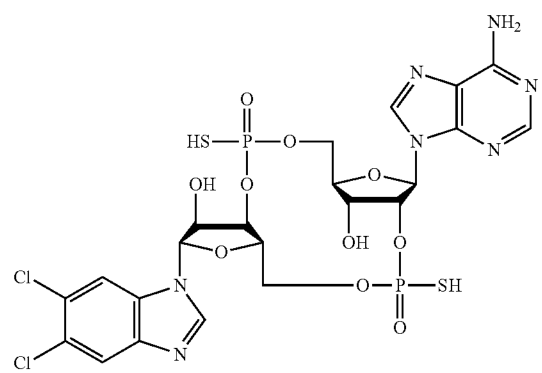 |
| 48 | c[A(2',5')pS-DClBI(2',5')pS] cyclic (adenosine-(2' -> 5')-monophosphorothioate-5,6-dichlorobenzimidazole riboside-(2' -> 5')-monophosphorothioate) | 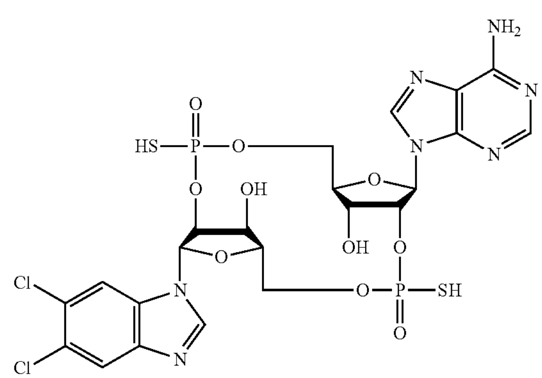 [SMILES: Nc1ncnc2c1ncn2[C@@H]1O[C@@H]2COP(=O)(S)OC3[C@@H](O)[C@@H](COP(=O)(S)O[C@H]1C2O)O[C@H]3n1cnc2cc(Cl)c(Cl)cc21] |

TABLE 1-continued

Abbreviations, names and structures of the new, inventive compounds

| # | Compound | Structure |
|---|---|---|
| 49 | c[A(3',5')pTClBI(3',5')p] cyclic (adenosine-(3' -> 5')-monophosphate-2,5,6-trichlorobenzimidazole riboside-(3' -> 5')-monophosphate) | 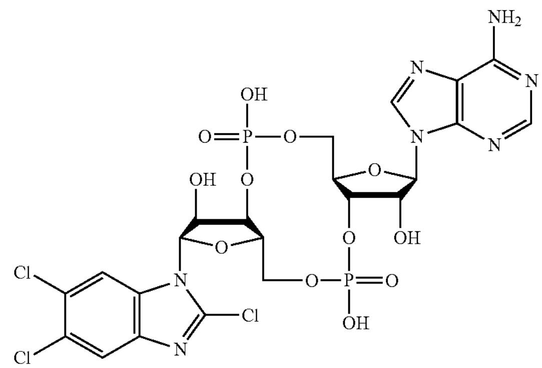 |
| 50 | c[A(2',5')pTClBI(3',5')p] cyclic (adenosine-(2' -> 5')-monophosphate-2,5,6-trichlorobenzimidazole riboside-(3' -> 5')-monophosphate) | 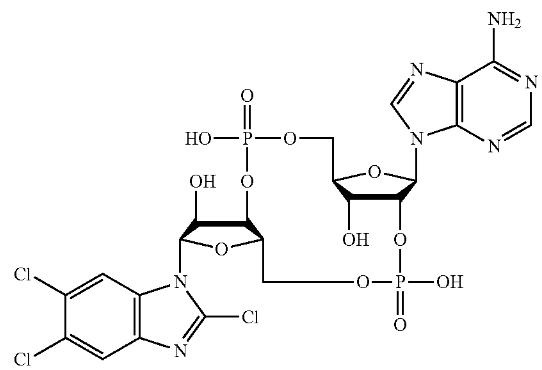 |
| 51 | c[A(2',5')pTClBI(2',5')p] cyclic (adenosine-(2' -> 5')-monophosphate-2,5,6-trichlorobenzimidazole riboside-(2' -> 5')-monophosphate) | 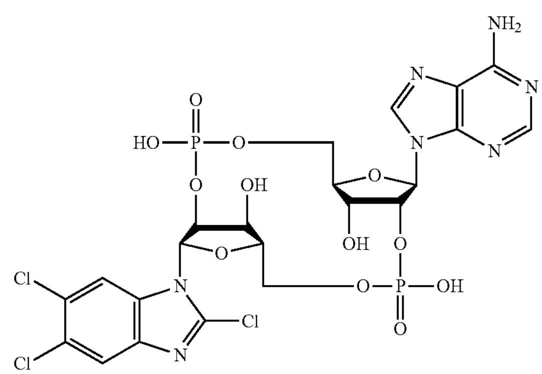 [SMILES: Nc1ncnc2c1ncn2[C@@H]1O[C@@H]2COP(=O)(O)OC3[C@@H](O)[C@@H](COP(=O)(O)O[C@H]1C2O)O[C@H]3n1c(Cl)nc2cc(Cl)c(Cl)cc21] |
| 52 | c[A(3',5')pS-TClBI(3',5')pS] cyclic (adenosine-(3' -> 5')-monophosphorothioate-2,5,6-trichlorobenzimidazole riboside-(3' -> 5')-monophosphorothioate) | 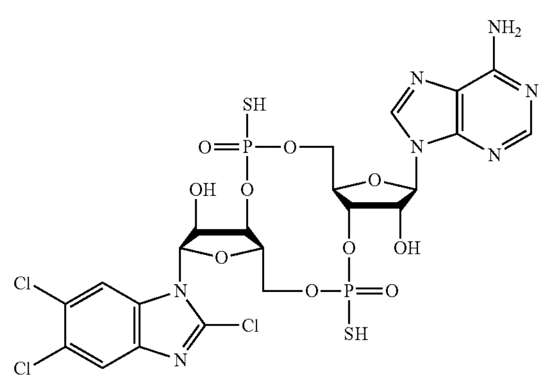 |

TABLE 1-continued

Abbreviations, names and structures of the new, inventive compounds

| # | Compound | Structure |
|---|---|---|
| 53 | c[A(2',5')pS-TClBI(3',5')pS] cyclic (adenosine-(2' –> 5')-monophosphorothioate-2,5,6-trichlorobenzimidazole riboside-(3' –> 5')-monophosphorothioate) | 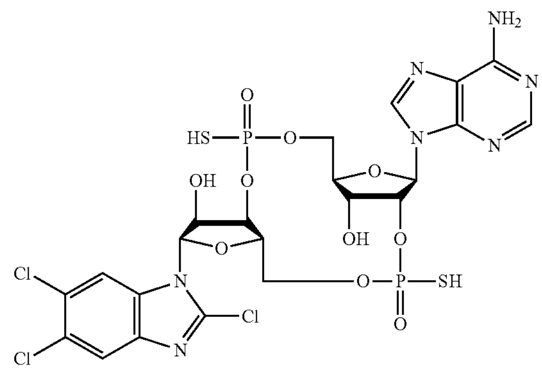 |
| 54 | c[A(2',5')pS-TClBI(2',5')pS] cyclic (adenosine-(2' –> 5')-monophosphorothioate-2,5,6-trichlorobenzimidazole riboside-(2' –> 5')-monophosphorothioate) | 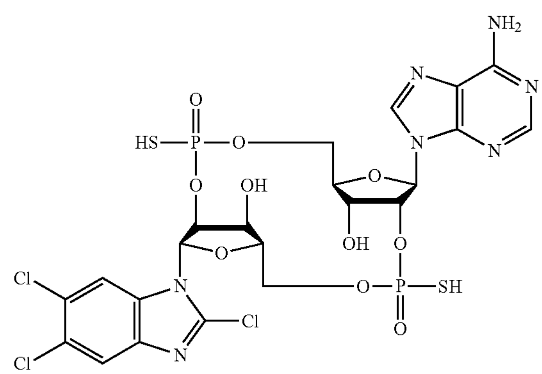 [SMILES: Nc1ncnc2c1ncn2[C@@H]1O[C@@H]2COP(=O)(S)OC3[C@@H](O)[C@@H](COP(=O)(S)O[C@H]1C2O)O[C@H]3n1c(Cl)nc2cc(Cl)c(Cl)cc21] |
| 55 | c[I(3',5')pBI(3',5')p] cyclic (inosine-(3' –> 5')-monophosphate-benzimidazole riboside-(3' –> 5')-monophosphate) | 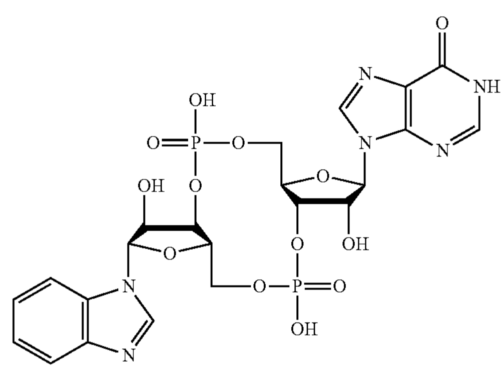 |
| 56 | c[I(2',5')pBI(3',5')p] cyclic (inosine-(2' –> 5')-monophosphate-benzimidazole riboside-(3' –> 5')-monophosphate) | 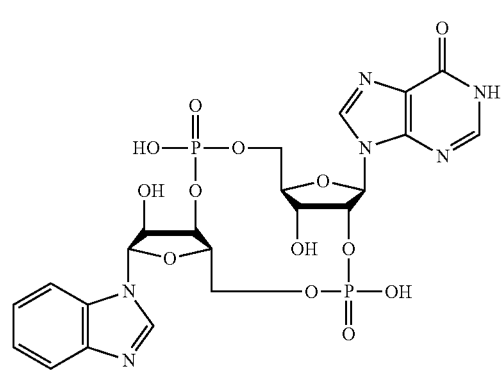 |

TABLE 1-continued

Abbreviations, names and structures of the new, inventive compounds

| # | Compound | Structure |
|---|---|---|
| 57 | c[I(2',5')pBI(2',5')p] cyclic (inosine-(2' -> 5')-monophosphate-benzimidazole riboside-(2' -> 5')-monophosphate) | 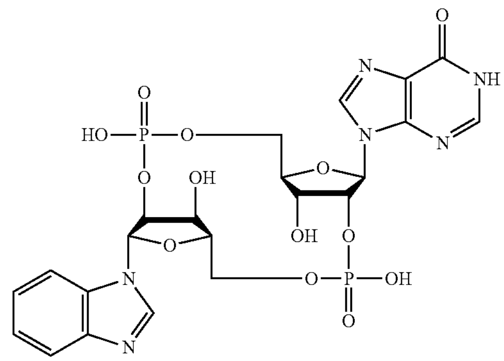 |
| 58 | c[I(3',5')pS-BI(3',5')pS] cyclic (inosine-(3' -> 5')-monophosphorothioate-benzimidazole riboside-(3' -> 5')-monophosphorothioate) | 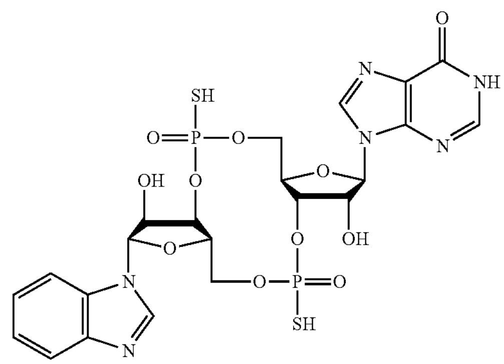 |
| 59 | c[I(2',5')pS-BI(3',5')pS] cyclic (inosine-(2' -> 5')-monophosphorothioate-benzimidazole riboside-(3' -> 5')-monophosphorothioate) | 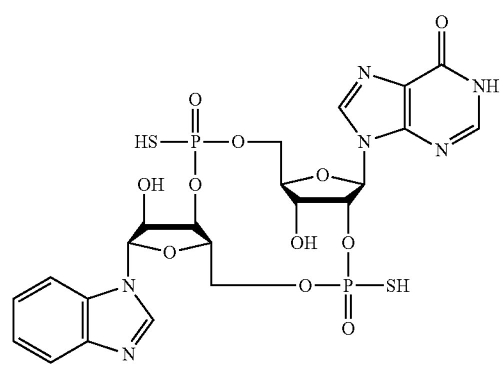 |
| 60 | c[I(2',5')pS-BI(2',5')pS] cyclic (inosine-(2' -> 5')-monophosphorothioate-benzimidazole riboside-(2' -> 5')-monophosphorothioate) | 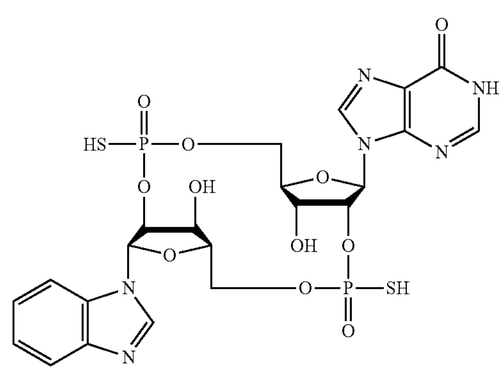 [SMILES: O=c1[nH]cnc2c1ncn2[C@@H]1O[C@@H]2COP(=O)(S)OC3[C@@H](O)[C@@H](COP(=O)(S)O[C@H]1C2O)O[C@H]3n1cnc2ccccc21] |

TABLE 1-continued

Abbreviations, names and structures of the new, inventive compounds

| # | Compound | Structure |
|---|---|---|
| 61 | c[I(3',5')pDClBI(3',5')p] cyclic (inosine-(3' −> 5')-monophosphate-5,6-dichlorobenzimidazole riboside-(3' −> 5')-monophosphate) | 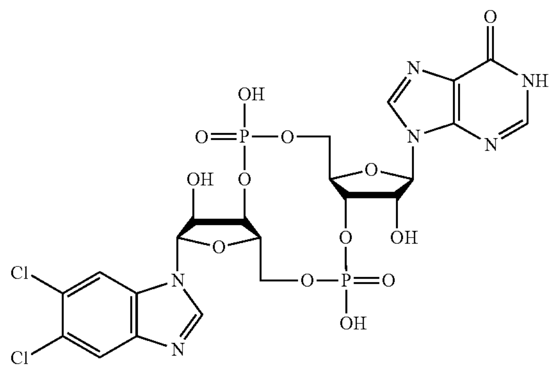 |
| 62 | c[I(2',5')pDClBI(3',5')p] cyclic (inosine-(2' −> 5')-monophosphate-5,6-dichlorobenzimidazole riboside-(3' −> 5')-monophosphate) | 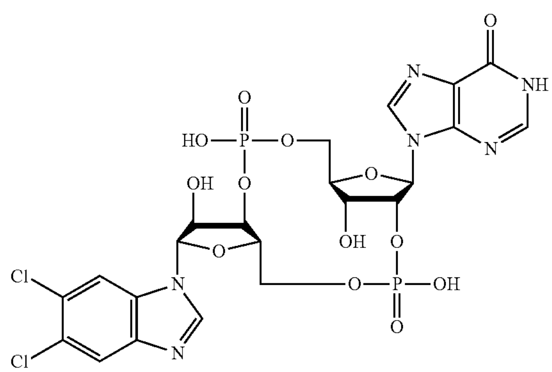 |
| 63 | c[I(2',5')pDClBI(2',5')p] cyclic (inosine-(2' −> 5')-monophosphate-5,6-dichlorobenzimidazole riboside-(2' −> 5')-monophosphate) | 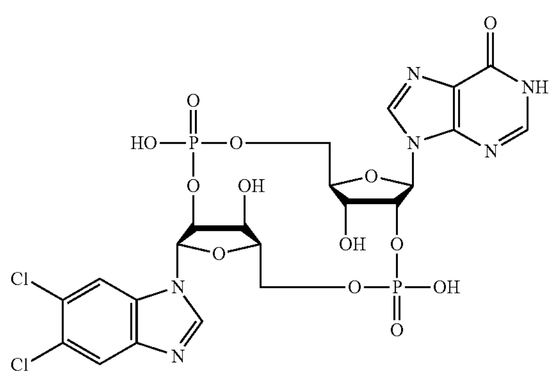 [SMILES: O=c1[nH]cnc2c1ncn2[C@@H]1O[C@@H]2COP(=O)(S)OC3[C@@H](O)[C@@H](COP(=O)(S)O[C@H]1C2O)O[C@H]3n1cnc2cc(Cl)c(Cl)cc21] |
| 64 | c[I(3',5')pS-DClBI(3',5')pS] cyclic (inosine-(3' −> 5')-monophosphorothioate-5,6-dichlorobenzimidazole riboside-(3' −> 5')-monophosphorothioate) | 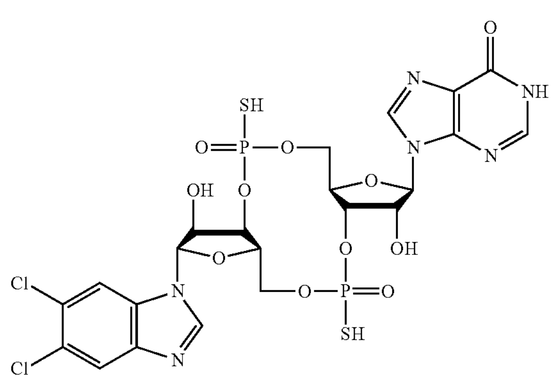 |

TABLE 1-continued

Abbreviations, names and structures of the new, inventive compounds

| # | Compound | Structure |
|---|---|---|
| 65 | c[I(2',5')pS-DClBI(3',5')pS] cyclic (inosine-(2' -> 5')-monophosphorothioate-5,6-dichlorobenzimidazole riboside-(3' -> 5')-monophosphorothioate) | 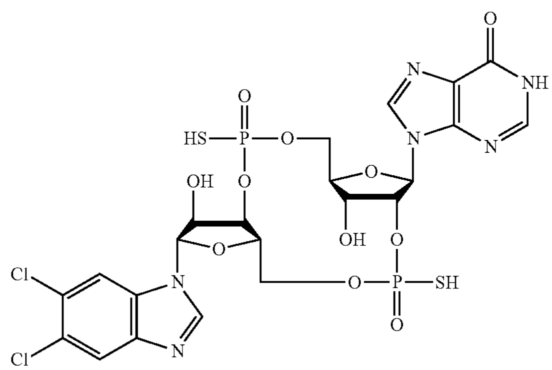 |
| 66 | c[I(2',5')pS-DClBI(2',5')pS] cyclic (inosine-(2' -> 5')-monophosphorothioate-5,6-dichlorobenzimidazole riboside-(2' -> 5')-monophosphorothioate) | 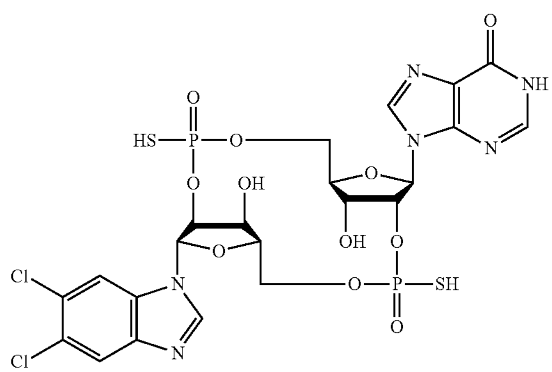 |
| 67 | c[I(3',5')pTClBI(3',5')p] cyclic (inosine-(3' -> 5')-monophosphate-2,5,6-trichlorobenzimidazole riboside-(3' -> 5')-monophosphate) | 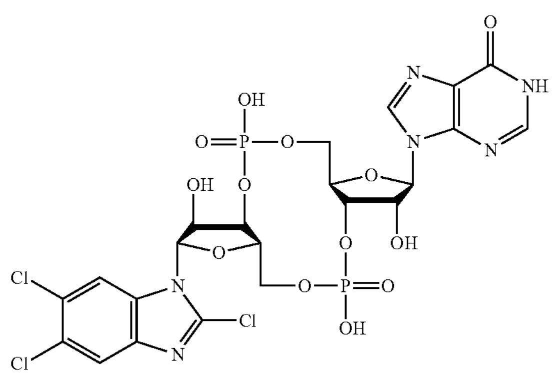 |
| 68 | c[I(2',5')pTClBI(3',5')p] cyclic (inosine-(2' -> 5')-monophosphate-2,5,6-trichlorobenzimidazole riboside-(3' -> 5')-monophosphate) | 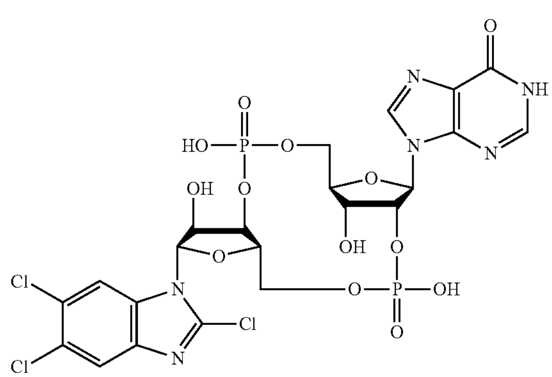 |

TABLE 1-continued

Abbreviations, names and structures of the new, inventive compounds

| # | Compound | Structure |
|---|----------|-----------|
| 69 | c[I(2',5')pTClBI(2',5')p] cyclic (inosine-(2' −> 5')-monophosphate-2,5,6-trichlorobenzimidazole riboside-(2' −> 5')-monophosphate) | 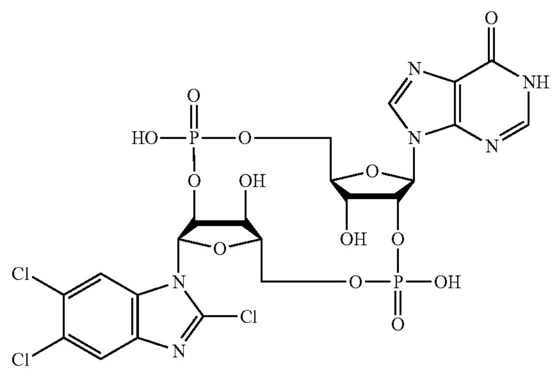 [SMILES: O=c1[nH]cnc2c1ncn2[C@@H]1O[C@@H]2COP(=O)(O)OC3[C@@H](O)[C@@H](COP(=O)(O)O[C@H]1C2O)O[C@H]3n1c(Cl)nc2cc(Cl)c(Cl)cc21] |
| 70 | c[I(3',5')pS-TClBI(3',5')pS] cyclic (inosine-(3' −> 5')-monophosphorothioate-2,5,6-trichlorobenzimidazole riboside-(3' −> 5')-monophosphorothioate) | 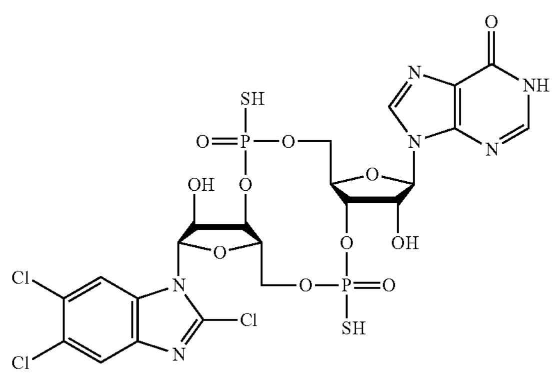 |
| 71 | c[I(2',5')pS-TClBI(3',5')pS] cyclic (inosine-(2' −> 5')-monophosphorothioate-2,5,6-trichlorobenzimidazole riboside-(3' −> 5')-monophosphorothioate) | 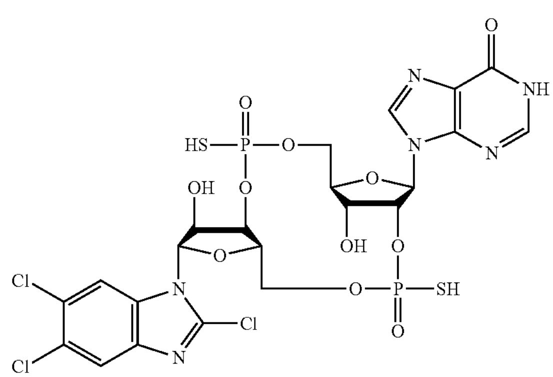 |
| 72 | c[I(2',5')pS-TClBI(2',5')pS] cyclic (inosine-(2' −> 5')-monophosphorothioate-2,5,6-trichlorobenzimidazole riboside-(2' −> 5')-monophosphorothioate) | 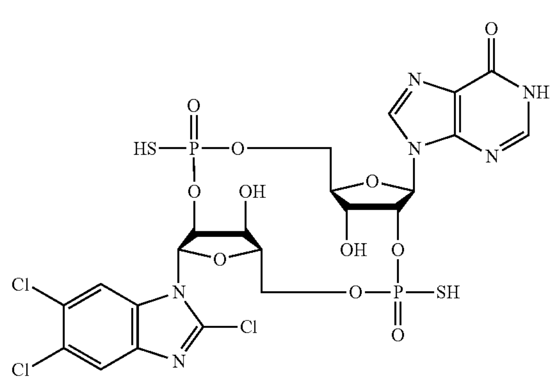 [SMILES: O=c1[nH]cnc2c1ncn2[C@@H]1O[C@@H]2COP(=O)(S)OC3[C@@H](O)[C@@H](COP(=O)(S)O[C@H]1C2O)O[C@H]3n1c(Cl)nc2cc(Cl)c(Cl)cc21] |

TABLE 1-continued

Abbreviations, names and structures of the new, inventive compounds

| # | Compound | Structure |
|---|----------|-----------|
| 73 | c[2'-F-dG(3',5')pBI(3',5')p] cyclic (2'-fluoro-2'-deoxyguanosine-(3' –> 5')-monophosphate-benzimidazole riboside-(3' –> 5')-monophosphate) | 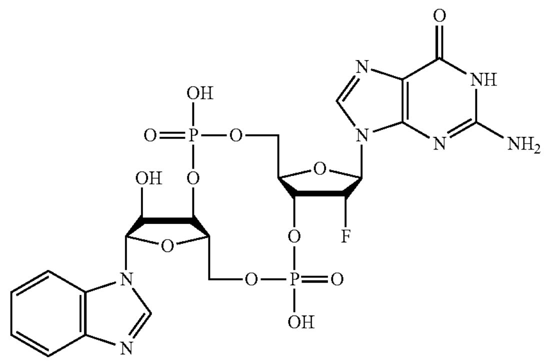 |
| 74 | c[2'-F-dG(3',5')pS-BI(3',5')pS] cyclic (2'-fluoro-2'-deoxyguanosine-(3' –> 5')-monophosphorothioate-benzimidazole riboside-(3' –> 5')-monophosphorothioate) | 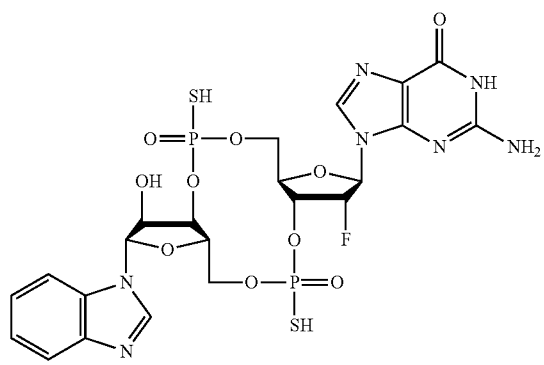 |
| 75 | c[2'-F-dG(3',5')pDClBI(3',5')p] cyclic (2'-fluoro-2'-deoxyguanosine-(3' –> 5')-monophosphate-5,6-dichlorobenzimidazole riboside-(3' –> 5')-monophosphate) | 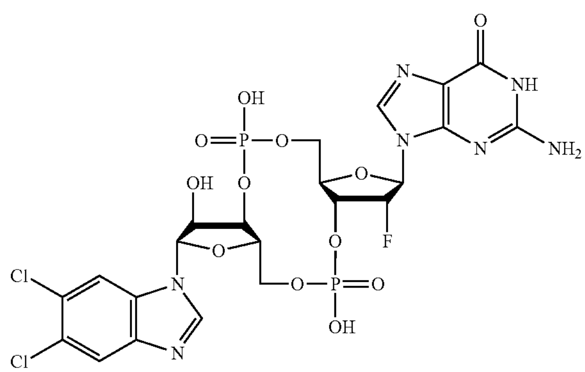 |
| 76 | c[2'-F-dG(3',5')pS-DClBI(3',5')pS] cyclic (2'-fluoro-2'-deoxyguanosine-(3' –> 5')-monophosphate-5,6-dichlorobenzimidazole riboside-(3' –> 5')-monophosphate) | 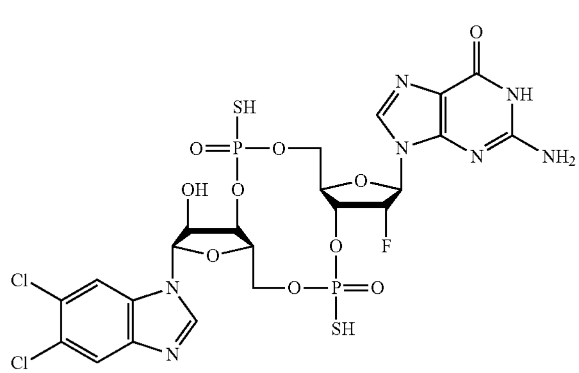 |

TABLE 1-continued

Abbreviations, names and structures of the new, inventive compounds

| # | Compound | Structure |
|---|---|---|
| 77 | c[2'-F-dG(3',5')pTClBI(3',5')p] cyclic (2'-fluoro-2'-deoxyguanosine-(3' -> 5')-monophosphate-2,5,6-trichlorobenzimidazole riboside-(3' -> 5')-monophosphate) | 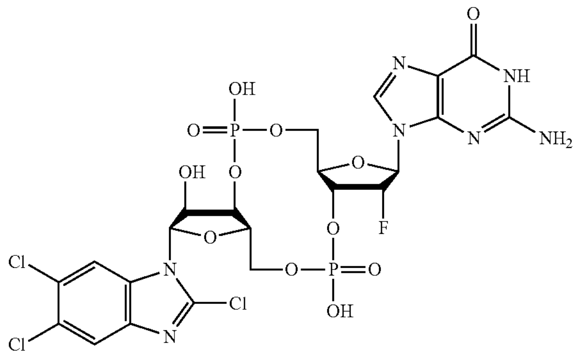 |
| 78 | c[2'-F-dG(3',5')pS-TClBI(3',5')pS] cyclic (2'-fluoro-2'-deoxyguanosine-(3' -> 5')-monophosphorothioate-5,6-dichlorobenzimidazole riboside-(3' -> 5')-monophosphorothioate) | 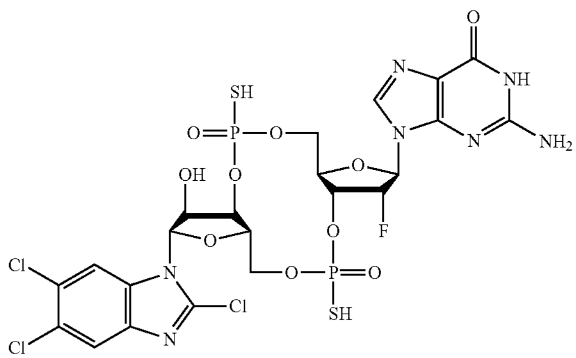 |
| 79 | c[2'-F-dA(3',5')pBI(3',5')p] cyclic (2'-fluoro-2'-deoxyadenosine-(3' -> 5')-monophosphate-benzimidazole riboside-(3' -> 5')-monophosphate) | 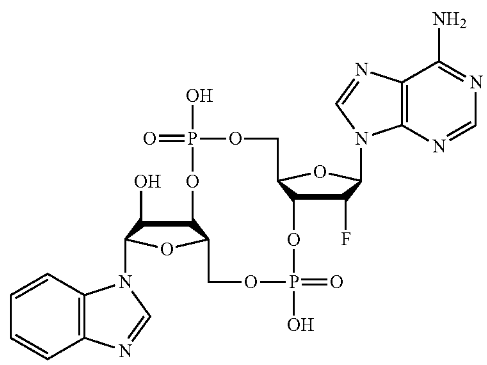 |
| 80 | c[2'-F-dA(3',5')pS-BI(3',5')pS] cyclic (2'-fluoro-2'-deoxyadenosine-(3' -> 5')-monophosphorothioate-benzimidazole riboside-(3' -> 5')-monophosphorothioate) | 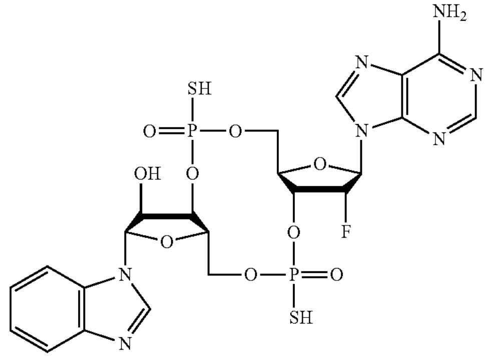 |

TABLE 1-continued

Abbreviations, names and structures of the new, inventive compounds

| # | Compound | Structure |
|---|---|---|
| 81 | c[2'-F-dA(3',5')pDClBI(3',5')p] cyclic (2'-fluoro-2'-deoxyadenosine-(3' -> 5')-monophosphate-5,6-dichlorobenzimidazole riboside-(3' -> 5')-monophosphate) | 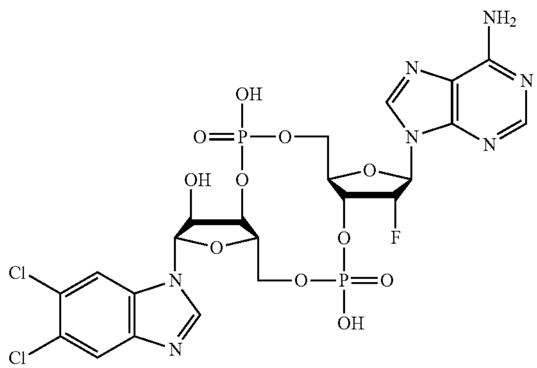 |
| 82 | c[2'-F-dA(3',5')pS-DClBI(3',5')pS] cyclic (2'-fluoro-2'-deoxyadenosine-(3' -> 5')-monophosphorothioate-5,6-dichlorobenzimidazole riboside-(3' -> 5')-monophosphorothioate) | 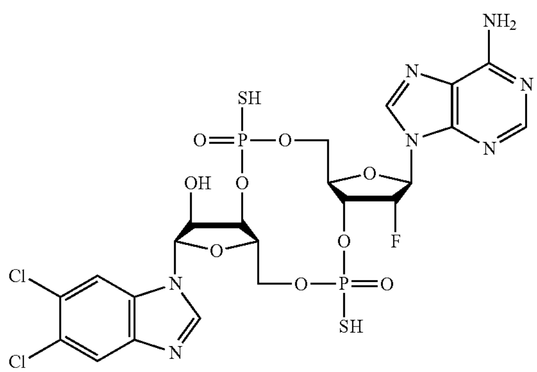 |
| 83 | c[2'-F-dA(3',5')pTClBI(3',5')p] cyclic (2'-fluoro-2'-deoxyadenosine-(3' -> 5')-monophosphate-2,5,6-trichlorobenzimidazole riboside-(3' -> 5')-monophosphate) | 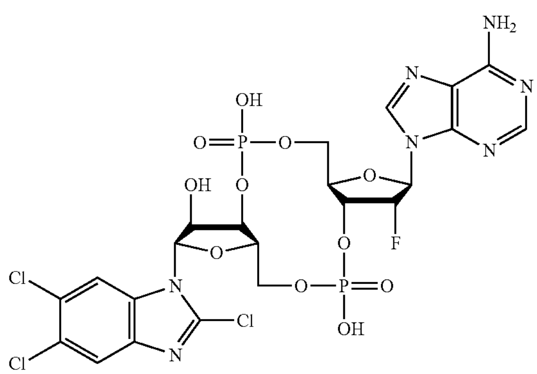 |
| 84 | c[2'-F-dA(3',5')pS-TClBI(3',5')pS] cyclic (2'-fluoro-2'-deoxyadenosine-(3' -> 5')-monophosphorothioate-2,5,6-trichlorobenzimidazole riboside-(3' -> 5')-monophosphorothioate) | 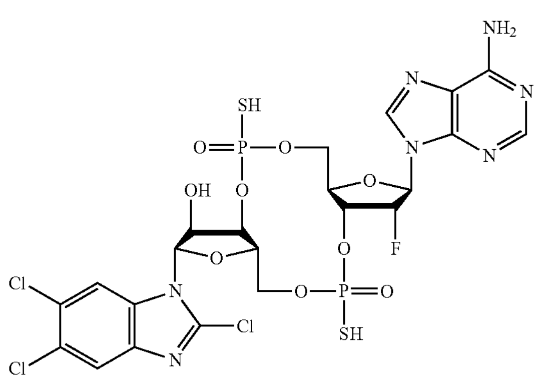 |

TABLE 1-continued

Abbreviations, names and structures of the new, inventive compounds

| # | Compound | Structure |
|---|---|---|
| 85 | c[2'-F-dI(3',5')pBI(3',5')p] cyclic (2'-fluoro-2'-deoxyinosine-(3' –> 5')-monophosphate-benzimidazole riboside-(3' –> 5')-monophosphate) | 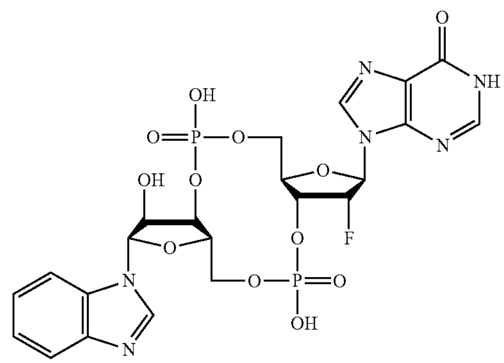 |
| 86 | c[2'-F-dI(3',5')pS-BI(3',5')pS] cyclic (2'-fluoro-2'-deoxyinosine-(3' –> 5')-monophosphorothioate-benzimidazole riboside-(3' –> 5')-monophosphorothioate) | 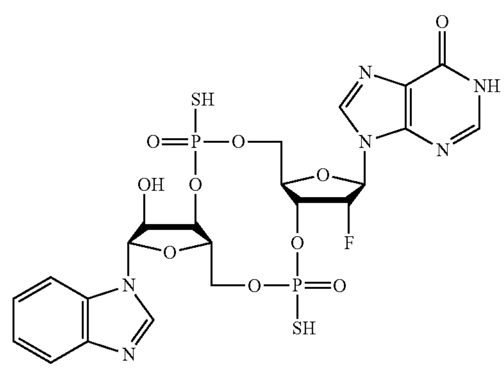 |
| 87 | c[2'-F-dI(3',5')pDClBI(3',5')p] cyclic (2'-fluoro-2'-deoxyinosine-(3' –> 5')-monophosphate-5,6-dichlorobenzimidazole riboside-(3' –> 5')-monophosphate) | 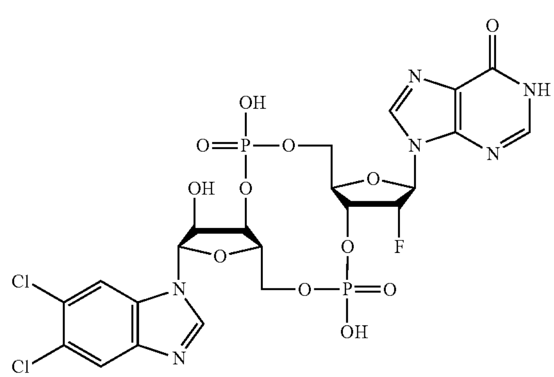 |
| 88 | c[2'-F-dI(3',5')pS-DClBI(3',5')pS] cyclic (2'-fluoro-2'-deoxyinosine-(3' –> 5')-monophosphorothioate-5,6-dichlorobenzimidazole riboside-(3' –> 5')-monophosphorothioate) | 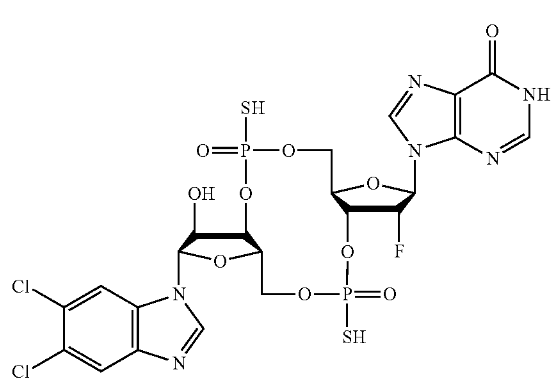 |

TABLE 1-continued

Abbreviations, names and structures of the new, inventive compounds

| # | Compound | Structure |
|---|---|---|
| 89 | c[2'-F-dI(3',5')pTClBI(3',5')p] cyclic (2'-fluoro-2'-deoxyinosine-(3' -> 5')-monophosphate-2,5,6-trichlorobenzimidazole riboside-(3' -> 5')-monophosphate) | 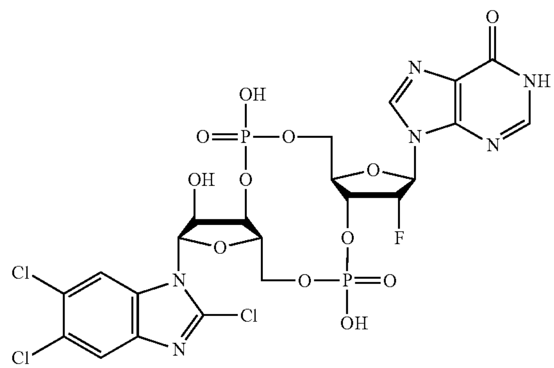 |
| 90 | c[2'-F-dI(3',5')pS-TClBI(3',5')pS] cyclic (2'-fluoro-2'-deoxyinosine-(3' -> 5')-monophosphorothioate-2,5,6-trichlorobenzimidazole riboside-(3' -> 5')-monophosphorothioate) | 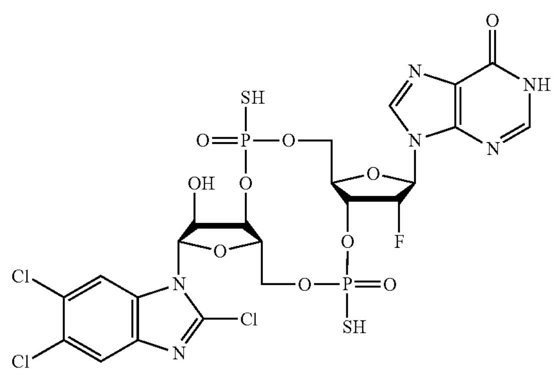 |
| 91 | c[G(3',5')pBI(2',5')p] cyclic (guanosine-(3' -> 5')-monophosphate-benzimidazole riboside-(2' -> 5')-monophosphate) | 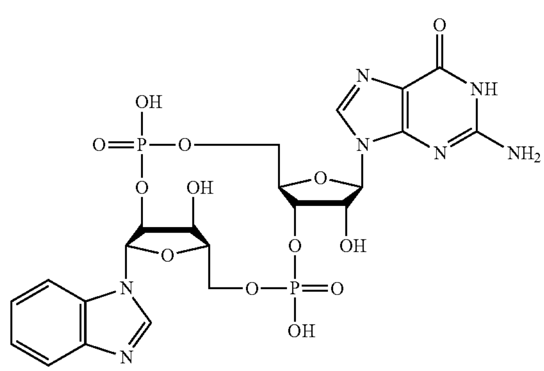 |
| 92 | c[G(3',5')pS-BI(2',5')pS] cyclic (guanosine-(3' -> 5')-monophosphorothioate-benzimidazole riboside-(2' -> 5')-monophosphorothioate) | 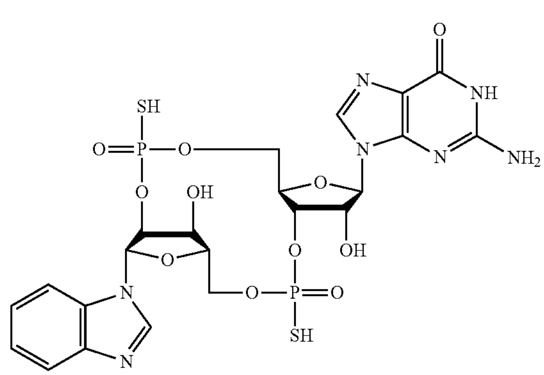 |

TABLE 1-continued

Abbreviations, names and structures of the new, inventive compounds

| # | Compound | Structure |
|---|---|---|
| 93 | c[G(3',5')pDClBI(2',5')p] cyclic (guanosine-(3' -> 5')-monophosphate-5,6-dichlorobenzimidazole riboside-(2' -> 5')-monophosphate) | 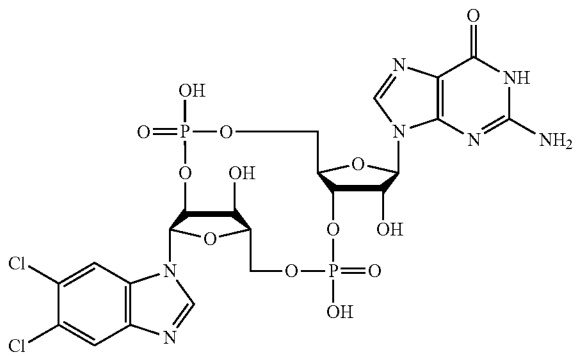 |
| 94 | c[G(3',5')pS-DClBI(2',5')pS] cyclic (guanosine-(3' -> 5')-monophosphorothioate-5,6-dichlorobenzimidazole riboside-(2' -> 5')-monophosphorothioate) | 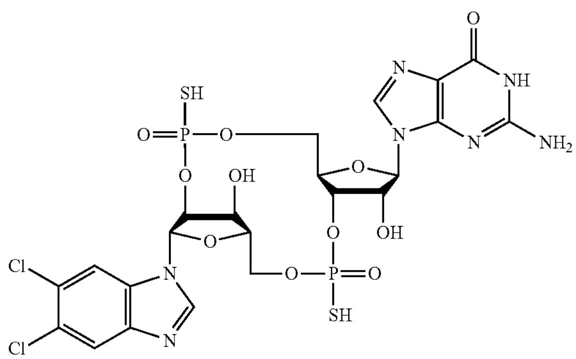 |
| 95 | c[G(3',5')pTClBI(2',5')p] cyclic (guanosine-(3' -> 5')-monophosphate-2,5,6-trichlorobenzimidazole riboside-(2' -> 5')-monophosphate) | 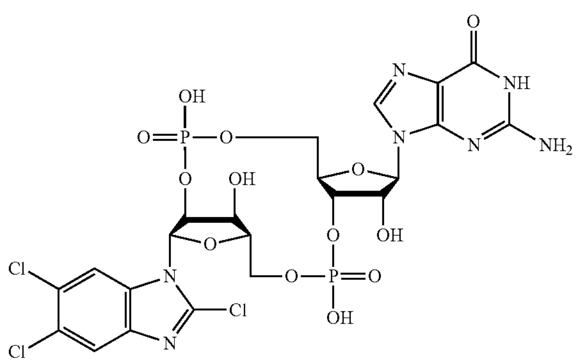 |
| 96 | c[G(3',5')pS-TClBI(2',5')pS] cyclic (guanosine-(3' -> 5')-monophosphorothioate-2,5,6-trichlorobenzimidazole riboside-(2' -> 5')-monophosphorothioate) | 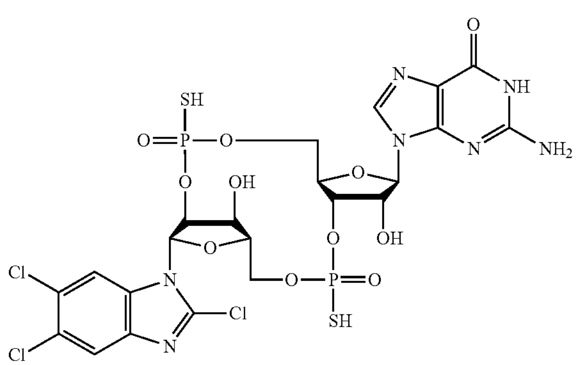 |

TABLE 1-continued

Abbreviations, names and structures of the new, inventive compounds

| # | Compound | Structure |
|---|---|---|
| 97 | c[A(3',5')pBI(2',5')p] cyclic (adenosine-(3' −> 5')-monophosphate-benzimidazole riboside-(2' −> 5')-monophosphate) | 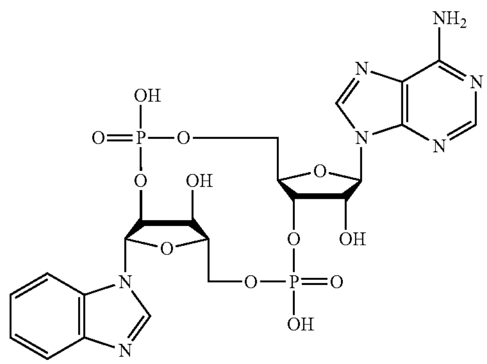 |
| 98 | c[A(3',5')pS-BI(2',5')pS] cyclic (adenosine-(3' −> 5')-monophosphorothioate-benzimidazole riboside-(2' −> 5')-monophosphorothioate) | 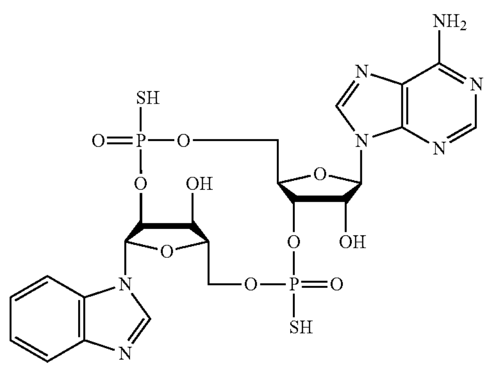 |
| 99 | c[A(3',5')pDClBI(2',5')p] cyclic (adenosine-(3' −> 5')-monophosphate-5,6-dichlorobenzimidazole riboside-(2' −> 5')-monophosphate) | 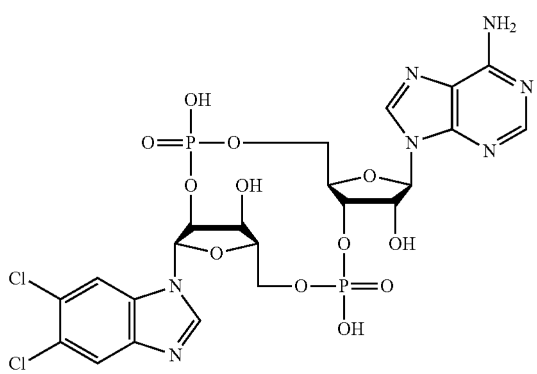 |
| 100 | c[A(3',5')pS-DClBI(2',5')pS] cyclic (adenosine-(3' −> 5')-monophosphorothioate-5,6-dichlorobenzimidazole riboside-(2' −> 5')-monophosphorothioate) | 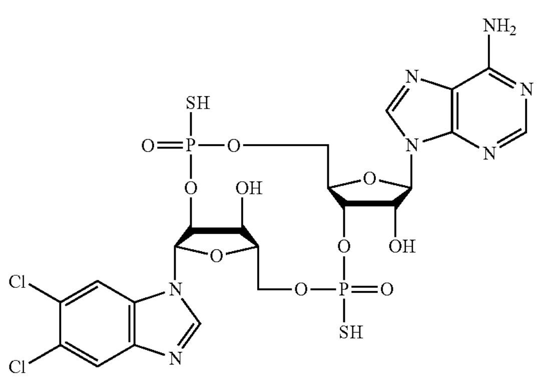 |

TABLE 1-continued

Abbreviations, names and structures of the new, inventive compounds

| # | Compound | Structure |
|---|---|---|
| 101 | c[A(3',5')pTClBI(2',5')p] cyclic (adenosine-(3' −> 5')-monophosphate-2,5,6-trichlorobenzimidazole riboside-(2' −> 5')-monophosphate) | 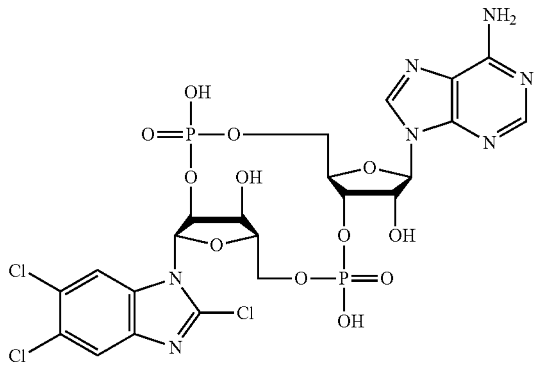 |
| 102 | c[A(3',5')pS-TClBI(2',5')pS] cyclic (adenosine-(3' −> 5')-monophosphorothioate-2,5,6-trichlorobenzimidazole riboside-(2' −> 5')-monophosphorothioate) | 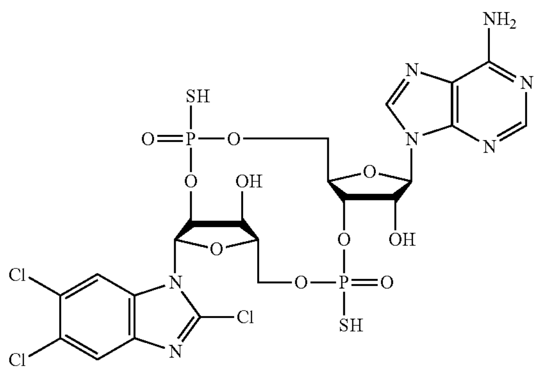 |
| 103 | c[I(3',5')pBI(2',5')p] cyclic (inosine-(3' −> 5')-monophosphate-benzimidazole riboside-(2' −> 5')-monophosphate) | 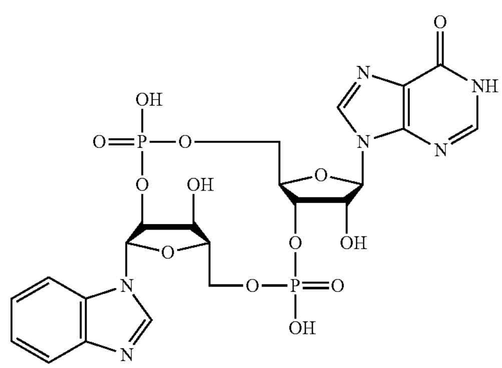 |
| 104 | c[I(3',5')pS-BI(2',5')pS] cyclic (inosine-(3' −> 5')-monophosphorothioate-benzimidazole riboside-(2' −> 5')-monophosphorothioate) | 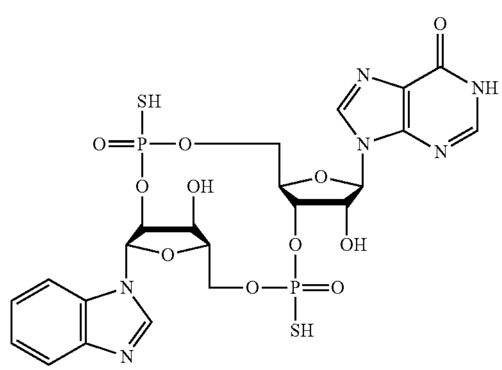 |

TABLE 1-continued

Abbreviations, names and structures of the new, inventive compounds

| # | Compound | Structure |
|---|---|---|
| 105 | c[I(3',5')pDClBI(2',5')p] cyclic (inosine-(3' -> 5')-monophosphate-5,6-dichlorobenzimidazole riboside-(2' -> 5')-monophosphate) | 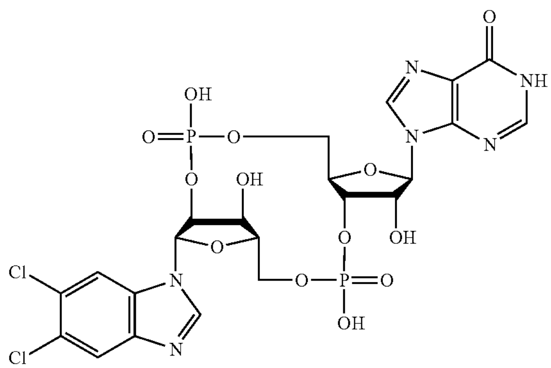 |
| 106 | c[I(3',5')pS-DClBI(2',5')pS] cyclic (inosine-(3' -> 5')-monophosphorothioate-5,6-dichlorobenzimidazole riboside-(2' -> 5')-monophosphorothioate) | 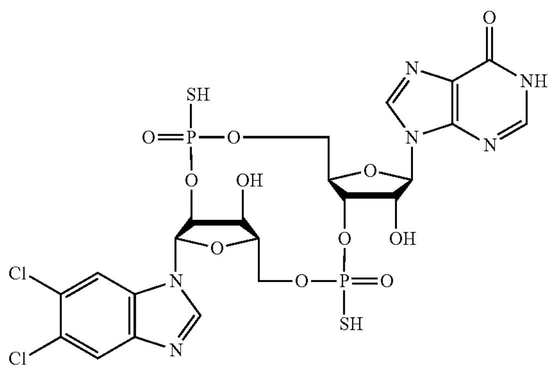 |
| 107 | c[I(3',5')pTClBI(2',5')p] cyclic (inosine-(3' -> 5')-monophosphate-2,5,6-trichlorobenzimidazole riboside-(2' -> 5')-monophosphate) | 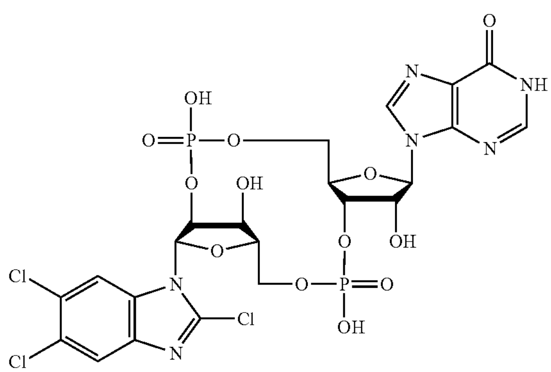 |
| 108 | c[I(3',5')pS-TClBI(2',5')pS] cyclic (inosine-(3' -> 5')-monophosphorothioate-2,5,6-trichlorobenzimidazole riboside-(2' -> 5')-monophosphorothioate) | 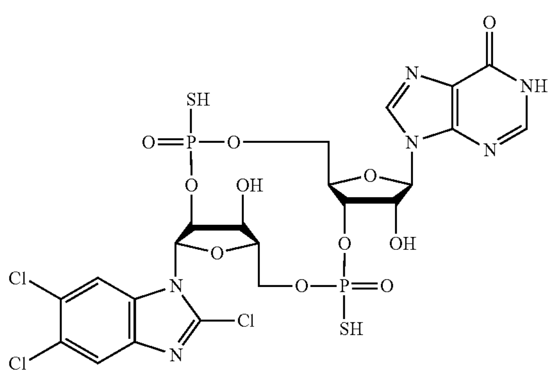 |

TABLE 1-continued

Abbreviations, names and structures of the new, inventive compounds

| # | Compound | Structure |
|---|---|---|
| 109 | c[2'-F-dG(3',5')pBI(2',5')p] cyclic (2'-fluoro-2'-deoxyguanosine-(3' -> 5')-monophosphate-benzimidazole riboside-(2' -> 5')-monophosphate) | 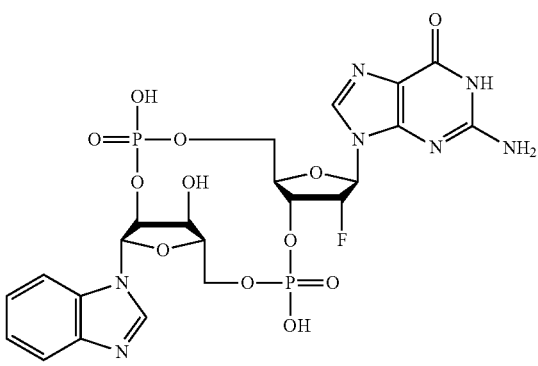 |
| 110 | c[2'-F-dG(3',5')pS-BI(2',5')pS] cyclic (2'-fluoro-2'-deoxyguanosine-(3' -> 5')-monophosphorothioate-benzimidazole riboside-(2' -> 5')-monophosphorothioate) | 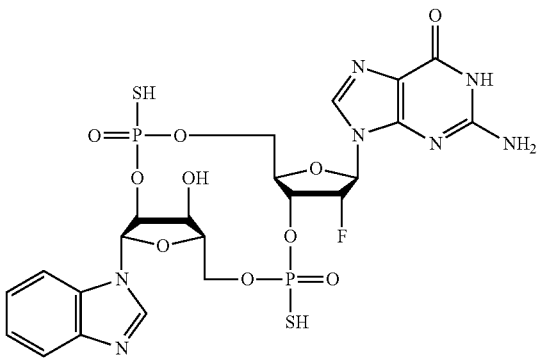 |
| 111 | c[2'-F-dG(3',5')pDClBI(2',5')p] cyclic (2'-fluoro-2'-deoxyguanosine-(3' -> 5')-monophosphate-5,6-dichlorobenzimidazole riboside-(2' -> 5')-monophosphate) | 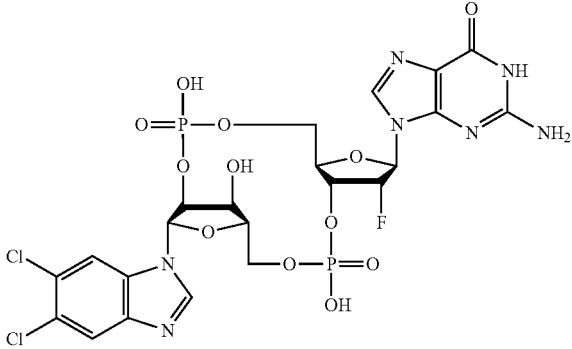 |
| 112 | c[2'-F-dG(3',5')pS-DClBI(2',5')pS] cyclic (2'-fluoro-2'-deoxyguanosine-(3' -> 5')-monophosphate-5,6-dichlorobenzimidazole riboside-(2' -> 5')-monophosphate) | 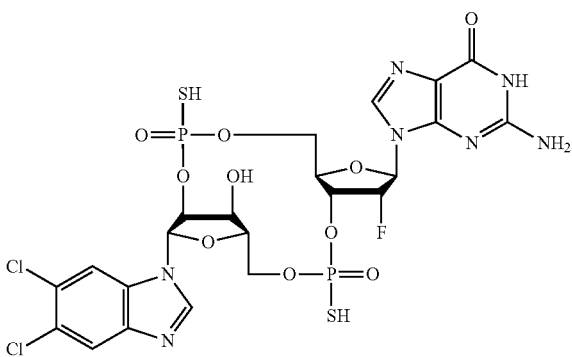 |

TABLE 1-continued

Abbreviations, names and structures of the new, inventive compounds

| # | Compound | Structure |
|---|---|---|
| 113 | c[2'-F-dG(3',5')pTClBI(2',5')p] cyclic (2'-fluoro-2'-deoxyguanosine-(3' -> 5')-monophosphate-2,5,6-trichlorobenzimidazole riboside-(2' -> 5')-monophosphate) | 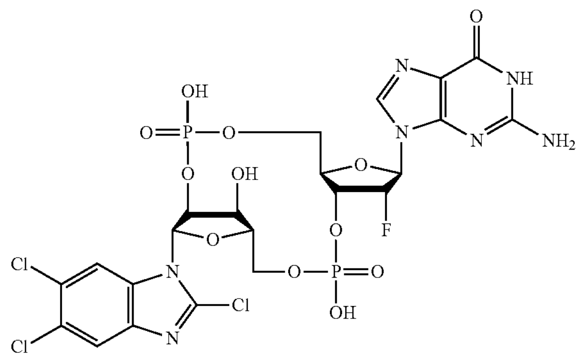 |
| 114 | c[2'-F-dG(3',5')pS-TClBI(2',5')pS] cyclic (2'-fluoro-2'-deoxyguanosine-(3' -> 5')-monophosphorothioate-5,6-dichlorobenzimidazole riboside-(2' -> 5')-monophosphorothioate) | 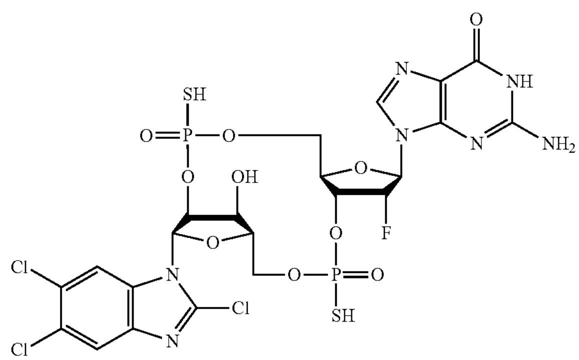 |
| 115 | c[2'-F-dA(3',5')pBI(2',5')p] cyclic (2'-fluoro-2'-deoxyadenosine-(3' -> 5')-monophosphate-benzimidazole riboside-(2' -> 5')-monophosphate) | 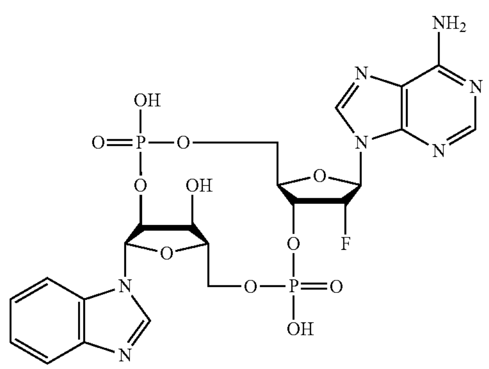 |
| 116 | c[2'-F-dA(3',5')pS-BI(2',5')pS] cyclic (2'-fluoro-2'-deoxyadenosine-(3' -> 5')-monophosphorothioate-benzimidazole riboside-(2' -> 5')-monophosphorothioate) | 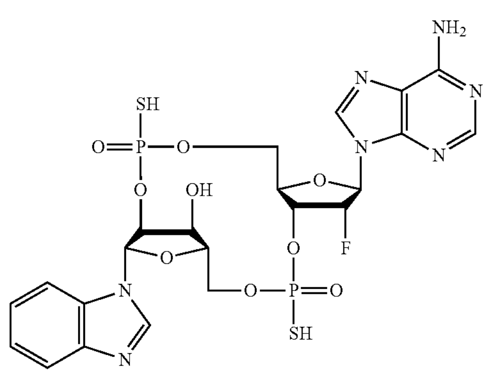 |

TABLE 1-continued

Abbreviations, names and structures of the new, inventive compounds

| # | Compound | Structure |
|---|----------|-----------|
| 117 | c[2'-F-dA(3',5')pDClBI(2',5')p] cyclic (2'-fluoro-2'-deoxyadenosine-(3' -> 5')-monophosphate-5,6-dichlorobenzimidazole riboside-(2' -> 5')-monophosphate) | 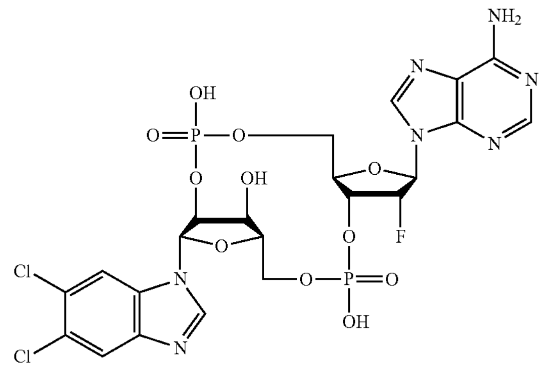 |
| 118 | c[2'-F-dA(3',5')pS-DClBI(2',5')pS] cyclic (2'-fluoro-2'-deoxyadenosine-(3' -> 5')-monophosphorothioate-5,6-dichlorobenzimidazole riboside-(2' -> 5')-monophosphorothioate) | 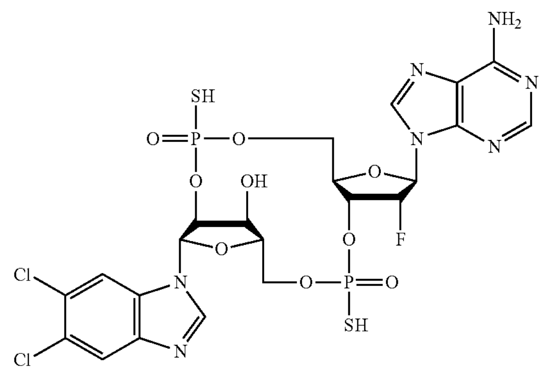 |
| 119 | c[2'-F-dA(3',5')pTClBI(2',5')p] cyclic (2'-fluoro-2'-deoxyadenosine-(3' -> 5')-monophosphate-2,5,6-trichlorobenzimidazole riboside-(2' -> 5')-monophosphate) | 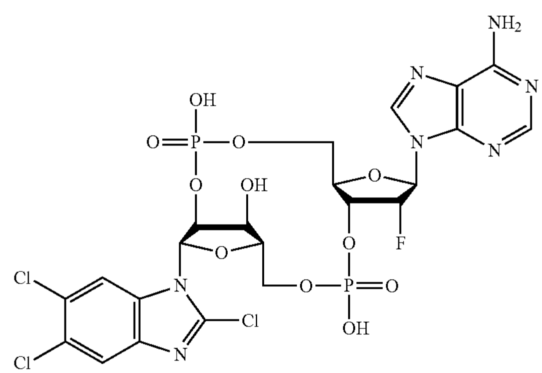 |
| 120 | c[2'-F-dA(3',5')pS-TClBI(2',5')pS] cyclic (2'-fluoro-2'-deoxyadenosine-(3' -> 5')-monophosphorothioate-5,6-trichlorobenzimidazole riboside-(2' -> 5')-monophosphorothioate) | 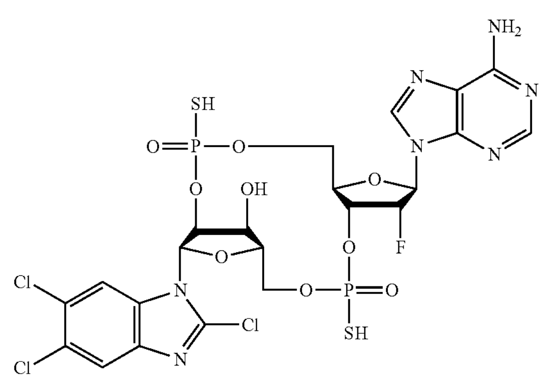 |

TABLE 1-continued

Abbreviations, names and structures of the new, inventive compounds

| # | Compound | Structure |
|---|---|---|
| 121 | c[2'-F-dI(3',5')pBI(2',5')p] cyclic (2'-fluoro-2'-deoxyinosine-(3' -> 5')-monophosphate-benzimidazole riboside-(2' -> 5')-monophosphate) | 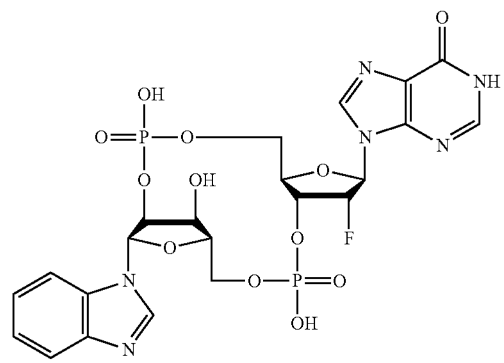 |
| 122 | c[2'-F-dI(3',5')pS-BI(2',5')pS] cyclic (2'-fluoro-2'-deoxyinosine-(3' -> 5')-monophosphorothioate-benzimidazole riboside-(2' -> 5')-monophosphorothioate) | 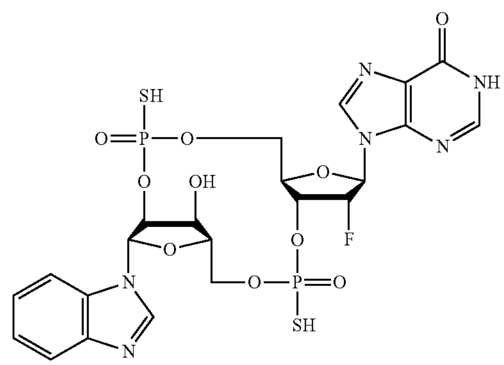 |
| 123 | c[2'-F-dI(3',5')pDClBI(2',5')p] cyclic (2'-fluoro-2'-deoxyinosine-(3' -> 5')-monophosphate-5,6-dichlorobenzimidazole riboside-(2' -> 5')-monophosphate) | 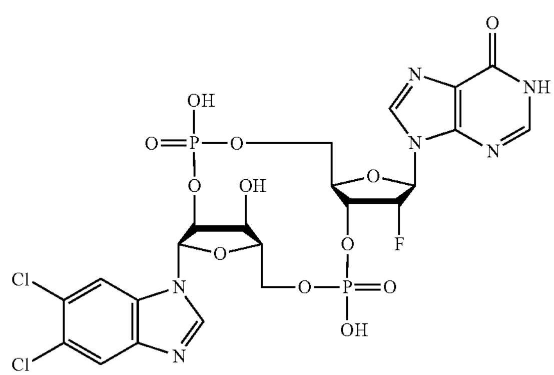 |
| 124 | c[2'-F-dI(3',5')pS-DClBI(2',5')pS] cyclic (2'-fluoro-2'-deoxyinosine-(3' -> 5')-monophosphorothioate-5,6-dichlorobenzimidazole riboside-(2' -> 5')-monophosphorothioate) | 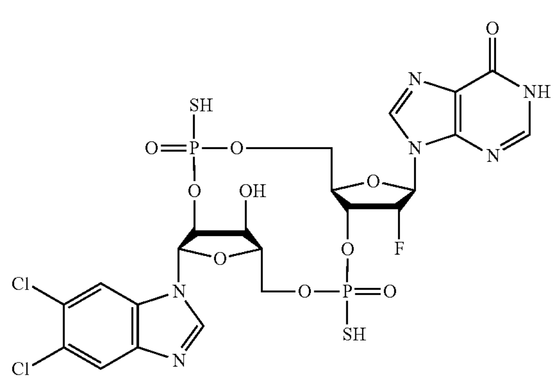 |

TABLE 1-continued

Abbreviations, names and structures of the new, inventive compounds

| # | Compound | Structure |
|---|---|---|
| 125 | c[2'-F-dI(3',5')pTClBI(2',5')p] cyclic (2'-fluoro-2'-deoxyinosine-(3' –> 5')-monophosphate-2,5,6-trichlorobenzimidazole riboside-(2' –> 5')-monophosphate) | 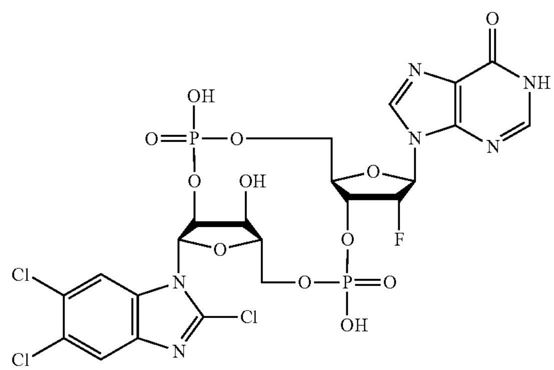 |
| 126 | c[2'-F-dI(3',5')pS-TClBI(2',5')pS] cyclic (2'-fluoro-2'-deoxyinosine-(3' –> 5')-monophosphorothioate-2,5,6-trichlorobenzimidazole riboside-(2' –> 5')-monophosphorothioate) | 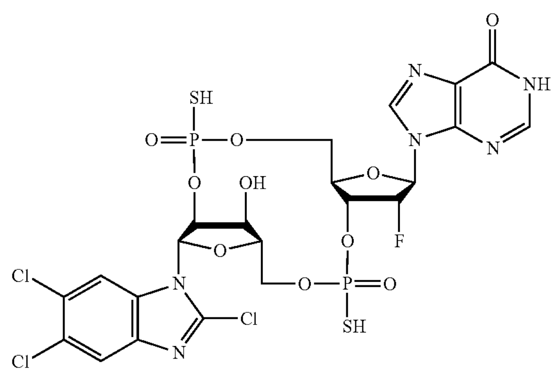 |
| 127 | c[A(3',5')pDMBI(2',5')p] cyclic (adenosine-(3' –> 5')-monophosphate-5,6-dimethylbenzimidazole riboside-(2' –> 5')-monophosphate) | 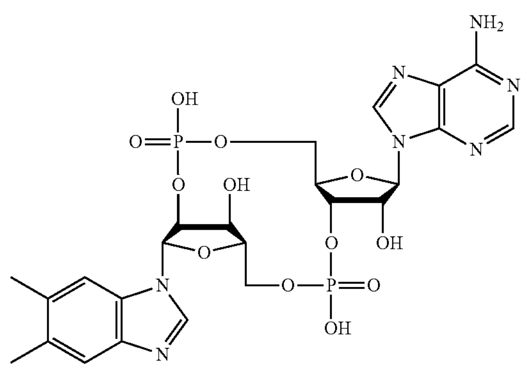 |
| 128 | c[A(3',5')pB-BI(3',5')p] cyclic (adenosine-(3' –> 5')-monoboranophosphate-benzimidazole riboside-(3' –> 5')-monophosphate) | 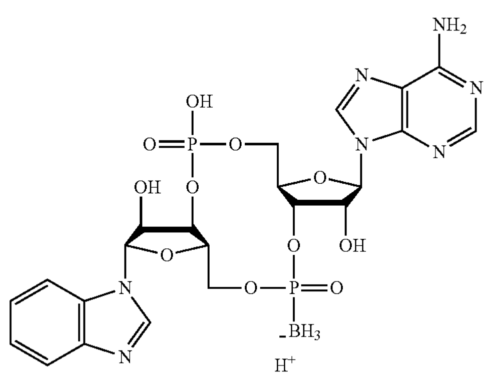 |

TABLE 1-continued

Abbreviations, names and structures of the new, inventive compounds

| # | Compound | Structure |
|---|---|---|
| 129 | c[G(2',5')pB-BI(3',5')p] cyclic (guanosine-(2' -> 5')-monoboranophosphate-benzimidazole riboside-(3' -> 5')-monophosphate) | 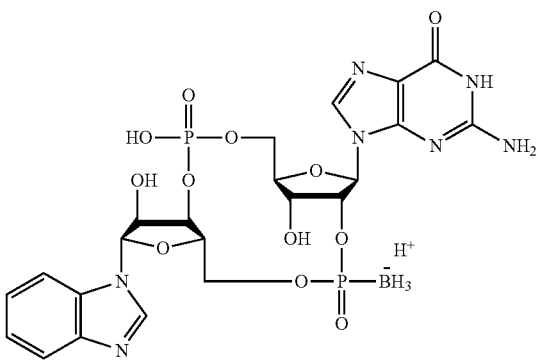 |
| 130 | c[G(2',5')pB-BI(3',5')pS] cyclic (guanosine-(2' -> 5')-monoboranophosphate-benzimidazole riboside-(3' -> 5')-monophosphorothioate) | 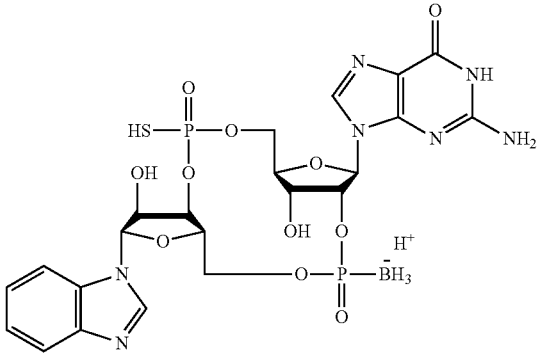 |
| 131 | c[A(2',5')pS-BI(3',5')pB] cyclic (adenosine-(2' -> 5')-monophosphorothioate-benzimidazole riboside-(3' -> 5')-monoboranophosphate) | 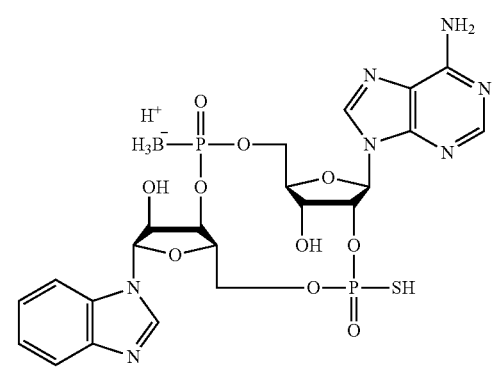 |
| 132 | c[A(3',5')p-BI(2',5')pS] cyclic (adenosine-(3' -> 5')-monophosphate-benzimidazole riboside-(2' -> 5')-monophosphorothioate) | 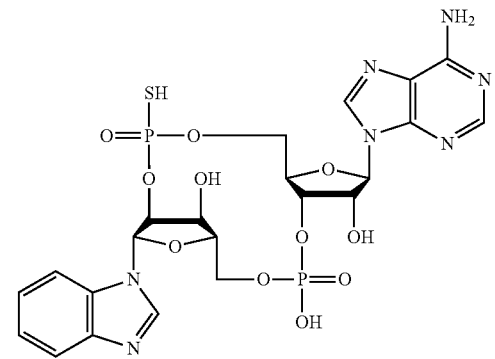 |

TABLE 1-continued

Abbreviations, names and structures of the new, inventive compounds

| # | Compound | Structure |
|---|---|---|
| 133 | c[A(2',5')pB-BI(2',5')p] cyclic (adenosine-(2' –> 5')-monoboranophosphate-benzimidazole riboside-(2' –> 5')-monophosphate) | 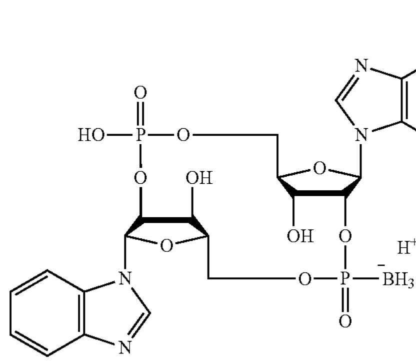 |

As described above, the compounds of this present invention can be labelled according to well-known and established methods.

For example, but not meant as limitation, a fluorescent dye can be coupled to the inventive compounds, in order to determine the intracellular distribution of CDN-binding proteins in living cells by confocal fluorescence microscopy, or to enable fluorescence correlation spectroscopy, fluorescence resonance energy transfer (FRET) studies or determinations of concentration of inventive compounds in living cells.

It should be noted, that hydrates of the inventive compounds are included in the description of the invention as well.

Instead of or in addition to fluorescent dyes the inventive compounds can also labelled with (radioactive) nuclides. Suitable isotopes and corresponding methods of synthesis are established procedures and well-known to those trained in the art.

In addition, the invention comprises polyethylene glycol (PEG)-modified versions of the inventive compounds, which are known to improve solubility in water as well as pharmacokinetic and biodistribution properties.

Further on, the present invention comprises prodrugs of the structures of the Formula (I), wherein the negative charge of the modified or unmodified phosphate group(s) is (are) masked by (a) bio-activatable protecting group(s).

It is well known that these groups increase lipophilicity and hence improve membrane permeability as well as the bioavailability of corresponding parent structures, which normally leads to a 10 to 1000 fold higher potency compared to the parent structure.

Such bio-activatable protecting groups are introduced into the inventive parent compounds according to well-known and established methods of the art.

Preferred examples, but not meant as limitation, are acetoxymethyl, propionyloxymethyl, butyryloxymethyl, pivaloyloxymethyl, acetoxyethyl, acetoxybutyl and acetoxyisobutyl groups.

Preferred examples, but not meant as limitation, for the corresponding residues $R_{10}$ and/or $R_{11}$ within this invention, are acetoxymethyloxy, propionyloxymethyloxy and butyryloxymethyloxy groups.

Preferred examples for more labile protecting groups, but not meant as limitation, comprise alkyl- or aryl-groups as well as substituted alkyl- or aryl-groups.

Further preferred examples for chemically more labile protecting groups for the residues $R_{10}$ and/or $R_{11}$ within this invention, but not meant as limitation, are methyl, ethyl, 2-cyanoethyl, propyl, benzyl, phenyl and polyethylene glycol.

The inventive compounds masked with prodrug groups are itself biologically inactive, but extremely membrane permeant, leading to considerably increased intracellular concentrations.

Enzymatic hydrolysis of the ester bond between the inventive CDN and the prodrug group cleaves off the masking group and finally releases the biologically active parent CDN compound.

In addition, or as an alternative to bio-activatable protecting groups, the present invention comprises photo-activatable protecting groups as well, which are also called "caged" or "photolysable" groups.

These protecting groups can be introduced according to well-known methods established in the art.

In analogy to bio-activatable protection groups photo-activatable protecting groups also mask the negative charge of an unmodified or modified phosphate group and thus increase lipophilicity resulting in much improved membrane permeability and bioavailability.

Preferred, but not limiting examples for photo-activatable protecting groups are o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged) and 6,7-bis(carboxymethoxy)coumarin-4-yl)methyl (BCMCM-caged) groups.

Preferably, the inventive compounds can be immobilised to insoluble supports as well. Preferred examples for such supports are, but not limited to, agarose, dextran, starch and other carbohydrate-based polymers, synthetic polymers such as polyacrylamide, polyethyleneimine, polystyrene, and similar materials, apatite, glass beads, silica gel, gold, graphene, fullerenes, carboranes, titan dioxide, zirconium dioxide, aluminium oxide or to a chip surface that is suitable for binding diverse ligands.

Part of this invention is also a procedure for the chemoenzymatic preparation of an inventive CDN compound with the generic formula $c[N_1(2',5')pN_2(3',5')p]$ or $c[N_1(3',5')pN_2(3',5')p]$ by transglycosylation of c-diAMP, c-diGMP, 2,3-cGAMP or 3',3'-cGAMP with a purine nucleoside phosphorylase (PNPase).

Another aspect of the present invention is a procedure for the chemoenzymatic preparation of a inventive CDN compound with the generic formula c[N$_1$(2',5')pN$_2$(3',5')p], c[N$_1$(2',5')pS-N$_2$(3',5')p], c[N$_1$(2',5')pS-N$_2$(3',5')pS], c[N$_1$(2',5')pB-N$_2$(3',5')p], c[N$_1$(2',5')pB-N$_2$(3',5')pB], c[N$_1$(2',5')pB-N$_2$(3',5')pS] or c[N$_1$(2',5')pS-N$_2$(3',5')pB] by dimerisation and cyclisation of 5'-O-triphosphates, 5'-O-(1-thiotriphosphates) or 5'-O-(1-boranotriphosphates) by means of a cGAMP synthase (cGAS).

Another part of the present invention is a procedure for the chemoenzymatic preparation of a inventive CDN compound with the generic formula c[N$_1$(3',5')pN$_2$(3',5')p], c[N$_1$(3',5')pB-N$_2$(3',5')pB], c[N$_1$(3',5')p-N$_2$(3',5')pB], or c[N$_1$(3',5')pB-N$_2$(3',5')pB], and wherein alternatively the benzimidazole unit in N$_1$ is exchanged for a possibly substituted purine nucleobase, by dimerisation and cyclisation of 5'-O-triphosphates or 5'-O-(1-boranotriphosphates) with an enzyme DNA integrity scanning protein (DisA) from *Bacillus subtilis*.

By this procedure a possibly substituted purine nucleobase can be introduced in position R$_{12}$, according to Formula (I).

The procedures of the invention described above allow for a straightforward access to the novel inventive CDN structures.

Another part of the present invention is the use of one of the new inventive CDNs as a medical drug.

A compound according to Formula (I) can be used in pharmacologically acceptable form for prophylaxis or treatment of a disease, whereby the disease is selected from the group consisting of cancer, infectious diseases of bacterial or viral origin, acute transplant rejection, diabetes mellitus type 1, rheumatoid arthritis, psoriasis, Crohn's disease, restenosis, allergic asthma and other diseases, which can be improved or cured by activation of the STING signal pathway.

A further aspect is that the present invention concerns a method for treatment or prevention of one of the diseases mentioned by administration of a therapeutically or prophylactically effective amount of a compound with the Formula (I) for a person or a patient who needs prophylaxis or treatment.

In a further aspect a compound according to Formula (I) of the present invention can be used as a research reagent, preferentially as research reagent for the study of a disease or disfunction. Therein preferred diseases or disfunctions as fields of application are cancer, infectious diseases of bacterial or viral origin, acute organ transplant rejection, diabetes mellitus type I, rheumatoid arthritis, psoriasis, Crohn's disease, restenosis, allergic asthma, and other diseases, which can be improved or healed by activation of the STING signalling pathway.

The invention is further illustrated by the following figures and examples, which describe preferred embodiments of the invention, but shall, however, not limit it in any way.

EXAMPLES

1 Synthesis
General Experimental Methods

All solvents and reagents used were commercially available, while solvents were of the highest purity available (p.A., HPLC or gradient HPLC grade). Dimethyl sulfoxide (DMSO) was stored with activated molecular sieve two weeks before first use.

Progress of reactions and purity controls of isolated products was performed with reversed phase HPLC (RP-18, ODS-A-YMC, 120-S-11, 250×4 mm, 1.5 ml/min), with UV detection at $\lambda_{max}$ of the corresponding nucleobases. All chromatographic runs were performed at ambient temperature.

The syntheses described were typically performed in a 20-200 μmol scale in 2 ml polypropylene vials with screwed and sealed caps.

Syntheses can be conveniently performed as well in the range of 0.5 μmol 1 mmol in 2 ml polypropylene vials with screwed and sealed caps or in 10 ml to 500 ml round flasks.

Reactions which need a protective gas atmosphere as well as degassing procedures were normally done in 10 or 25 ml round flasks.

Reagents of poor solubility were dissolved by treating the suspensions in an ultrasonic bath or by heating (70° C.); in single cases also suspensions must be used.

Purification of raw products were performed e.g. by preparative medium pressure liquid chromatography (MPLC) (Merck, LiChroprep RP-18, 15-25 μm), preparative anion exchange chromatography (GE Healthcare, Sepharose Q Fast Flow, 45-165 μm) or preparative HPLC (RP-18, ODS-A-YMC, 120-S-11, 250×16 mm, UV 254 nm). Solvent composition depended on the particular substance and was in most cases identical to analytical HPLC conditions. Preparative Flash-chromatography was performed with YMC*gel SIL (6 nm, S-75 μm) silica gel.

As usually performed in nucleotide chemistry the desalting process was achieved either by preparative HPLC (RP-18, ODS-A-YMC, 120-S-11, 250×16 mm, UV 254 nm) or by repeated freeze drying. For freeze-drying the product-containing solutions were frozen at −70° C. for 15 minutes and were evaporated by means of a freeze-drying apparatus or in a vacuum centrifuge.

The evaporation of higher volumes was performed by a rotary evaporator at reduced pressure by means of effective vacuum pumps, which allowed to work in a limited temperature range between 28° C. to 33° C.

Depending on the buffer system used, the isolated products were obtained as triethylammonium salts or sodium salts. Triethylammonium salts can be transferred into the corresponding sodium salts by cation exchange chromatography (GE Healthcare, SP Sepharose™ Fast Flow, 45-165 μm).

Yields were determined by UV spectroscopy at $\lambda_{max}$ according to Lambert-Beer's law using a JASCO V-650 spectrophotometer (JASCO Germany GmbH, Gross-Umstadt, Germany). Unknown extinction coefficients were deducted with respect to literature reports on structurally similar compounds.

Mass spectra were recorded by an Esquire LC 6000 spectrometer (Bruker Daltonic, Bremen, Germany) in ESI-MS modus using a matrix consisting of 50% water/49.5% methanol/0.5% NH$_3$ (pH 9).

NMR spectra were recorded with a 400 MHz Bruker Advance III HD at 300 K. Chemical shifts are given as parts per million (ppm) and $^1$H NMR spectra were calibrated by means of the signal of the residual solvent protons (D$_2$O: δ=4.80 ppm). $^{31}$P-NMR spectra were calibrated by means of the signal for an external reference (85% phosphoric acid, δ=0 ppm) and were recorded proton decoupled.

Determinations of lipophilicity were performed by HPLC according to Krass et al.[7] HPLC equipment consisted of an Elite LaChrom L 2130 pump, an Elite LaChrom L 2455 diode array detector; an Elite LaChrom L 2350 column oven; an Elite LaChrom L 2200 autosampler and Computer EZ Chrom Elite software (all VWR/Hitachi, Darmstadt, Germany).

Gradient 1: Stationary phase: Polygosil 60-10, RP-18; 250×4 mm (Macherey & Nagel, DOren, Germany). Mobile phase A: 10 ml 1 M triethylammonium phosphate buffer (TEAP), pH 6.5+990 ml methanol. Mobile phase B: 10 ml 1 M TEAP, pH 6.5+990 ml H$_2$O. Time program: 0 min: 100% B; 60 min: 100% A; 65 min: 100% A; 70 min: 100% B; 90 min: 100% B. Flow rate: 1.0 ml/min.

Gradient 2: Stationary phase: RP-18, ODS-A-YMC, 120-S-11, 250×4 mm. Mobile phase A: 10 ml 1 M triethylammonium formate buffer (TEAF), pH 6.8+990 ml acetonitrile. Mobile phase B: 10 ml 1 M TEAF, pH 6.8+990 ml H$_2$O. Time program: 0 min: 100% B; 60 min: 60% A; 65 min: 60% A; 70 min: 100% B; 90 min: 100% B. Flow rate: 1.0 ml/min.

General Synthetic Procedure A:

Transglycosylation by Purine-Nucleoside-Phosphorylases (PNPase)

PNPase normally cleaves off the nucleobase from ribo- and deoxyribo-purine nucleosides and is used here to exchange the nucleobases of the natural CDNs (c-diGMP, c-diAMP, 2',3'-cGAMP, 3%3-cGAMP) against other, unnatural bases (transglycosylation), resulting in some of the inventive compounds. This strategy takes advantage of the higher stability of the glycosidic bond towards benzimidazole and its analogues compared to the natural purine nucleobases.

Typically, c-diGMP (Biolog GmbH, Bremen, Germany) and one of the free benzimidazole bases, as defined in claim 1, are incubated in buffered aqueous solution with purine nucleoside phosphorylase.

Variants of the enzyme are commercially available from Sigma-Aldrich and according to this invention can be used in homogenous solution, or preferentially but not limited to, immobilised to natural supports such as dextran, agarose, cellulose or immobilised to supports of synthetic origin, such as acrylamide, polystyrene, etc.

Alternatively, and especially if the specificity of the commercial PNPases do not accept special benzimidazole analogues, PNPases from lower organisms are preferred.

Many benzimidazole analoga have poor solubility in water. In this case, the benzimidazole analogue is enriched in the solution by heating and ultrasonic treatment and used as a suspension.

Preferred is the addition of solubilisers such as DMSO, DMF or tensides in a concentration that do not unduly disturb the enzymatic reaction. Due to the high thermostability of PNPases the reaction is performed in the preferred temperature range of 30° C.-60° C. anyhow.

In a preferred embodiment of the invention the enzymatic reaction is performed in 0.01 M-1 M TRIS-HCl buffer within a pH range of 6-10 in presence of 1-15% glycerol and 0.0001 M-0.1 M dithiothreitol (DTT) at 20° C.-50° C.

In an especially preferred embodiment of the invention the enzymatic reaction is performed in 20 mM TRIS-HCl buffer in a pH range of 6.5-8.5 and 0.001 M DTT at 37° C.

Example 1: Synthesis of Cyclic (guanosine-(3'→5')-monophosphate-benzimidazole riboside-(3'→5')-monophosphate (c[G(3',5')pBI(3',5')p]), and Cyclic (Benzimidazole riboside-(3'→monophosphate-benzimidazole riboside-(3'→5')-monophosphate) (c[BI(3',5')pBI(3',5')p])

11.8 mg/100 µmol of benzimidazole are suspended in 1 ml Tris-HCl buffer (20 mM, pH 8.0, 10% glycerol). After addition of 50 µl DMSO the closed reaction vials are heated to 70° C. in a water bath and are subsequently sonicated in an ultrasonic bath for some minutes. 2 mg of DTT are added, followed by 10 µmol of c-diGMP (sodium salt) and 50 units of PNPase and the mixture is shaken at 37° C. in a thermomixer. During the reaction regularly probes are taken and analysed by HPLC. After completion of the reaction the solution with the raw product is filtrated and is purified by semipreparative HPLC using a reversed phase silica (RP-18) and triethylammonium formate buffer. At first residual c-diGMP and guanine elute, later c[G(3',5')pBI(3',5')p] and subsequently c[BI(3',5')pBI(3',5')p] can be isolated. Excess benzimidazole is removed during regeneration of the column. Both products are received as triethylammonium salts. Typical yields depend on the actual condition of the enzyme and are between 15 and 45% for the symmetrical product with two benzimidazole units and between 7 and 16% for the asymmetric mixed product.

| c[G(3',5')pBI(3',5')p]: 3',5'/3',5' | c[BI(3',5')pBI(3',5')p]: 3',5'/3',5' |
|---|---|
| C$_{22}$H$_{25}$N$_7$O$_{12}$P$_2$; MW 641.43 (free acid) | C$_{24}$H$_{26}$N$_4$O$_{12}$P$_2$; MW 624.44 (free acid) |
| UV: $\lambda_{max}$: ~250 nm | UV: $\lambda_{max}$: 245 nm, ε 9810 |
| ESI-MS (+): m/z 743 [M + TEA + H]$^+$ | ESI-MS (+): m/z 726 [M + TEA + H]$^+$ |
| ESI-MS (−): m/z 640 [M − H]$^-$ | ESI-MS (−): m/z 623 [M − H]$^-$ |

Example 2: Synthesis of Cyclic (adenosine-(3'→5')-monophosphate-5,6-dimethylbenzimidazole riboside-(2'→5')-monophosphate (c[A(3',5')pDMBI(2',5')p])

15 mg/100 µmol of 5,6-dimethylbenzimidazole are suspended in 1 ml Tris-HCl buffer (20 mM, pH 8.0, 10% glycerol). After addition of 50 µl DMSO the closed reaction vial is heated to 70° C. in a water bath and is subsequently sonicated in an ultrasonic bath for some minutes. 2 mg of DTT are added, followed by 10 µmol of 2',3'-c-GAMP (sodium salt) and 50 units of PNPase and the mixture is shaken at 37° C. in a thermomixer. During the reaction regularly probes are taken and analysed by HPLC. After completion of the reaction the solution with the raw product is filtrated and is purified by semipreparative HPLC using a reversed phase silica (RP-18) and triethylammonium formate buffer. At first residual 2',3'-cGAMP and guanine elute, and with significantly increased retention time c[A(3',5')pDMBI(2',5')p] is isolated. Excess 5,6-dimethylbenzimidazole is removed during regeneration of the column. The product is obtained as triethylammonium salt.

Typical yields depend on the actual condition of the enzyme and lie between 15 and 45%.

c[A(3',5')pDMBI(2',5')p]: 3',5'/2',5'
C$_{24}$H$_{29}$N$_7$O$_{12}$P$_2$; MW 669.48 (free acid)
UV: $\lambda_{max}$: ~270 nm
ESI-MS (+): m/z 771 [M + TEA + H]$^+$
ESI-MS (−): m/z 668 [M − H]$^-$ General Synthetic Procedure B:

Catalytic Dimerisation and Cyclisation of Nucleoside-5'-Monophosphates Activated nucleoside-5'-monophosphates can dimerise, polymerise and even cyclise in presence of clay materials and the occurrence of different species depends on the reaction conditions chosen. This reaction yields both, 2',5' as well as 3',5'-connected adducts.

Example 3: Synthesis of Cyclic (5,6-dichlorobenzimidazole riboside-(2'→monophosphate-5,6-dichlorobenzimidazole riboside-(3' 5')-monophosphate) (c[DCIBI(2',5')pDCIBI(3',5')p]) and Cyclic (5,6-dichlorobenzimidazole riboside-(3' 5')-monophosphate-5,6-dichlorobenzimidazole riboside-(3' 5')-monophosphate) (c[DCIBI(3',5')PDCIBI(3',5')p])

The synthesis follows a protocol of Urata et al.[1], describing the reaction of imidazole-activated adenosine-5'-O-monophosphate.

100 mg of 5,6-dichlorobenzimidazole-5'-O-monophosphate imidazolide (Biolog GmbH, Bremen) are dissolved in 10 ml of a buffer, containing 0.2 M NaCl, 75 mM $MgCl_2$ and 0.1 M HEPES. After addition of 50 mg montmorillonite ($Na^+$-form) the pH is adjusted to 8.0 with NaOH or HCl and the solution is kept at ambient temperature.

The progress of the reaction is monitored with reversed phase HPLC. After completion of the reaction the mixture is filtrated, gently concentrated by means of an rotary evaporator and purified with preparative HPLC. The cyclic reaction products are isolated and freeze-dried as triethylammonium salts.

Typical yields for the 2'→5'/3'→5'-connected products are approximately 5% and 35% for the 3'→5'/3'→5'-connected structures, respectively.

In a particularly preferred embodiment of the invention the enzymatic synthesis is performed in a buffer containing 0.1 M ethanolamine, 0.025 M magnesium chloride and 0.001 M DTT of pH 9.5 at 37° C.

Example 4: Immobilisation of DisA to NHS-Activated Sepharose 4 Fast Flow

About 5 ml of NHS-activated Sepharose 4 Fast Flow slurry (GE Healthcare; #17-0906-01) were washed according to manufacturer's protocol, dispensed from washing water in the last step by using a glass sinter frit and immediately transferred in a 3.5 ml polypropylene reaction vial (PP) with screw cap and seal (Sarstedt), containing a ready-to-work solution consisting of 0.5 ml DisA preparation (15.5 mg/ml DisA (by UV $A_{280\ nm}$) in 50 mM HEPES buffer, pH 7.5, 200 mM NaCl and 10% glycerol), 0.4 ml 50 mM HEPES buffer, pH 7.5, 200 mM NaCl, 10% glycerol and 0.1 ml 1 M $NaH_2PO_4$, pH 7.5. The vial was shaken for 5 min at ambient temperature and additional 16 h at 4° C.

Subsequently, the immobilised enzyme was washed with 30 ml of 30 mM $NaH_2PO_4$, pH 7 and then stored as a slurry (volume ~3 ml) in 30 mM $NaH_2PO_4$, pH 7 containing 1% $NaN_3$ at 4° C.

Before starting the chemoenzymatic reactions the storing buffer was changed to 0.1 M ethanolamine, 0.025 M mag-

| c[DCIBI(2',5')pDCIBI(3',5')p]: 2',5'/3',5' | c[DCIBI(3',5')pDCIBI(3',5')p]: 3',5'/3',5' |
|---|---|
| $C_{24}H_{22}Cl_4N_4O_{12}P_2$; MW 762.22 (free acid) | $C_{24}H_{22}Cl_4N_4O_{12}P_2$; MW 762.22 (free acid) |
| UV: $\lambda_{max}$: ~254 nm, ε 11500 | UV: $\lambda_{max}$: 254 nm, ε 11500 |
| ESI-MS (+): m/z 862/864/866 [M + TEA + H]$^+$ | ESI-MS (+): m/z 862/864/866 [M + TEA + H]$^+$ |
| ESI-MS (−): m/z 759 [M − H]$^−$ | ESI-MS (−): m/z 759 [M − H]$^−$ |

General Synthetic Procedure C:

Chemoenzymatic Dimerisation and Cyclisation of Nucleoside-5'-O-triphosphates with DisA for the Production of Benzimidazole-Containing CDNs The DNA integrity scanning protein DisA from *Bacillus subtilis*[2], which biocatalyses the formation of c-diAMP from ATP in *Bacillus subtilis*, was used to convert purine-based nucleoside triphosphates with modifications in the purine bases as well as in the ribose part to the corresponding CDNs. The same enzyme is used to synthesise the benzimidazole-containing CDNs of the present invention.

The chemoenzymatic reactions can either be performed with the free enzyme in homogenous solution or preferentially with DisA that is immobilised to supports of natural origin such as dextran, agarose, cellulose or that is immobilised to synthetic supports such as acrylamide, polystyrene and others.

In an especially preferred embodiment the chemoenzymatic reaction is performed with DisA, that is immobilised to Sepharose 4 Fast Flow (GE Healthcare).

The enzyme is active within a temperature range of 15° C.-50° C. and a wide pH range of pH 5-pH 11 and in buffered or non-buffered solutions in the presence of divalent metal salts and reducing agents.

Buffers can be chosen from collections suitable for biological applications and proteins, which are well known to scientists of the art.

In a preferred embodiment of the invention the enzymatic synthesis is performed in a buffer containing 0.01 M-1 M alkyl ammonium ions, 0.01 M-1 M magnesium chloride and 0.0001 M-0.1 M dithiothreitol (DTT) of a pH in the range of 7-10 at 20° C.-40° C.

nesium chloride, 0.001 M DTT, pH 9.5 (reaction buffer). The amount needed was taken from the well shaken slurry, transferred into a 2 ml PP reaction vial and centrifuged at 300 rpm in a laboratory centrifuge (Biofuge primo, Heraeus). The supernatant was removed, the remaining Sepharose with the enzyme was suspended with 1 ml reaction buffer and centrifuged again at 300 rpm. This procedure was repeated twice. Finally, 2.5 ml DisA-Sepharose slurry in 0.1 M ethanolamine buffer, 0.025 M magnesium chloride, 0.001 M DTT, pH 9.5 were received.

Example 5: Chemoenzymatic Synthesis of Cyclic (2'-fluoro-2'-deoxyadenosine-(3'→5')-monophosphate-2'-fluoro-2'-deoxyadenosine-(3'→5')-monophosphate) (2',2"-Di-F-c-didAMP)

To 100 μl of DisA-Sepharose slurry (as described in Example 4) 0.5 μmol of 2-fluoro-2-deoxyadenosine-5'-O-triphosphate (BIOLOG GmbH, Bremen) in 0.1 M ethanolamine buffer, 0.025 M magnesium chloride, 0.001 M DTT were added and kept at pH 9.5/37° C. for 26 h until complete conversion (>94% product).

| 2'-2"-Di-F-c-didAMP: 3',5'/3',5' |
|---|
| $C_{20}H_{22}F_2N_{10}O_{10}P_2$; MW 662.4 (free acid) |
| UV: $\lambda_{max}$: 259 nm, ε 27000 |
| ESI-MS (+): m/z 663 [M + H]$^+$ |
| ESI-MS (−): m/z 661 [M − H]$^−$ |

Example 6: Chemoenzymatic Synthesis of Cyclic (N⁶-benzyladenosine-(3'→5')-monophosphate-N⁶-benzyladenosine-(3'→5')-monophosphate) (6,6'-Di-Bn-c-diAMP)

To 100 µl of DisA-Sepharose slurry (as described in Example 4) 0.5 µmol of $N^6$-benzyladenosine-5'-O-triphosphate (BIOLOG GmbH, Bremen) in 0.1 M ethanolamine buffer, 0.025 M magnesium chloride, 0.001 M DTT were added and kept at pH 9.5/37° C. for 30 min until complete conversion (>95% product).

6,6'-Di-Bn-c-diAMP: 3',5'/3',5'
$C_{34}H_{36}N_{10}O_{12}P_2$; MW 838.7 (free acid)
UV: $\lambda_{max}$: 268 nm, ε 36900
ESI-MS (+): m/z 839 [M + H]⁺
ESI-MS (−): m/z 837 [M − H]⁻

Example 7: Chemoenzymatic Synthesis of Cyclic (adenosine-(3'→5')-monophosphate-adenosine-(3'→5')-monophosphate) (c-diAMP), cyclic (adenosine-(3'→5')-monophosphate-8-chloroadenosine-(3'→5')-monophosphate) (8-Cl-c-diAMP) and cyclic (8-chloroadenosine-(3'→5')-monophosphate-8-chloroadenosine-(3'→5')-monophosphate) (8,8'-Di-Cl-c-diAMP)

To 100 µl of DisA-Sepharose slurry (as described in Example 4) 0.5 µmol of adenosine-5'-O-triphosphate and 0.5 µmol of 8-chloroadenosine-5'-O-triphosphate (BIOLOG GmbH, Bremen) in 0.1 M ethanolamine buffer, 0.025 M magnesium chloride, 0.001 M DTT were added and kept at pH 9.5/37° C. for 3 days until complete conversion (>93% product; ~21% c-diAMP, ~51.5% 8-Cl-c-diAMP, ~21.5% 8,8'-Di-Cl-c-diAMP).

c-diAMP: 3',5'/3',5'
$C_{20}H_{24}N_{10}O_{12}P_2$; MW 658.4 (free acid)
UV: $\lambda_{max}$: 259 nm, ε 27000
ESI-MS (+): m/z 659 [M + H]⁺
ESI-MS (−): m/z 657 [M − H]⁻
8,8'-Di-Cl-c-diAMP: 3',5'/3',5'
$C_{20}H_{22}Cl_2N_{10}O_{12}P_2$; MW 727.3 (free acid)
UV: $\lambda_{max}$: 262 nm, ε 30600
ESI-MS (+): m/z 727 [M + H]⁺
ESI-MS (−): m/z 725 [M − H]⁻

8-Cl-c-diAMP: 3',5'/3',5'
$C_{20}H_{23}ClN_{10}O_{12}P_2$; MW 692.9 (free acid)
UV: $\lambda_{max}$: 262 nm, ε 28600
ESI-MS (+): m/z 693 [M + H]⁺
ESI-MS (−): m/z 691 [M − H]⁻

Example 8: Chemoenzymatic Synthesis of Cyclic (2-chloroadenosine-(3'→5')-monophosphate-2-chloroadenosine-(3'→5')-monophosphate) (2,2'-Di-Cl-c-diAMP)

To 100 µl of DisA-Sepharose slurry (as described in Example 4) 0.5 µmol of 2-chloroadenosine-5'-O-triphosphate in 0.1 M ethanolamine buffer, 0.025 M magnesium chloride, 0.001 M DTT were added and kept at pH 9.5/37° C. until reaction is completed (20 h, 93% product formation).

2,2'-Di-Cl-c-diAMP: 3',5'/3',5'
$C_{20}H_{22}Cl_2N_{10}O_{12}P_2$; MW 727.3 (free acid)
UV: $\lambda_{max}$: 262 nm, ε 25750
ESI-MS (+): m/z 727 [M + H]⁺
ESI-MS (−): m/z 725 [M − H]⁻

Example 9: Chemoenzymatic Synthesis of Cyclic (7-deazaadenosine-(3'→5')-monophosphate-7-deazaadenosine-(3'→5')-monophosphate) (7,7-Di-CH-c-diAMP)

To 100 µl of DisA-Sepharose slurry (as described in Example 4) 0.5 µmol of 7-deazaadenosine-5'-O-triphosphate in 0.1 M ethanolamine buffer, 0.025 M magnesium chloride, 0.001 M DTT were added and kept at pH 9.5/37° C. for 3 days (>99% product formation).

7,7'-Di-CH-c-diAMP: 3',5'/3',5'
$C_{22}H_{26}N_8O_{12}P_2$; MW 656.4 (free acid)
UV: $\lambda_{max}$: 269 nm, ε 21600
ESI-MS (+): m/z 657 [M + H]⁺
ESI-MS (−): m/z 655 [M − H]⁻

Example 10: Chemoenzymatic Synthesis of Cyclic (adenosine-(3'→5')-monophosphate-adenosine-(3'→5')-monophosphate) (c-diAMP), cyclic (adenosine-(3'→5')-monophosphate-benzimidazole riboside-(3'→5')-monophosphate) (c[A(3',5')pBI(3',5')p]) and cyclic (benzimidazole riboside-(3'→5')-monophosphate-benzimidazole riboside-(3'→5')-monophosphate) (c[BI(3',5')pBI(3',5')p])

To 25 ml of DisA-Sepharose slurry (as described in Example 4) 50 µmol of adenosine-5'-O-triphosphate and 100 µmol of benzimidazole riboside-5'-O-triphosphate (BIOLOG GmbH, Bremen) in 0.1 M ethanolamine buffer, 0.025 M magnesium chloride, 0.001 M DTT were added and kept at pH 9.5/30-37° C. for 3 days (>75% product formation).

c[A(3',5')pBI(3',5')p]: 3',5'/3',5'
$C_{22}H_{25}N_7O_{12}P_2$; MW 641.4 (free acid)
UV: $\lambda_{max}$: 254 nm, ε 16150
ESI-MS (+): m/z 642 [M + H]⁺
ESI-MS (−): m/z 640 [M − H]⁻
c-diAMP: 3',5'/3',5'
$C_{20}H_{24}N_{10}O_{12}P_2$; MW 658.4 (free acid)
UV: $\lambda_{max}$: 259 nm, ε 27000
ESI-MS (+): m/z 659 [M + H]⁺
ESI-MS (−): m/z 657 [M − H]⁻ c[BI(3',5')pBI(3',5')p]: 3',5'/3',5'
$C_{24}H_{26}N_4O_{12}P_2$;
MW 624.4 (free acid)
UV: $\lambda_{max}$: 245 nm, ε 9810
ESI-MS (+): m/z 625 [M + H]⁺
ESI-MS (−): m/z 623 [M − H]⁻

Example 11: Chemoenzymatic Synthesis of Cyclic (2'-fluoro-2'-deoxyadenosine-(3'→5')-monophosphate-2'-fluoro-2'-deoxyadenosine-(3'→5')-monophosphate) (2'-2'''-Di-F-c-didAMP), cyclic (2'-fluoro-2'-deoxyadenosine-(3'→5')-monophosphate-benzimidazole riboside-(3'→5')-monophosphate) (c[2'-F-dA(3',5')pBI(3',5')p]) and cyclic (benzimidazole riboside-(3'→5')-monophosphate-benzimidazole riboside-(3'→5')-monophosphate) (c[B(3',5')pBI(3',5')p])

To 25 ml of DisA-Sepharose slurry (as described in Example 4) 50 of μmol 2-fluoro-2-deoxyadenosine-5'-O-triphosphate and 50 μmol of benzimidazole riboside-5'-O-triphosphate (BIOLOG GmbH, Bremen) in 12 ml of 0.1 M ethanolamine buffer, 0.025 M magnesium chloride, 0.001 M DTT were added and kept at pH 9/30-37° C. for 43 hours (>75% product formation).

2'-2'''-Di-F-c-didAMP: 3',5'/3',5'
$C_{20}H_{22}F_2O_{10}P_2$;
MW 662.4 (free acid)
UV: $\lambda_{max}$: 259 nm, ε 27000
ESI-MS (+): m/z 663 [M + H]$^+$
ESI-MS (−): m/z 661 [M − H]$^-$
c[BI(3',5')pBI(3',5')p]: 3',5'/3',5'
$C_{24}H_{26}N_4O_{12}P_2$;
MW 624.4 (free acid)
UV: $\lambda_{max}$: 245 nm, ε 9810
ESI-MS (+): m/z 625 [M + H]$^+$
ESI-MS (−): m/z 623 [M − H]$^{--}$ c[2'-F-dA(3',5')pBI(3',5')p]: 3',5'/3',5'
$C_{22}H_{24}FN_7O_{11}P_2$;
MW 643.4 (free acid)
UV: $\lambda_{max}$: 254 nm, ε 16150
ESI-MS (+): m/z 644 [M + H]$^+$
ESI-MS (−): m/z 642 [M − H]$^-$

Example 12: Chemoenzymatic Synthesis of Cyclic (adenosine-(3'→5')-monoboranophosphate-adenosine-(3'→5')-monoboranophosphate) (c-diAMPBB), Cyclic (adenosine-(3'→5')-monoboranophosphate-benzimidazole riboside-(3'→5')-monophosphate) (c[A(3',5')pB-BI(3',510) and cyclic (benzimidazole riboside-(3'→5')-monophosphate-benzimidazole riboside-(3'→5')-monophosphate) (031(3',5')pBI(3',5')p])

To 100 μl of DisA-Sepharose slurry (as described in Example 4) 0.5 μmol of adenosine-5'-O-(1-boranotriphosphate) and 0.5 μmol benzimidazole riboside-5'-O-triphosphate (BIOLOG GmbH, Bremen) in 0.1 M ethanolamine buffer, 0.025 M magnesium chloride, 0.001 M DTT are added and kept at pH 9.5/37° C. for 3 days (>75% product formation).

c-diAMPBB: 3',5'/3',5'
$C_{20}H_{30}B_2N_{10}O_{10}P_2$;
MW 654.1 (free acid)
UV: $\lambda_{max}$: 259 nm, ε 27000
ESI-MS (+): m/z 655 [M + H]$^+$
ESI-MS (−): m/z 653 [M − H]$^-$
c[BI(3',5')pBI(3',5')p]: 3',5'/3',5'
$C_{24}H_{26}N_4O_{12}P_2$;
MW 624.4 (free acid)
UV: $\lambda_{max}$: 245 nm, ε 9810
ESI-MS (+): m/z 625 [M + H]$^+$
ESI-MS (−): m/z 623 [M − H]$^{--}$ c[A(3',5')pB-BI(3',5')p]: 3',5'/3',5'
$C_{22}H_{28}BN_7O_{11}P_2$;
MW 639.3 (free acid)
UV: $\lambda_{max}$: ~254 nm
ESI-MS (+): m/z 640 [M + H]$^+$
ESI-MS (−): m/z 638 [M − H]$^-$

Example 12a: Chemoenzymatic Synthesis of Cyclic (benzimidazole riboside-(3'→5')-monophosphate-benzimidazole riboside-(3'→5')-monophosphate) (c[BI(3',5')pBI(3',5')p])

To 21 ml of DisA-Sepharose slurry (as described in Example 4) 400 μmol of benzimidazole riboside-5'-O-triphosphate (BIOLOG GmbH, Bremen) in 35 ml of 0.1 M ethanolamine buffer, 0.025 M magnesium chloride, 0.001 M DTT were added and kept at pH 9.5 at 30-37° C. for 14 days (>55% product formation).

c[BI(3',5')pBI(3',5')p]: 3',5'/3',5'
$C_{24}H_{26}N_4O_{12}P_2$; MW 624.4 (free acid)
UV: $\lambda_{max}$: 245 nm, ε 9810
ESI-MS (+): m/z 625 [M + H]$^+$
ESI-MS (−): m/z 623 [M − H]$^{--}$

Example 12b: Chemoenzymatic Synthesis of Cyclic (5,6-dichlorobenzimidazole riboside-(3'→5')-monophosphate-5,6-dichlorobenzimidazole riboside-(3'→5')-monophosphate) (c[DCIBI(3',5')pDCIBI(3',5')p])

To 4.5 ml of DisA-Sepharose slurry (as described in Example 4) 160 μmol of 5,6-dichlorobenzimidazole riboside-5'-O-triphosphate (BIOLOG GmbH, Bremen) in 50 ml of 0.1 M ethanolamine buffer, 0.025 M magnesium chloride, 0.001 M DTT were added and kept at pH 9.5 at 30-37° C. for 6 days (~50% product formation).

c[DCIBI(3',5')pDCIBI(3',5')p]: 3',5'/3',5'
$C_{24}H_{22}Cl_4N_4O_{12}P_2$; MW 762.22 (free acid)
UV: $\lambda_{max}$: 254 nm, ε 11500
ESI-MS (+): m/z 761/763/765 [M + H]$^+$
ESI-MS (−): m/z 759/761/763 [M − H]$^-$

Example 12c: Chemoenzymatic Synthesis of Cyclic (2'-fluoro-2'-deoxyadenosine-(3'→5')-monophosphate-2'-fluoro-2'-deoxyadenosine-(3'→5')-monophosphate) (2'-2'''-Di-F-c-didAMP), cyclic (2'-fluoro-2'-deoxyadenosine-(3'→5')-monophosphate-5,6-dichlorobenzimidazole riboside-(3'→5')-monophosphate) (c[2'-F-dA(3',5')pDCIBI(3',5')p]) and cyclic (5,6-dichlorobenzimidazole riboside-(3'→5')-monophosphate-5,6-dichlorobenzimidazole riboside-(3'→5')-monophosphate) (c[DCIBI(3',5')pDCIBI(3',5')p])

To 25 ml of DisA-Sepharose slurry (as described in Example 4) 100 μmol of 2-fluoro-2-deoxyadenosine-5'-O-triphosphate and 100 μmol of 5,6-dichlorobenzimidazole riboside-5'-O-triphosphate (BIOLOG GmbH, Bremen) in 50 ml of 0.1 M ethanolamine buffer, 0.025 M magnesium chloride, 0.001 M DTT were added and kept at pH 9.5 at 30-37° C. within 3 days (~70% product formation).

2'-2'''-Di-F-c-didAMP: 3',5'/3',5'
$C_{20}H_{22}F_2N_{10}O_{10}P_2$; MW 662.4 (free acid)

c[2'-F-dA(3',5')pDCIBI(3',5')p]: 3',5'/3',5'
$C_{22}H_{22}Cl_2FN_7O_{11}P_2$; MW 712.3 (free acid)

-continued

UV: $\lambda_{max}$: 259 nm, ε 27000
ESI-MS (+): m/z 663 [M + H]$^+$
ESI-MS (−): m/z 661 [M − H]$^-$
c[DClBI(3',5')pDClBI(3',5')p]: 3',5'/3',5'
$C_{24}H_{22}Cl_4N_4O_{12}P_2$; MW 762.22 (free acid)
UV: $\lambda_{max}$: 254 nm, ε 11500
ESI-MS (+): m/z 761/763/765 [M + H]$^+$
ESI-MS (−): m/z 759/761/763 [M − H]$^-$ UV: $\lambda_{max}$: 260 nm, ε 19050
ESI-MS (+): m/z 712/714 [M + H]$^+$
ESI-MS (−): m/z 710/712 [M − H]$^-$ Example 12d: Chemoenzymatic Synthesis of Cyclic (adenosine-(3'→5')-monophosphate-adenosine-(3'→5')-monophosphate) (c-diAMP), cyclic (adenosine-(3'→5')-monophosphate-5,6-dichlorobenzimidazole riboside-(3'→5')-monophosphate) (c[A(3',5')PDClBI(3',5')p]) and cyclic (5,6-dichlorobenzimidazole riboside-(3'→5')-monophosphate-5,6-dichlorobenzimidazole riboside-(3'→5')-monophosphate) (c[DClBI(3',5')pDClBI(3',5')p])

To 20 ml of DisA-Sepharose slurry (as described in Example 4) 200 μmol of adenosine-5'-O-triphosphate and 100 μmol of 5,6-dichlorobenzimidazole riboside-5'-O-triphosphate (BIOLOG GmbH, Bremen) in 50 ml 0.1 M ethanolamine buffer, 0.025 M magnesium chloride, 0.001 M DTT were added and kept at pH 9.5 at 30-37° C. within 2 days (>75% product formation).

c-diAMP: 3',5'/3',5'
$C_{20}H_{24}N_{10}O_{12}P_2$; MW 658.4 (free acid)
UV: $\lambda_{max}$: 259 nm, ε 27000
ESI-MS (+): m/z 659 [M + H]$^+$
ESI-MS (−): m/z 657 [M − H]$^-$
c[DClBI(3',5')pDClBI(3',5')p]: 3',5'/3',5'
$C_{24}H_{22}Cl_4N_4O_{12}P_2$; MW 762.22 (free acid)
UV: $\lambda_{max}$: 254 nm, ε 11500
ESI-MS (+): m/z 761/763/765 [M + H]$^+$
ESI-MS (−): m/z 759/761/763 [M − H]$^-$ c[A(3',5')pDClBI(3',5')p]: 3',5'/3',5'
$C_{22}H_{23}Cl_2N_7O_{12}P_2$; MW 710.3 (free acid)
UV: $\lambda_{max}$: 260 nm, ε 19050
ESI-MS (+): m/z 710/712 [M + H]$^+$
ESI-MS (−): m/z 708/710 [M − H]$^-$ Example 12e: Chemoenzymatic Synthesis of Cyclic (2'-fluoro-2'-deoxyinosine-(3'→5')-monophosphate-benzimidazole riboside-(3'→5')-monophosphate) (c[2'-F-dI(3',5')pBI(3',5')p])

5.5 μmol of (c[2-F-dA(3',5')pBI(3',5')p]) from Example 11 were treated with adenosine monophosphate deaminase (Deamyzyme 5000, Amano Enzyme Europe Ltd, Great Britain) according to a published procedure[8] within 2 days to yield c[2-F-dI(3',5')pBI(3',5')p] quantitatively.

c[2'-F-dI(3',5')pBI(3',5')p]: 3',5'/3',5'
$C_{22}H_{23}FN_7O_{12}P_2$; MW 644.4 (free acid)
UV: $\lambda_{max}$: 247 nm, ε 17000
ESI-MS (+): m/z 645 [M + H]$^+$
ESI-MS (−): m/z 643 [M − H]$^-$ General Synthetic Procedure D:

Chemoenzymatic Dimerisation and Cyclisation of Nucleoside-5'-O-triphosphates with cGAS for the Production of Benzimidazole-Containing CDNs The enzyme cGAMP synthase (cGAS) is able to produce biocatalytically the non-canonical 2',3'-cGAMP from GTP and ATP in presence of double stranded DNA. It is not highly specific and it could be shown, that the chemoenzymatic synthesis of mono- and diphosphorothioate-containing CDNs is possible with this enzyme[3].

The same enzyme (recombinantly expressed from mouse) is used to produce the benzimidazole-containing CDNs of the present invention.

The chemoenzymatic reactions can be performed either in homogeneous solution or, preferred, with the enzyme immobilised to natural supports such as dextran, agarose, cellulose or immobilised to synthetic materials such as acrylamide, polystyrene and others.

The enzyme is active at temperatures ranging from 15° C.-50° C. within a broad pH range from pH 5-pH 11 in buffered or unbuffered solution, in presence of bivalent metal salts, double stranded DNA and reductive agents.

Suitable buffers are buffer systems which are widely used for proteins and other biological applications and which are well known to those skilled in the art.

In a preferred embodiment of the invention the enzymatic reaction is performed in 0.01 M-1M buffer systems within a pH range of 7-10 with 0.005 M-1 M magnesium chloride, 0.01 mg/ml-1 mg/ml herring sperm DNA and 0.0001 M-0.1 M dithiothreitol (DTT) at 20°-40° C.

In an especially preferred embodiment of the invention the enzymatic reaction is performed in a buffer solution containing 0.02 M TRIS-HCl, 0.02 M magnesium chloride, 0.1 mg/ml herring sperm DNA, 0.001 M DTT at a pH of 8 at 37° C.

Example 13: Chemoenzymatic Synthesis of Cyclic (guanosine-(2'→5')-monoboranophosphate-benzimidazole riboside-(3'→5')-monophosphate) (c[G(2',5')pB-BI(3',5')p])

1 μmol guanosine-5'-O-(1-boranotriphosphate) and 1 μmol benzimidazole riboside-5'-O-triphosphate (BIOLOG GmbH, Bremen) are treated with 10 μM cGAS (mouse, amino acids 147-507) in 0.002 M TRIS-HCl, 0.02 M magnesium chloride, 0.1 mg/ml herring sperm DNA, 0.001 M DTT, pH 8 in 1 ml end volume at 37° C. within 3 days (>75% product formation).

c[G(2',5')pB-BI(3',5')p]: 2',5'/3',5'
$C_{22}H_{28}BN_7O_{12}P_2$; MW 655.3 (free acid)

UV: $\lambda_{max}$: ~250 nm,
ESI-MS (+): m/z 656 [M + H]$^+$
ESI-MS (−): m/z 654 [M − H]$^-$ c[G(2',5')pB-BI(3',5')pS]: 2',5'/3',5'
$C_{22}H_{28}BN_7O_{11}P_2S$; MW 671.3 (free acid)
UV: $\lambda_{max}$: ~250 nm,
ESI-MS (+): m/z 672 [M + H]$^+$
ESI-MS (−): m/z 670 [M − H]$^-$ Example 14: Chemoenzymatic Synthesis of Cyclic (guanosine-(2'→5')-monoboranophosphate-benzimidazole riboside-(3'→5')-monophosphorothioate) (c[G(2',5')pB-BI(3',5')pS])

10 µM of cGAS (mouse, amino acids 147-507), 1 µmol of guanosine-5'-O-(1-boranotriphosphate) and 1 µmol of benzimidazole riboside-5'-O-(1-thiotriphosphate) (BIOLOG GmbH, Bremen) are incubated in 0.002 M TRIS-HCl, 0.02 M magnesium chloride, 0.1 mg/ml herring sperm DNA, 0.001 M DTT, pH 8 in 1 ml final volume for 3 days at 37° C. (>75% product formation).

General Synthetic Procedure E:

Chemical Synthesis Method for the Production of Benzimidazole-Containing CDNs

The chemical synthesis of the benzimidazole-containing CDNs described in the present invention is based on work published by Gaffney et al. 2010[4] and Gao et al. 2013[5].

Example 15: Chemical Synthesis of Cyclic (adenosine-(3'→5')-monophosphate-benzimidazole riboside-(3'→5')-monophosphate) (c[A(3',5')p-BI(3',5')p])

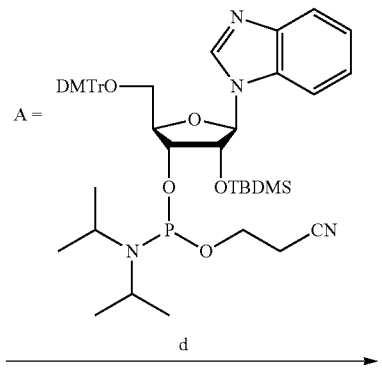

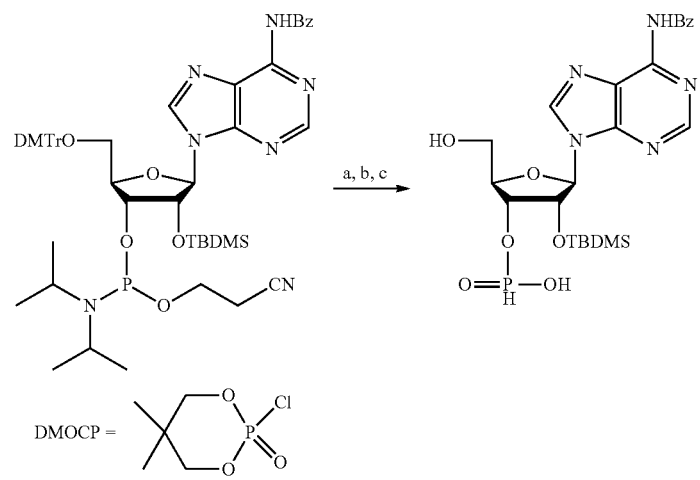

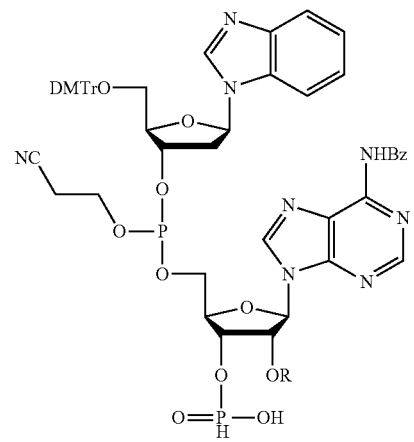

R = TBDMS

↓ e, f

-continued

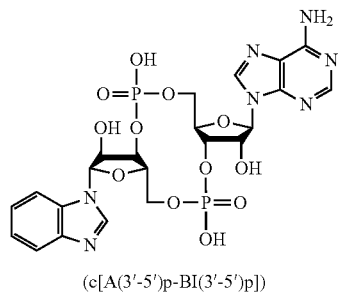

(c[A(3'-5')p-BI(3'-5')p])

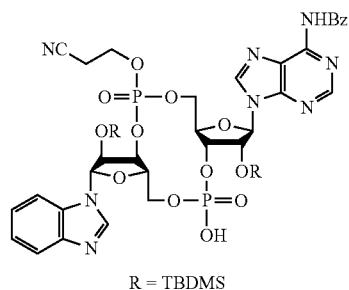

R = TBDMS

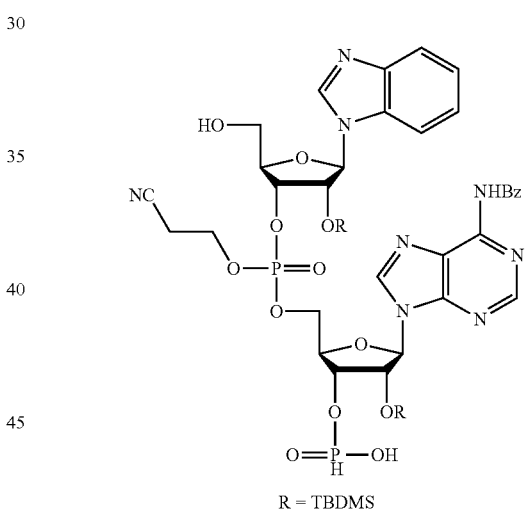

R = TBDMS

Synthesis 1:

Synthesis of Cyclic (adenosine-(3'→5')-monophosphate-benzimidazole riboside-(3'→5')-monophosphate) (c[A(3',5') p-BI(3',5')p]). Synthetic steps: a) pyridinium trifluoroacetate/$H_2O$; b) tert.-butylamine; c) dichloroacetic acid/$H_2O$; d) A, pyridine; e) tert.-butylhydroperoxide; f) dichloroacetic acid/$H_2O$; g) 2-chloro-5,5-dimethyl-1,3,2-dioxaphosphorinane-2-oxide; h) iodine, $H_2O$; I) methylamine/ethanol; j) triethylamine trihydrofluoride.

Example 15a: Synthesis of the H-phosphonate Intermediate 5'-OH-2'-TBDMS-3'-H-phosphonate-$N^6$-Bz-adenosine

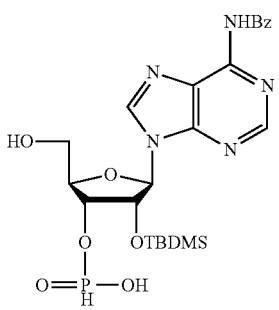

The phosphoramidite 5'-DMTr-2'-TBDMS-3'-CEP-adenosine (Chemgenes Inc., USA) is dissolved in dry acetonitrile. 2 equivalents of water as well as 1.2 equivalents of pyridinium trifluoroacetate are added and the mixture is stirred for 15 min at room temperature. Subsequently, the volatile components are removed by evaporation under reduced pressure. 100 equivalents of tert.-butylamine are added, the resulting solution is stirred for 30 min at room temperature and subsequently is evaporated again under reduced pressure. The residue is dissolved in acetonitrile and is evaporated at reduced pressure another time. The resulting residue is dissolved in dichloromethane and 10 equivalents of water are added. 9 Equivalents of dichloroacetic acid, prepared from a 3% solution of dichloroacetic acid in dichloromethane, are added and the solution is stirred for 10 min at room temperature. Afterwards, 18 equivalents of pyridine is added and the solution is stirred for 10 min at room temperature.

Analysis of the raw product by LC-MS confirms the presence of the H-phosphonate intermediate. Subsequently, the volatile components are evaporated at reduced pressure, the residue is dissolved in dry acetonitrile and the evaporation procedure is repeated 3 times. The last evaporation is stopped before the solvent is completely removed and the raw product is either used for the subsequent reaction or is stored frozen at −70° C. in a small volume of acetonitrile.

Example 15b: Synthesis of the linear dinucleotide 5'-OH-2'-TBDMS-benzimidazole riboside-(3'→5')-cyanoethyl phosphate-2'-TBDMS-3'-H-phosphonate-$N^6$-Bz-adenosine The phosphoramidite 5'-DMTr-2'-TBDMS-3'-CEP-benzimidazole riboside (BIOLOG GmbH; the synthesis of this compound and of analoga is state of the art and was described by Parsch[6]; 1.35 equivalents with respect to the nominal H-phosphonate intermediate from Example 15a) is dissolved in dry acetonitrile and is evaporated at reduced pressure four times repeatedly. The last evaporation step is stopped before the solvent is completely removed and the raw product remains in a small volume of acetonitrile. Under an argon atmosphere the solution is added to the 5'-OH-2'-TBDMS-3'-H-phosphonate-$N^6$-Bz-adenosine from Example 15a and the resulting mixture is stirred for 30 min. Subsequently, tert.-butylhydroperoxide in decane (5.5 M; 2 equivalents) is added and stirring under argon is continued for another 30 min.

Afterwards, the volatile components of the reaction mixture are evaporated at reduced pressure, the residue is dissolved in dichloromethane and 10 equivalents of water are added. After addition of dichloroacetic acid in dichloromethane (3%; 18 equivalents) the mixture is stirred for 20 min at room temperature. A considerable excess of pyridine is added and the mixture is stirred for another 5 min at room temperature. Analysis of the raw product by LC-MS confirms the presence of the linear dinucleotide 5'-OH-2'-TBDMS-benzimidazole riboside-(3'→5')-cyanoethyl phosphate-2'-TBDMS-3'-H-phosphonate-$N^6$-Bz-adenosine. The volatile parts of the mixture are evaporated at reduced pressure followed by two consecutive dissolutions in dry pyridine and evaporations at reduced pressure. The residue is dissolved again in dry pyridine to be used in the following reaction step. If needed the resulting solution of the linear dinucleotide can be stored frozen at −70° C.

Example 15c: Synthesis of Cyclic (2'-TBDMS-$N^6$-Bz-adenosine-(3'→5')-H-phosphonate-2'-TBDMS-benzimidazole riboside-(3'→5')-cyanoethyl phosphate)

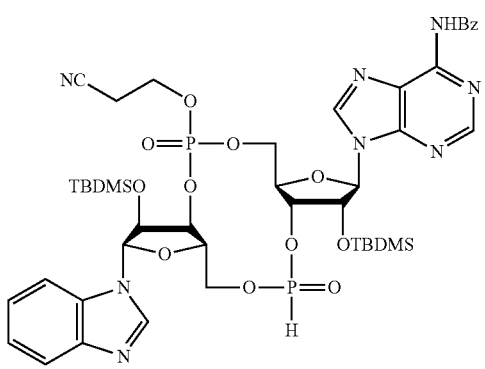

2-Chloro-5,5-dimethyl-1,3,2-dioxaphosphorinane-2-oxide (DMOCP; 3.5 equivalents with respect to the nominally linear dinucleotide 5'-OH-2'-TBDMS-benzimidazole riboside-cyanoethyl phosphate-2'-TBDMS-3'-H-phosphonate-$N^6$-Bz-adenosine from Example 15b) is added under protecting gas atmosphere (argon) to the raw product in pyridine from Example 15b and is stirred under argon for 20 min at room temperature. Analysis of the raw product by LC-MS confirms the presence of the cyclic dinucleotide 2'-TBDMS-$N^6$-Bz-adenosine-(3'→5')-H-phosphonate-2'-TBDMS-benzimidazole riboside-cyanoethyl phosphate, which is immediately further used in Example 15d.

Example 15d: Synthesis of Cyclic (2'-TBDMS-$N^6$-Bz-adenosine-(3'→5')-monophosphate-2'-TBDMS-benzimidazole riboside-(3'→5')-cyanoethyl phosphate)

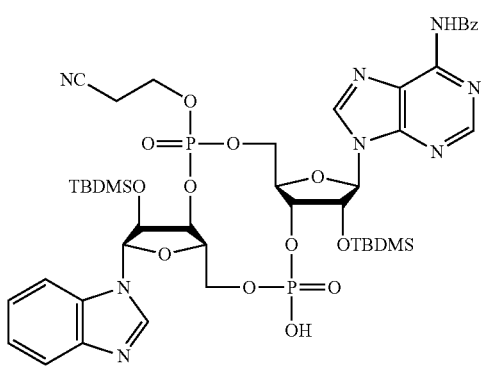

To the raw product from Example 15c is added iodine (1.3 equivalents) and water (30 equivalents) and the mixture is stirred for 20 min at room temperature. Subsequently, aqueous $NaHSO_3$ (0.15%) is added until the solution is completely decolourised. The volume is doubled by addition of an aqueous solution of $NaHCO_3$ and stirring is continued for additional 5 min. The aqueous phase is extracted three times with ethyl acetate/methyl-tert.-butyl ether (1:1 (v:v)). The combined organic phases are dried over $MgSO_4$ and subsequently are evaporated under reduced pressure. LC-MS analysis confirms the presence of the cyclic dinucleotide 2'-TBDMS-$N^6$-Bz-adenosine-(3'→5')-monophosphate-2'-TBDMS-benzimidazole riboside-(3'→5')-cyanoethyl phosphate. If required the resulting cyclic dinucleotide can be stored frozen at −70° C. The raw product is dissolved in a minimal volume of dichloromethane and is purified by means of preparative flash chromatography on silica gel using a methanol/dichloromethane gradient. Product containing fractions are evaporated in vacuo and are further used according to Example 15e. If required the resulting cyclic dinucleotide can be stored frozen at −70° C.

Example 15e: Synthesis of Cyclic (2'-TBDMS-adenosine-(3'→5')-monophosphate-2'-TBDMS-benzimidazole riboside-(3'→5')-monophosphate)

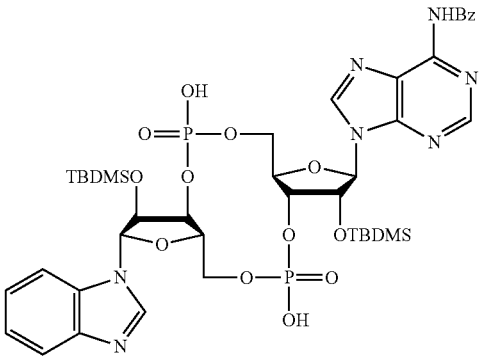

The cyclic dinucleotide 2'-TBDMS-$N^6$-Bz-adenosine-(3'→5')-monophosphate-2'-TBDMS-benzimidazole riboside-(3'→5')-cyanoethyl phosphate described in Example 15d is dissolved in an excess of 33% methylamine in absolute ethanol and is stirred under argon for 4 hours at room temperature. Subsequently, the volatile components of the mixture are evaporated under reduced pressure and the residue is dried for 4-16 hours under high vacuum conditions.

Analysis of the raw product by LC-MS confirms the presence of the target compound. The resulting raw product of cyclic 2'-TBDMS-adenosine-(3'→5')-monophosphate-2'-TBDMS-benzimidazole riboside-monophosphate is used in Example 15f for further reaction. If required the cyclic dinucleotide can be stored frozen at −70° C.

Example 15f: Synthesis of Cyclic (adenosine-(3'→5')-monophosphate-benzimidazole riboside-monophosphate) (c(A(3',5')p-BI(3',5I0)

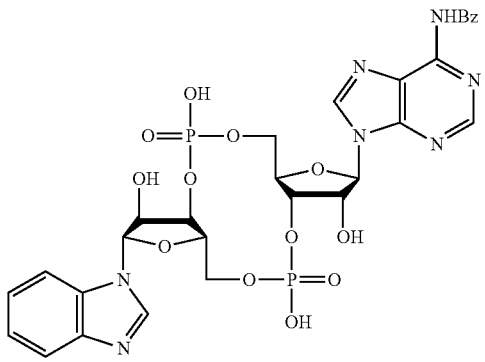

Under argon the cyclic dinucleotide 2'-TBDMS-adenosine-(3'→5')-monophosphate-2'-TBDMS-benzimidazole riboside-monophosphate from Example 15e is dissolved in a mixture of dry pyridine and dry triethyl amine (2:1; (v:v)) and is partially evaporated under reduced pressure to achieve a higher concentration of the cyclic dinucleotide. Subsequently, 25 equivalents of triethylamine trihydrofluoride and dry triethylamine under argon protecting atmosphere are added simultaneously and the resulting solution is stirred under argon for 3.5 h at 50° C. After cooling down to room temperature, excess triethylamine trihydrofluoride is neutralised by addition of methoxytrimethylsilane and stirring for 30 min at ambient temperature. LC-MS analysis of the raw product confirms the presence of the target structure.

All volatile components of the mixture are evaporated under reduced pressure and the residue is dried under high vacuum conditions for 4-16 hours.

The resulting raw product of cyclic adenosine-(3'→5')-monophosphate-benzimidazole riboside-(3'→5')-monophosphate is suspended in water, treated in an ultrasonic bath and the aqueous phase is extracted three times with chloroform.

The product dissolved in the aqueous phase is then filtered, diluted with water and is purified by chromatography on a Q Sepharose™ Fast Flow anion exchanger using a triethylammonium bicarbonate gradient. Product-containing fractions are combined and are evaporated under reduced pressure and the target compound is subsequently further purified by preparative reversed phase chromatography (RP-18) using a mobile phase consisting of a suitable acetonitrile/20 mM triethylammonium formate buffer. The desalting procedure is performed by preparative reversed phase chromatography (RP-18) as well and the desalted target compound is received as the triethylammonium salt. The sodium salt of the target compound is received after elution of the diluted product solution from a SP Sepharose™ Fast Flow cation exchanger column (Na$^+$-form).

--- c[A(3',5')pBI(3',5')p]: 3',5'/3',5'
$C_{22}H_{25}N_7O_{12}P_2$; MW 641.4 (free acid)
UV: $\lambda_{max}$: 254 nm, ε 16150
ESI-MS (+): m/z 642 [M + H]$^+$
ESI-MS (−): m/z 640 [M − H]$^-$

---

Example 16: Chemical Synthesis of Cyclic (5,6-dichlorobenzimidazole riboside-(3'→monophosphorothioate-5,6-dichlorobenzimidazole riboside-(3'→monophosphorothioate) c[DCIBI(3',5')pS-DCIBI(3',5')pS]

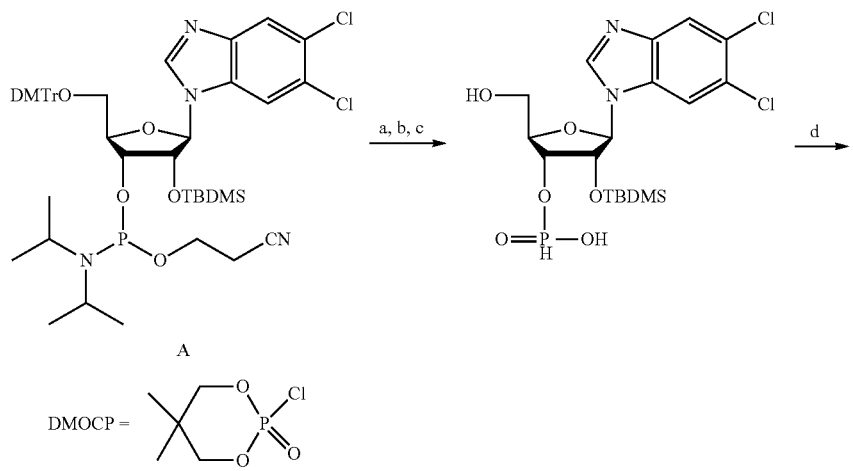

-continued

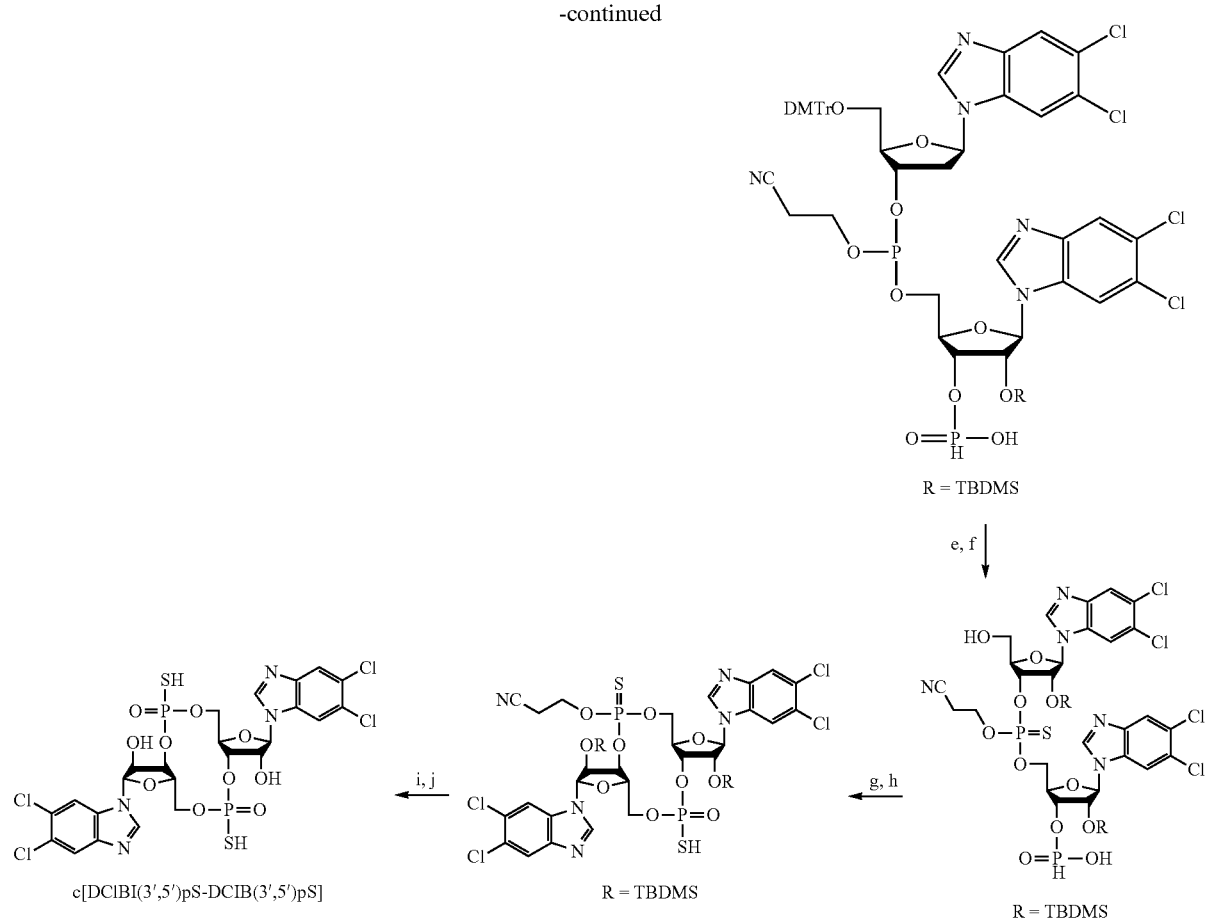

Synthesis 2:

Synthesis of Cyclic (5,6-dichlorobenzimidazole riboside-(3'→5')-monophosphorothioate-5,6-dichlorobenzimidazole riboside-monophosphorothioate) (c[DClBI(3',5')pS-DCIBI(3',5')pS]). Synthetic steps: a) pyridinium trifluoroacetate/H$_2$O; b) tert.-Butylamine; c) dichloroacetic acid/H$_2$O; d) A, pyridine; e) 3-((N,N-dimethylaminomethylidene)amino)-3H-1,2,4-dithiazole-5-thione (DDTT); f) dichloroacetic acid/H$_2$O; g) 2-chloro-5,5-dimethyl-1,3,2-dioxaphosphorinane-2-oxide; h) 3-H-1,2-benzodithiole-3-one; i) methylamine/ethanol; j) triethylamine trihydrofluoride.

Example 16a: Synthesis of the H-phosphonate Intermediate of 5'-OH-2'-TBDMS-3'-H-phosphonate-5,6-dichlorobenzimidazole riboside

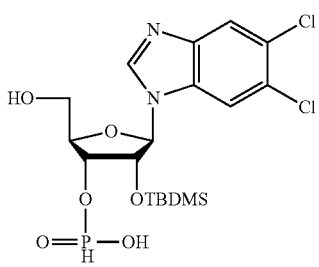

In analogy to example 15a the phosphoramidite 5'-DMTr-2'-TBDMS-3'-CEP-5,6-dichlorobenzimidazole riboside (BI-OLOG GmbH, Bremen) is converted into the aforementioned target compound.

Example 16b: Synthesis of the Linear Dinucleotide 5'-OH-2'-TBDMS-5,6-dichlorobenzimidazole-riboside-(3'→5')-cyanoethyl-phosphorothioate-2'-TBDMS-3'-H-phosphonate-5,6-dichlorobenzimidazole Riboside

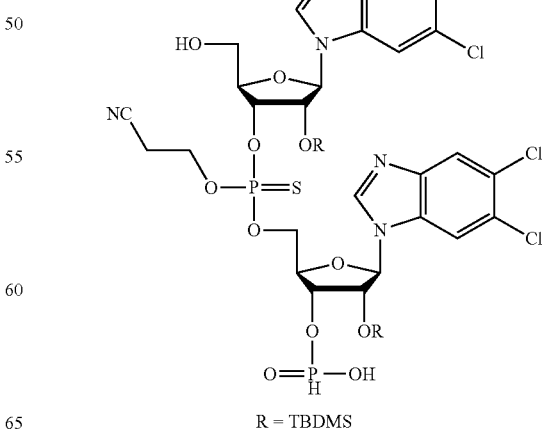

The target structure mentioned above is synthesised in analogy to Example 15b.

Deviant to Example 15b, instead of 5'-DMTr-2'-TBDMS-3'-CEP-benzimidazole riboside, here 5'-DMTr-2'-TBDMS-3'-CEP-5,6-dichlorobenzimidazole riboside (BIOLOG GmbH, Bremen) is used as second nucleotide building block A.

In addition, instead of tert.-butylhydroperoxide in decane from Example 15b, here 1.1 equivalents of 3-((N,N-dimethylaminomethylidene)amino)-3H-1,2,4-dithiazole-5-thione (DDTT) are added for introduction of the cyanoethyl-phosphorothioate unit.

Example 16c: Synthesis of Cyclic (2'-TBDMS-5,6-dichlorobenzimidazole riboside-(3'→5')-H-phosphonate-2'-TBDMS-5,6-dichlorobenzimidazole riboside-(3'→5')-cyanoethyl-phosphorothioate)

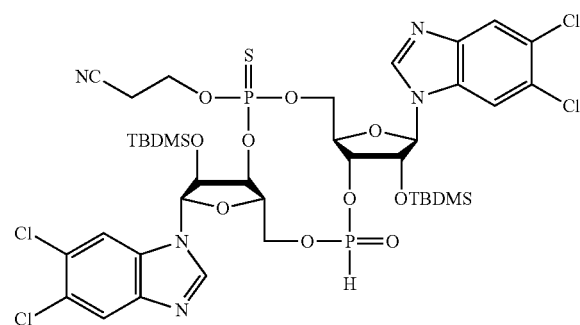

The target structure mentioned above is synthesised in analogy to Example 15c.

Example 16d: Synthesis of Cyclic (2'-TBDMS-5,6-dichlorobenzimidazole riboside-(3'→5')-monophosphorothioate-2'-TBDMS-5,6-dichlorobenzimidazole riboside-(3'→5')-cyanoethyl-phosphorothioate)

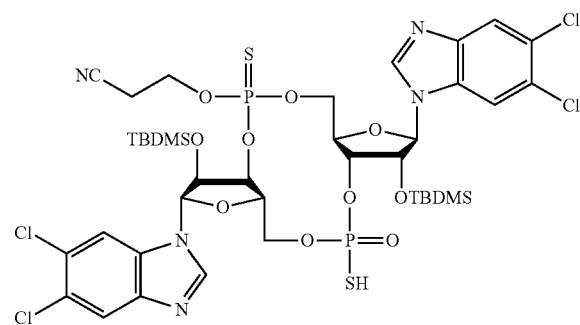

The target structure mentioned above is synthesised in analogy to Example 15d. Instead of iodine in Example 15d, here 1.5 equivalents of 3H-1,2-benzodithiol-3-one are added for the introduction of the phosphorothioate unit.

Example 16e: Synthesis of Cyclic (2'-TBDMS-5,6-dichlorobenzimidazole riboside-(3'→5')-monophosphorothioate-2'-TBDMS-5,6-dichlorobenzimidazole riboside-(3'→5')-monophosphorothioate)

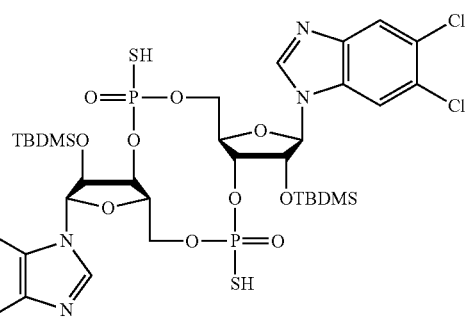

The target structure mentioned above is synthesised in analogy to Example 15e.

Example 16f: Synthesis of Cyclic (5,6-dichlorobenzimidazole riboside-(3'→5')-monophosphorothioate-5,6-dichlorobenzimidazole riboside-(3'→5')-monophosphorothioate) (c[DCIBI(3',5')pS-DCIBI(3',5')pS])

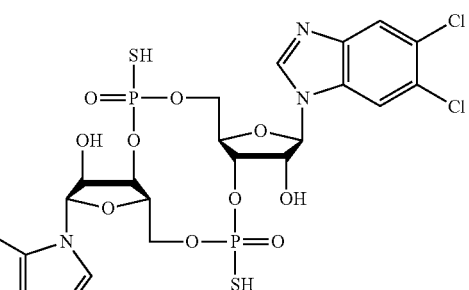

The target structure mentioned above is synthesised in analogy to Example 15f.

c[DCIBI(3',5')pS-DCIBI(3',5')pS]: 3',5'/3',5'
$C_{24}H_{22}Cl_4N_4O_{10}P_2S_2$; MW 794.3 (free acid)
UV: $\lambda_{max}$: 254 nm, ε 12950
ESI-MS (+): m/z 795 [M + H]+
ESI-MS (−): m/z 793 [M − H]−

Example 17: Chemical Synthesis of Cyclic (guanosine-(2' 5')-monophosphorothioate-5,6-dichlorobenzimidazole riboside-(3'→5')-monophosphorothioate) (c[G(2',5')pS-DCIBI(3',5')pS])
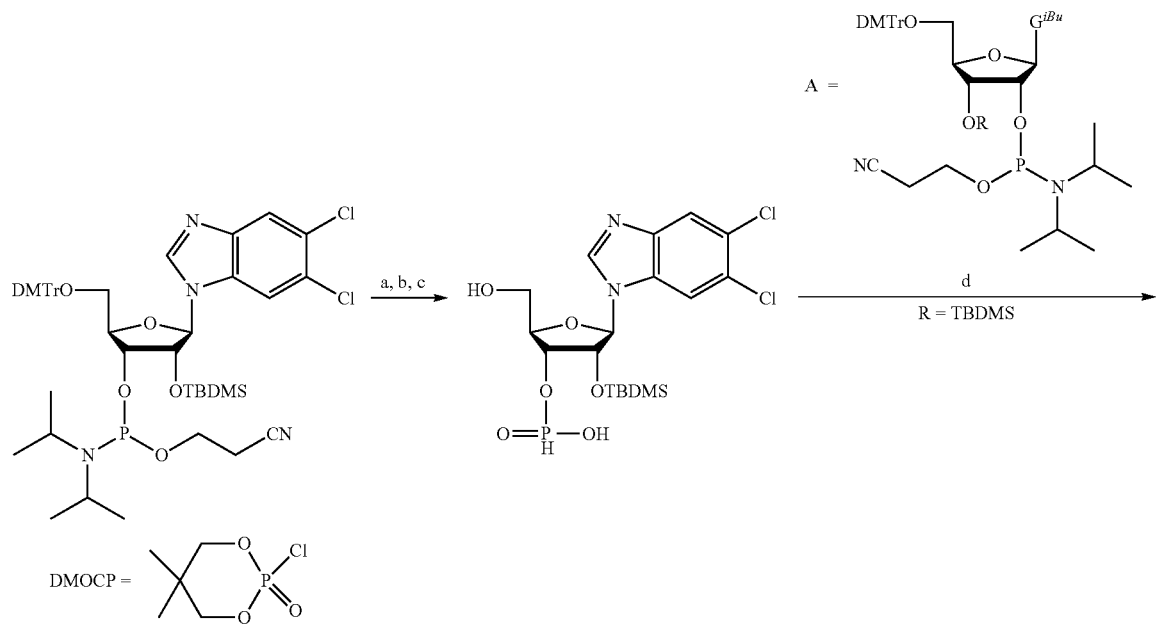
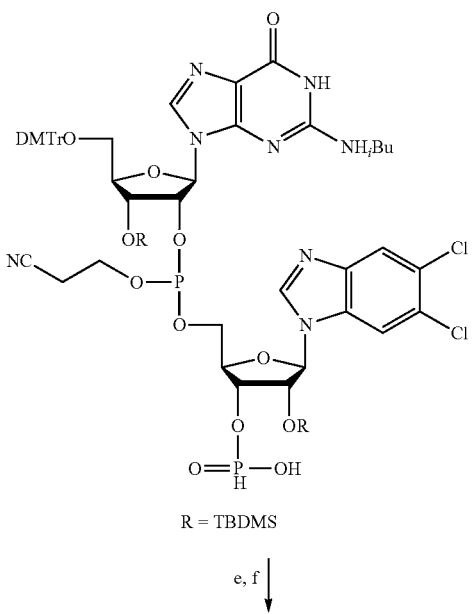

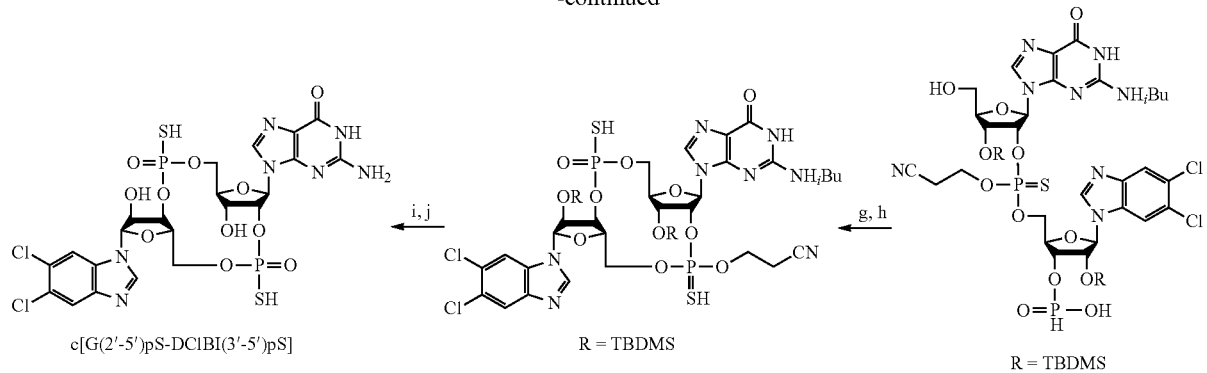

c[G(2'-5')pS-DClBI(3'-5')pS]     R = TBDMS     R = TBDMS

Synthesis 3:

Synthesis of Cyclic (guanosine-(2'→5')-monophosphorothioate-5,6-dichlorobenzimidazole riboside-(3'→5')-monophosphorothioate) (c[G(2',5')pS-DCIBI(3',5')pS]). Synthetic steps: a) pyridinium trifluoroacetate/H$_2$O; b) tert.-butylamine; c) dichloroacetic acid/H$_2$O; d) A, pyridine; e) 3-((N,N-dimethylaminomethylidene)amino)-3H-1,2,4-dithiazole-5-thione (DDTT); f) dichloroacetic acid/H$_2$O; g) 2-chloro-5,5-dimethyl-1,3,2-dioxaphosphorinane-2-oxide; h) 3-H-1,2-benzodithiol-3-one; I) methylamine/ethanol; j) triethylamine trihydrofluoride.

Example 17a: Synthesis of H-phosphonate Intermediate 5'-OH-2'-TBDMS-3'-H-phosphonate-5,6-dichlorobenzimidazole Riboside

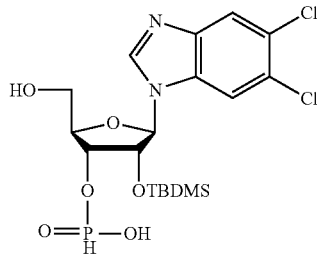

The phosphoramidite 5'-DMTr-2'-TBDMS-3'-CEP-5,6-dichlorobenzimidazole riboside (0.7 mmol) (BIOLOG GmbH, Bremen) was dissolved in 12 ml dry acetonitrile, 2 equivalents of water and 1.2 equivalents of pyridinium trifluoroacetate were added and the mixture was stirred for 15 minutes at room temperature. Then, volatile components were evaporated under reduced pressure. Subsequently, 100 equivalents of tert.-butylamine were added and after the resulting solution was stirred for 30 minutes at room temperature the mixture was evaporated again under reduced pressure. The residue was dissolved in 30 ml of acetonitrile and evaporated again under reduced pressure. The residue was dissolved in 20 ml of dichloromethane and 10 equivalents of water were added. Subsequently, 9 equivalents of dichloroacetic acid, from a solution of dichloroacetic acid in dichloromethane (3%), were added and the solution was stirred for 10 minutes at room temperature.

Afterwards, 18 equivalents of pyridine were added and the solution was stirred for 5 minutes at room temperature. LC-MS analysis confirmed the presence of the H-phosphonate intermediate. The volatile components were removed under reduced pressure, followed by three consecutive dissolution and evaporation steps under reduced pressure with 10 ml of dry acetonitrile each. The last evaporation was only performed until about 4 ml of acetonitrile were left in order to have the raw product in appropriate form for the next reaction step.

Example 17b: Synthesis of the linear dinucleotide 5'-OH-3'-TBDMS-N$^2$-isobutyrylguanosine-(2'→5')-cyanoethyl-phosphorothioate-2'-TBDMS-3'-H-phosphonate-5,6-dichlorobenzimidazole Riboside

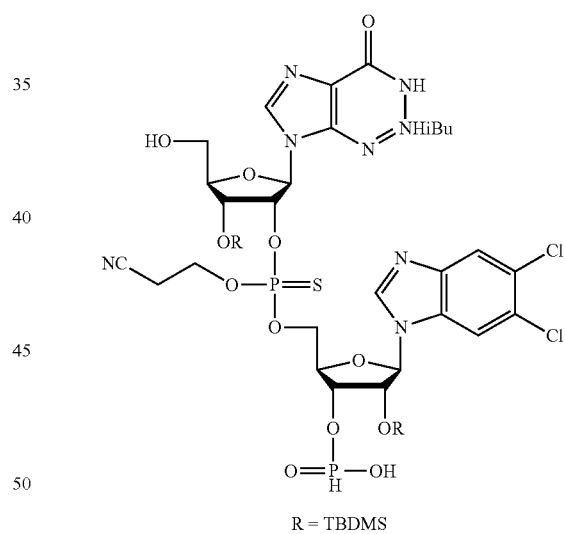

R = TBDMS

The phosphoramidite 5'-DMTr-3'-TBDMS-2'-CEP-N$^2$-isobutyrylguanosine (Chemgenes Inc., USA, 1.35 equivalents with respect to the nominal H-phosphonate intermediate (0.7 mmol) from Example 17a) was dissolved in 12 ml of dry acetonitrile and was evaporated under reduced pressure four times. The last evaporation was not completed until dryness, but about 3 ml of acetonitrile were left.

This solution was added under argon protection to 5'-OH-2'-TBDMS-3' H-phosphonate-5,6-dichlorobenzimidazole riboside from Example 17a and the resulting solution was stirred under argon for 15 minutes. Subsequently, 1.1 equivalents of 3-((N,N-dimethylaminomethylidene)amino)-3H-1,2,4-dithiazole-5-thione (DDTT) were added and the mixture was stirred under argon for further 30 minutes.

The resulting intermediate was stored 16 hours at −70° C. The volatile components of the mixture were evaporated under reduced pressure and the residue was dissolved in 20 ml of dichloromethane and equivalents of water. Dichloroacetic acid in dichloromethane (3%; 18 equivalents) was added and the mixture was stirred for 20 minutes at room temperature. 10 ml of pyridine were added and stirring was continued for further 10 minutes. LC-MS analysis of the raw mixture confirmed the presence of the linear dinucleotide 5'-OH-3'-TBDMS-$N^2$-isobutyrylguanosine-cyanoethyl-phosphorothioate-2'-TBDMS-3'-H-phosphonate-5,6-dichlorobenzimidazole riboside.

Volatile components of the mixture were evaporated under reduced pressure and subsequently the residue was dissolved in 20 ml of dry pyridine and evaporated under reduced pressure two times. The residue was dissolved again in 30 ml of dry pyridine and was co-evaporated to ~20 ml in order to be used in the following reaction.

Example 17c: Synthesis of Cyclic (3'-TBDMS-$N^2$-isobutyrylguanosine-(2'→5')-cyanoethyl-phosphorothioate-2'-TBDMS-5,6-dichlorobenzimidazole riboside-(3'→5')-H-phosphonate)

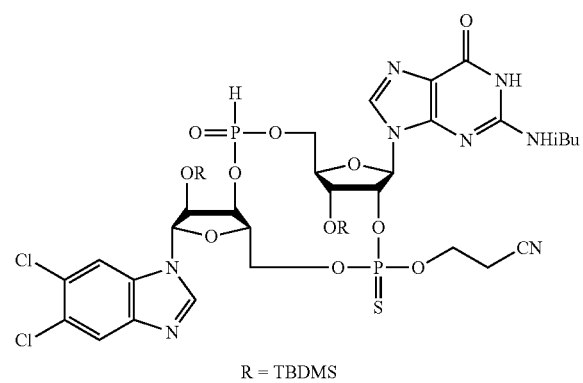

R = TBDMS

Under argon atmosphere 2-chloro-5,5-dimethyl-1,3,2-dioxaphosphorinane-2-oxide (DMOCP; 3.5 equivalents with respect to the nominally linear dinucleotide 5'-OH-3'-TBDMS-$N^2$-isobutyrylguanosine-(2'→5')-cyanoethyl-phosphorothioate-2'-TBDMS-3'-H-phosphonate-5,6-dichlorobenzimidazole riboside (0.7 mmol from Example 17b) were added to the raw product from Example 17b.

LC-MS analysis of the raw product confirmed the presence of the cyclic dinucleotide 3'-TBDMS-$N^2$-isobutyrylguanosine-(2'→5')-cyanoethyl-phosphorothioate-2'-TBDMS-5,6-dichlorobenzimidazole riboside-H-phosphonate, which was immediately further processed in Example 17d.

Example 17d: Synthesis of Cyclic (3'-TBDMS-$N^2$-isobutyrylguanosine-(2'→5')-cyanoethyl-phosphorothioate-2'-TBDMS-5,6-dichlorobenzimidazole riboside-(3'→5')-monophosphorothioate)

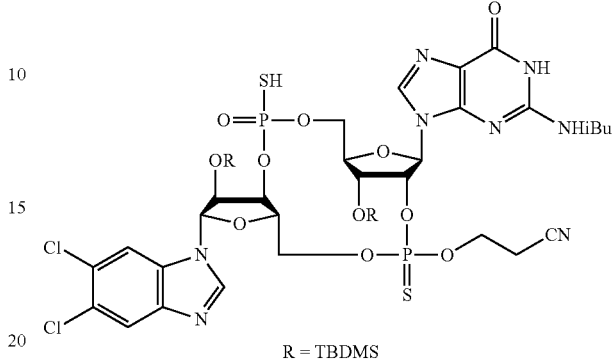

R = TBDMS

To the raw product from Example 17c 3H-1,2-benzodithiol-3-one (1.5 equivalents) and water (35 equivalents) were added and the mixture was stirred for 30 minutes at room temperature. Subsequently, 3.3 g $NaHCO_3$ in 120 ml of water were added and the mixture was stirred for further 5 minutes.

The aqueous phase was extracted three times with ethylacetate/methyl-tert.-butylether (1:1 (v:v); 1×120 ml, 2×60 ml) and the combined organic phases were dried with $MgSO_4$ and were evaporated under reduced pressure.

LC-MS-analysis of the raw product confirmed the presence of the cyclic dinucleotide 3'-TBDMS-$N^2$-isobutyrylguanosine-(2'→5')-cyanoethyl-phosphorothioate-2'-TBDMS-5,6-dichlorobenzimidazole riboside-(3'→5')-monophosphorothioate.

The residue was co-evaporated twice with 50 ml of toluene and dried over night under high vacuum conditions. The raw product was then dissolved in a minimal amount of dichloromethane and was purified by flash chromatography using silica gel and a methanol/dichloromethane gradient. Product-containing fractions were evaporated under reduced pressure and were used for Example 17e.

Example 17e: Synthesis of Cyclic (3'-TBDMS-guanosine-(2'→5')-monophosphorothioate-2'-TBDMS-5,6-dichlorobenzimidazole riboside-(3'→5')-monophosphorothioate)

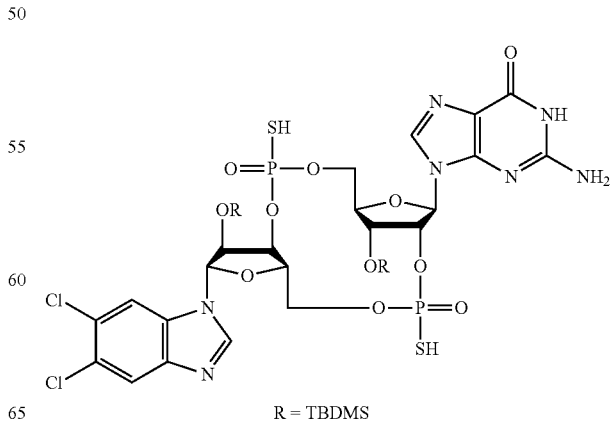

R = TBDMS

To the cyclic dinucleotide 3'-TBDMS-N²-isobutyrylguanosine-(2'-5')-cyanoethyl-phosphorothioate-2'-TBDMS-5,6-dichlorobenzimidazole riboside-(3'→5')-monophosphorothioate from Example 17d, an excess of 33% methylamine in absolute ethanol (150 ml) was added under an argon atmosphere and the mixture was stirred under argon for 4 hours at room temperature. Subsequently, the volatile components of the mixture were evaporated under reduced pressure and the residue was dried under high vacuum conditions for 16 hours. LC-MS analysis of the raw product confirmed the presence of the target compound. The resulting raw product of cyclic (3'-TBDMS-guanosine-(2'→5')-monophosphorothioate-2'-TBDMS-5,6-dichlorobenzimidazole riboside-(3'→5')-monophosphorothioate) was further used in Example 17f.

Example 17f: Synthesis of Cyclic (guanosine-(2'→5')-monophosphorothioate-5,6-dichlorobenzimidazole riboside-(3'→5')-monophosphorothioate) (c[G(2',5')pS-DClBI(3',5')pS])

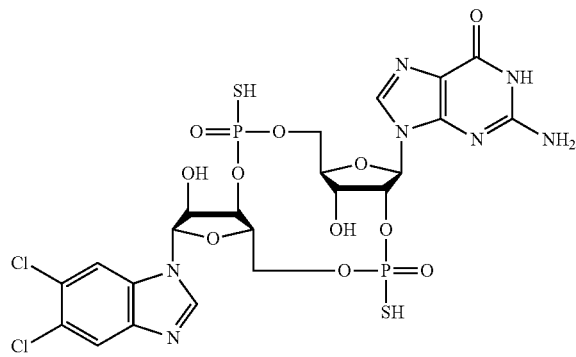

The cyclic dinucleotide 3'-TBDMS-guanosine-(2'→5')-monophosphorothioate-2'-TBDMS-5,6-dichlorobenzimidazole riboside-(3'→5')-monophosphorothioate from Example 17e was dissolved under argon atmosphere in a mixture consisting of dry pyridine and dry triethylamine (2:1; (v:v), 60 ml) and concentrated under reduced pressure to approximately 10 ml. Subsequently, 50 equivalents of triethylamine trihydrofluoride and 17 ml dry triethylamine were added under argon and the resulting mixture was stirred for 4 hours under argon at 55° C.

Afterwards, the mixture was allowed to cool down to room temperature and the excess triethylamine trihydrofluoride was inactivated by addition of 15 ml of methoxytrimethylsilane followed by stirring for 30 min at room temperature. LC-MS analysis of the raw product confirmed the presence of the target compound.

All volatile components of the mixture were evaporated under reduced pressure and the residue was dried further 16 hours at high vacuum conditions.

The resulting raw product of cyclic (guanosine-(2'→5')-monophosphorothioate-5,6-dichlorobenzimidazole riboside-(3'→5')-monophosphorothioate) was suspended in water, was treated in an ultrasonic bath and was extracted three times with chloroform.

After filtration the raw product was diluted with water and was purified with a Q Sepharose™ Fast Flow anion exchanger, applying a triethylammonium bicarbonate gradient.

Product containing fractions were concentrated under reduced pressure and both main isomers of the target compound were further purified by preparative reversed phase chromatography (RP-18) using a suitable acetonitrile/20 mM triethylammonium formate eluent.

Under these conditions, the main isomer 1 (MI1) elutes faster from the reversed phase column compared to the main isomer 2 (MI2).

MI1 and MI2 are those isomer fractions of the respective compound, which can be assigned to represent percentagewise the most dominant HPLC signals of this compound. This definition for main isomer 1 and main isomer 2 is valid analogously for other compounds within this document as well.

The desalting of the two main isomers of the target compound was performed with preparative reversed phase chromatography (RP-18) as well and the desalted main isomers of the target compound were received as triethylammonium salts. The sodium salts of the main isomers of the target compound were received by passage of a diluted product solution through a SP Sepharose™ Fast Flow cation exchanger (Natform).

c[G(2',5')pS-DClBI(3',5')pS]: 2',5'/3',5'
$C_{22}H_{23}Cl_2N_7O_{11}P_2S_2$; MW 758.4 (free acid)
Main isomer 1 (faster eluting isomer),
(c[G(2',5')pS-DClBI(3',5')pS], MI1)
UV: $\lambda_{max}$: 256 nm, ε 17850
ESI-MS (+): m/z 758 [M + H]⁺
ESI-MS (−): m/z 756 [M − H]⁻
$^{31}P\{1H\}$ NMR (162 MHz, D₂O) δ 56.29 (s, 1P), 56.05 (s, 1P).
Main isomer 2 (slower eluting isomer),
(c[G(2',5')pS-DClBI(3',5')pS], MI2)
UV: $\lambda_{max}$: 256 nm, ε 17850
ESI-MS (+): m/z 758 [M + H]⁺
ESI-MS (−): m/z 756 [M − H]⁻
$^{31}P\{1H\}$ NMR (162 MHz, D₂O) δ 55.90 (s, 1P), 52.02 (s, 1P).

The following Examples 17g-17n were synthesised according to the procedures described in Examples 17a-17f:

Example 17d: Cyclic (guanosine-(2'→5')-monophosphorothioate-benzimidazole riboside-(3'→5')-monophosphorothioate), (c[G(2',5')pS-BI(3',5')pS]), Main Isomer 1 and Main Isomer 2 c[G(2',5')pS-BI(3',5')pS]: 2',5'/3',5'
$C_{22}H_{25}N_7O_{11}P_2S_2$; MW 689.6 (free acid)
Main isomer 1 (faster eluting isomer),
(c[G(2',5')pS-BI(3',5')pS], MI1)
UV: $\lambda_{max}$: 252 nm, ε 17850
ESI-MS (+): m/z 690 [M + H]⁺
ESI-MS (−): m/z 688 [M − H]⁻
Main isomer 2 (slower eluting isomer),
(c[G(2',5')pS-BI(3',5')pS], MI2)
UV: $\lambda_{max}$: 252 nm, ε 17850
ESI-MS (+): m/z 690 [M + H]⁺
ESI-MS (−): m/z 688 [M − H]⁻

Example 17h: Cyclic (adenosine-(3'→5')-monophosphorothioate-benzimidazole riboside-(2'→5')-monophosphorothioate), (c[A(3',5')pS-BI(2',5')pS]), Main Isomer 1 and Main Isomer 2 c[A(3',5')pS-BI(2',5')pS]: 3',5'/2',5'
$C_{22}H_{25}N_7O_{10}P_2S_2$; MW 673.6 (free acid)
Main isomer 1 (faster eluting isomer),
(c[A(3',5')pS-BI(2',5')pS], MI1)
UV: $\lambda_{max}$: 253 nm, ε 17600
ESI-MS (+): m/z 674 [M + H]$^+$
ESI-MS (−): m/z 672 [M − H]$^-$
Main isomer 2 (slower eluting isomer),
(c[A(3',5')pS-BI(2',5')pS], MI2)
UV: $\lambda_{max}$: 253 nm, ε 17600
ESI-MS (+): m/z 674 [M + H]$^+$
ESI-MS (−): m/z 672 [M − H]$^-$

Example 17i: Cyclic (2'-fluoro-2'-deoxyadenosine-(3'→5')-monophosphorothioate-benzimidazole riboside-(2'→5')-monophosphorothioate), (c[2'-F-dA(3',5')pS-BI(2',5')pS]), Main Isomer 1 and Main Isomer 2 c[2'-F-dA(3',5')pS-BI(2',5')pS]: 3',5'/2',5'
$C_{22}H_{24}FN_7O_9P_2S_2$; MW 675.5 (free acid)
Main isomer 1 (faster eluting isomer),
(c[2'-F-dA(3',5')pS-BI(2',5')pS], MI1)
UV: $\lambda_{max}$: 253 nm, ε 17600
ESI-MS (+): m/z 676 [M + H]$^+$
ESI-MS (−): m/z 674 [M − H]$^-$
Main isomer 2 (slower eluting isomer),
(c[2'-F-dA(3',5')pS-BI(2',5')pS], MI2)
UV: $\lambda_{max}$: 253 nm, ε 17600
ESI-MS (+): m/z 676 [M + H]$^+$
ESI-MS (−): m/z 674 [M − H]$^-$

Example 17j: Cyclic (5,6-Dichlorobenzimidazole riboside-(2'→5')-monophosphorothioate-5,6-dichlorobenzimidazole riboside-(3'→5')-monophosphorothioate), (c[DClBI(2',5')pS-DClBI(3',5')pS]), Main Isomer 1 and Main Isomer 2 c[DClBI(2',5')pS-DClBI(3',5')pS]: 2',5'/3',5'
$C_{24}H_{22}Cl_4N_4O_{10}P_2S_2$; MW 794.3 (free acid)
Main isomer 1 (faster eluting isomer),
(c[DClBI(2',5')pS-DClBI(3',5')pS], MI1)
UV: $\lambda_{max}$: 254 nm, ε 12950
ESI-MS (+): m/z 795 [M + H]$^+$
ESI-MS (−): m/z 793 [M − H]$^-$
Main isomer 2 (slower eluting isomer),
(c[DClBI(2',5')pS-DClBI(3',5')pS], MI2)
UV: $\lambda_{max}$: 254 nm, ε 12950
ESI-MS (+): m/z 795 [M + H]$^+$
ESI-MS (−): m/z 793 [M − H]$^-$

Example 17k: Cyclic (adenosine-(2'→5')-monophosphorothioate-5,6-dichlorobenzimidazole riboside-(3'→5')-monophosphorothioate), (c[A(2',5')pS-DClBI(3',5')pS]), Main Isomer 1 and Main Isomer 2 c[A(2',5')pS-DClBI(3',5')pS]: 2',5'/3',5'
$C_{22}H_{23}Cl_2N_7O_{10}P_2S_2$; MW 742.4 (free acid)
Main isomer 1 (faster eluting isomer),
(c[A(2',5')pS-DClBI(3',5')pS], MI1)
UV: $\lambda_{max}$: 260 nm, ε 19400
ESI-MS (+): m/z 742 [M + H]$^+$
ESI-MS (−): m/z 740 [M − H]$^-$
Main isomer 2 (slower eluting isomer),
(c[A(2',5')pS-DClBI(3',5')pS], MI2)
UV: $\lambda_{max}$: 260 nm, ε 19400
ESI-MS (+): m/z 742 [M + H]$^+$
ESI-MS (−): m/z 740 [M − H]$^-$

Example 17l: Cyclic (2'-fluoro-2'-deoxyadenosine-(3'→5')-monophosphorothioate-5,6-dichlorobenzimidazole riboside-(2'→5')-monophosphorothioate), (c[2'-F-dA(3',5')pS-DClBI(2',5')pS]), Main Isomer 1 and Main Isomer 2 c[2'-F-dA(3',5')pS-DClBI(2',5')pS]: 3',5'/2',5'
$C_{22}H_{22}Cl_2FN_7O_9P_2S_2$; MW 744.4 (free acid)
Main isomer 1 (faster eluting isomer),
(c[2'-F-dA(3',5')pS-DClBI(2',5')pS], MI1)
UV: $\lambda_{max}$: 260 nm, ε 19400
ESI-MS (+): m/z 745 [M + H]$^+$
ESI-MS (−): m/z 743 [M − H]$^-$
Main isomer 2 (slower eluting isomer),
(c[2'-F-dA(3',5')pS-DClBI(2',5')pS], MI2)
UV: $\lambda_{max}$: 260 nm, ε 19400
ESI-MS (+): m/z 745 [M + H]$^+$
ESI-MS (−): m/z 743 [M − H]$^-$

Example 17m: Cyclic (adenosine-(3'→5')-monophosphorothioate-5,6-dichlorobenzimidazole riboside-(2'→5')-monophosphorothioate), (c[A(3',5')pS-DClBI(2',5')pS]), Main Isomer 1 and Main Isomer 2 c[A(3',5')pS-DClBI(2',5')pS]: 3',5'/2',5'
$C_{22}H_{23}Cl_2N_7O_{10}P_2S_2$; MW 741 (free acid)
Main isomer 1 (faster eluting isomer),
(c[A(3',5')pS-DClBI(2',5')pS], MI1)
UV: $\lambda_{max}$: 260 nm, ε 19400
ESI-MS (+): m/z 742 [M + H]$^+$
ESI-MS (−): m/z 741 [M − H]$^-$
Main isomer 2 (slower eluting isomer),
(c[A(3',5')pS-DClBI(2',5')pS], MI2)
UV: $\lambda_{max}$: 260 nm, ε 19400
ESI-MS (+): m/z 742 [M + H]$^+$
ESI-MS (−): m/z 741 [M − H]$^-$

Example 17n: Cyclic (adenosine-(2'→5')-monophosphorothioate-benzimidazole riboside-(3'→5')-monophosphorothioate), (c[A(2',5')pS-BI(3',5')pS]), Main Isomer 1 and Main Isomer 2

--- c[A(2',5')pS-BI(3',5')pS]: 2',5'/3',5'
$C_{22}H_{25}N_7O_{10}P_2S_2$; MW 673.1 (free acid)
Main isomer 1 (faster eluting isomer),
(c[A(2',5')pS-BI(3',5')pS], MI1)
UV: $\lambda_{max}$: 253 nm, ε 17600
ESI-MS (+): m/z 674 [M + H]⁺
ESI-MS (−): m/z 672 [M − H]⁻
Main isomer 2 (slower eluting isomer),
(c[A(2',5')pS-BI(3',5')pS],MI2)
UV: $\lambda_{max}$: 253 nm, ε 17600
ESI-MS (+): m/z 674 [M + H]⁺
ESI-MS (−): m/z 672 [M − H]⁻

---

Example 18: Lipophilicity Determinations of the Inventive CDNs by Means of Gradient HPLC The octanol/water coefficient Log P is the commonly accepted indicator for the expected property of a given chemical entity to pass cellular membranes by passive diffusion. However, its practical determination for polar compounds such as multiply charged nucleotides is difficult in reality. Often, the information about membrane permeability must be received by fragmental analysis or other calculations.

Given this fact, an established HPLC method is used here, which is based on the measurement of retention on a reversed phase column[7]. In contrast to Log P, this method yields the indicator log $k'_g$, which allows for a ranking of different nucleotides of the same charge according to their lipophilicity.

Since CDNs are twofold negatively charged molecules which are only very insufficiently retarded on a reversed phase HPLC column, the determinations were performed in presence of the lipophilic triethylammonium cation (ion pair chromatography).

According to the established method[7] HPLC gradient 1 was used for the determination of lipophilicity. Unmodified CDNs, such as c-diAMP (log $k'_g$ 0.991), c-diGMP (log $k'_g$ 0.840) or 2,3-cGAMP (log $k'_g$ 0.766) (Table 2) show very polar properties here and it appears very unlikely, that they could pass cellular membranes by passive diffusion.

The inventive CDNs with at least one benzimidazole nucleobase possess, however, considerably higher lipophilicity and show correspondingly higher retention times and thus very high log $k'_g$ values in this analytical read-out system, as shown by way of example for 11 new inventive CDNs in Table 2.

Substitution of one of the oxygen atoms in the phosphate moiety of the inventive CDNs by sulphur or borane even further increases lipophilicity, so that phosphorothioate analogues and especially the boranophosphate analogues of the benzimidazole-CDNs are magnitudes of orders more lipophilic compared to their parent compounds.

Substitutions in positions 4, 5, 6 and 7 of the 6-membered ring as well as in position 2 of the imidazole part of the fundamental benzimidazole structure usually increase lipophilicity as well.

TABLE 2

HPLC retention times and lipophilicity data (log $k'_g$) of the new inventive CDNs.

| # | Compound | HPLC retention time gradient 1 | HPLC retention time gradient 2 | log $k'_g$ |
|---|---|---|---|---|
|  | Thiourea | 2,567 | 2,813 |  |
|  | c-diGMP | 12,520 | 11,700 | 0.840 |
|  | c-diAMP | 14,280 | 13,187 | 0.991 |
|  | 2',3'-cGAMP | 11,647 | 11,440 | 0.766 |
| 7 | c[DClBI(3',5')pDClBI(3',5')p] | 37,400 | 34,227 | 2.970 |
| 1 | c[BI(3',5')pBI(3',5')p] | 22,933 | 20,687 | 1.732 |
| 98, MI1 | c[A(3',5')pS-BI(2',5')pS], MI1 | 20,507 | 19,880 | 1.524 |
| 98, MI2 | c[A(3',5')pS-BI(2',5')pS], MI2 | 21,207 | 20,793 | 1.584 |
| 79 | c[2'-F-dA(3',5')pBI(3',5')p] | 18,153 | 16,760 | 1.322 |
| 81 | c[2-F-dA(3',5')pDClBI(3',5')p] | 26,520 | 24,873 | 2.039 |
| 23, MI1 | c[G(2',5')pS-BI(3',5')pS], MI1 | 20,327 | 20,673 | 1.509 |
| 23, MI2 | c[G(2',5')pS-BI(3',5')pS], MI2 | 22,393 | 22,687 | 1.658 |
| 85 | c[2'-F-dI(3',5')pBI(3',5')p] | 16,847 | 16,280 | 1.211 |
| 29, MI1 | c[G(2',5')pS-DClBI(3',5')pS], MI1 | 29,780 | 29,740 | 2.318 |
| 29, MI2 | c[G(2',5')pS-DClBI(3',5')pS], MI2 | 30,773 | 31,027 | 2.403 |

BIOLOGICAL EXAMPLES

Example 19: Determination of STING-Induced Dimerisation and Phosphorylation of IRF3, and of STING-Induced Phosphorylation of TBK1 after Application of the Inventive CDNs Cell line: THP-1 cells (Sigma Cat. No. 88081201-1VL) were isolated from peripheral blood of a one year old male patient with acute leukaemia.

After application of an inventive CDN or a buffer control to THP1 cells in a culture dish a cell lysate is prepared, of which one part is applied to a native polyacrylamide gel and the other part to two denaturing polyacrylamide gels (SDS-PAGE). The developed gels are analysed with Western Blot technique.

In case of the native gel an IRF3 antibody is used. In the buffer control a single band is detected, which shows a running behaviour according to the molecular weight of IRF3.

The presence of an inventive CDN results in the formation of a second band, showing a running behaviour, which corresponds to the doubled molecular weight of IRF3. This band represents the dimer of IRF3, that has been formed under the influence of an inventive CDN.

In case of the two denaturing gels, either an antibody against phosphorylated IRF3 or an antibody against phosphorylated TBK1 is used. In the buffer control for each of the gels only a very weak band is detected. After application of an inventive CDN, the intensities of these bands are much more pronounced. This increase of intensity reflects the phosphorylation of IRF3 and of TBK1, respectively, induced by the inventive CDNs. Both, the dimerisation of IRF3 and the detected phosphorylations are a direct result of STING activation.

By way of example, the tested compounds 4, 11, 29 and 30 (compare Table 1, above) from the group of inventive CDNs give positive results in this assay.

Example 20: Determination of STING Induced Activity after Administration of Inventive CDNs by Means of an Interferon-β Promoter Reporter Construct Cell line: THP1-Blue™ cells (InvivoGen, catalogue number: thp-isg) are derived from THP1 cells. THP1-Blue™ cells in a cell culture dish are stimulated by the administration of a CDN according to the invention or a buffer control.

In these genetically modified cells, the gene for secreted embryonic alkaline phosphatase (SEAP) is under the control of an interferon-β promoter.

After stimulation of the cells with an inventive CDN, the supernatant of the cell culture was removed and the enzymatic activity of SEAP was measured photometrically in a colorimetric assay by measuring the extinction at 625 nm (optical density; OD 625 nm).

Administration of an inventive CDN induces an increase in the activity of SEAP, which is a measure of the activity of the STING signalling pathway.

By way of example, the tested compounds 23, MI2; 29, MI2; 79; 81; 98, MI1 gave concentration-dependent (0 µg/ml; 10 µg/ml; 20 µg/ml; 40 µg/ml) positive results in this assay in form of elevated OD at 625 nm and showed increased SEAP-activity by a factor of up to >10 compared to the control compounds 3',3'-cGAMP and c-diAMP (pls. ref. FIG. 1).

Figure 2:
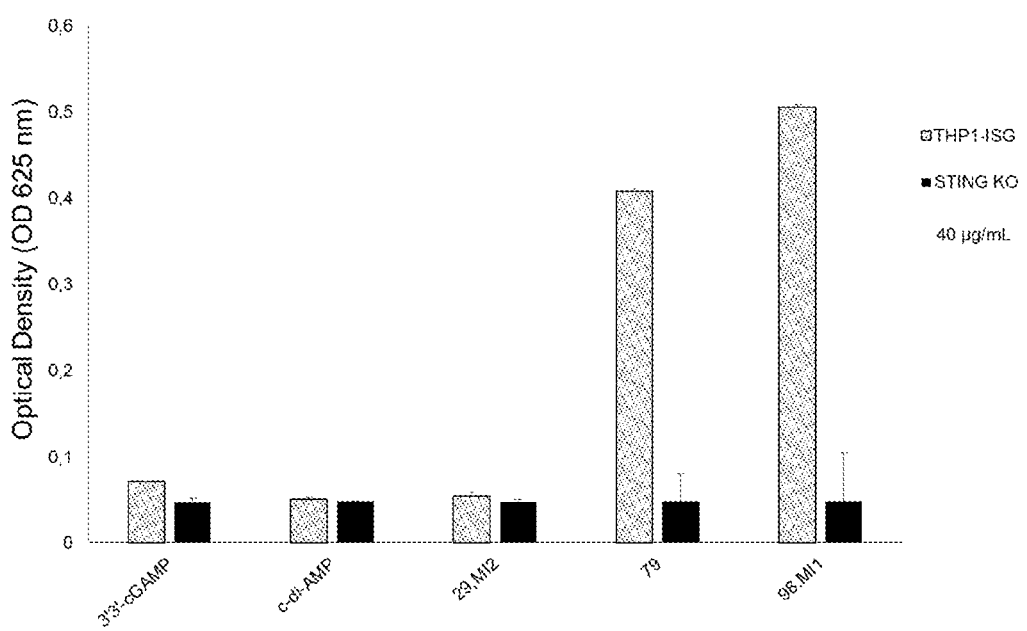
FIG. 2 is a graph depicting optical density as compared to various compounds according in accordance with aspects of the invention.

This effect of elevated OD at 625 nm was no longer observed in cells where STING had been removed genetically (knock out; STING KO), as demonstrated by way of example with compounds 29, MI2; 79; 98, MI1 (each applied in a concentration of 40 µg/ml) in a comparative experiment with THP1-Blue™ cells and with THP1 Dual™ KO STING cells (InvivoGen, catalogue number: thpd-ko-stg) (pls. ref. FIG. 2).

Example 21: Determination of the Amount of mRNA for Interferon-α and -β Formed Under the Influence of Inventive CDNs Cell line: THP-1 cells (Sigma catalogue number 88081201-1 VL) were isolated from the peripheral blood of a one year old male patient with acute leukaemia isolated.

THP1 cells in a cell culture dish are stimulated by the administration of a CDN according to the invention or receive a buffer control. After stimulation, the mRNA is isolated from the cells and is converted into cDNA by the enzyme reverse transcriptase. The relative concentration of the cDNA of the RNA coding for interferon-α and -β, obtained after the administration of an inventive CDN compared to the buffer control is determined by means of quantitative PCR. The administration of a CDN according to the invention, leads to an increase in the formation of mRNA coding for interferon-α and -β.

This effect is no longer observed in cells where STING has been genetically removed (knock out), By way of example, the compounds of Example 19 give positive results in this assay.

Example 22: Determination of the Amount of Interferon-β Secreted Under the Influence of Inventive CDNs Cell line: THP-1 cells (Sigma catalogue no. 88081201-1 VL) were isolated from the peripheral blood of a one year old male patient with acute leukaemia isolated. HEK293 is a cell line, which was prepared from human embryonal kidney tissue.

THP1 cells and HEK293 cells, in which STING was brought artificially to expression, are stimulated by the administration of a CDN according to the invention or receive a buffer control. After stimulation, the culture medium is removed and the amount of the interferon-β secreted into the medium by the cells is determined, using an enzymatically coupled immunotest (enzymatic linked immunoassay, ELISA).

To this end, the system "Human IFN-beta ELISA Kit" (R & D Systems, catalogue number 41410) is used according to the manufacturer's instructions. Addition of an inventive CDN leads to a significant increase in the detectable amount of interferon-β.

By way of example, the compounds of Example 19 give positive results in this assay.

Example 23: Determination of the Interaction Affinity of the Inventive CDNs and STING by Isothermal Titration Calorimetry (ITC)

Constructs of human STING are expressed in bacteria as GST-fusion proteins.

The purification under proteolytic cleavage of the GST tag is performed by affinity chromatography and size exclusion chromatography. STING solutions with a concentration of up to 200 µM are placed in the measuring cell and are titrated with an inventive CDN in an identical buffer.

The heat tints, observed during the titration, show a clear interaction of an inventive CDN with STING. The affinities determined are in the same order of magnitude as compared to natural cyclic dinucleotides or even surpass them.

By way of example, the compounds of Example 19 give positive results in this assay.

ABBREVIATION USED

| | |
|---|---|
| TRIS-HCl | Tris(hydroxymethyl)aminomethane, hydrochloride |
| Cy | cyclohexyl |
| Cyp | cyclopentyl |
| DMSO | Dimethyl sulfoxide |
| UV | Ultraviolet |
| ε | Extinction coefficient |
| $\lambda_{max}$ | Wavelength of absorption maximum |
| RP-18 | reversed phase octadecyl-modified silica gel |
| DMTr | Dimethoxytrityl |
| TBDMS | Tertiary butyl-dimethylsilyl |
| CEP | O-Cyanoethyl-N,N-diisopropylphosphoramidite |
| HEPES | 4-(2-Hydroxyethyl)-1-piperazinoethanesulfonic acid |
| HPLC | high performance liquid chromatography |
| MW | Molecular weight |
| m/z | Mass/charge ratio |
| NHS | N-Hydroxysuccinimide |
| Bz | Benzoyl |
| iBu | Isobutyryl |
| tert | tertiary |

LITERATURE

1. Urata, H.; Fujimori, M.; Aono, C.; Yamakawa, T.; Harada, E.; Akagi, M., Regio- and diastereo-selectivity of montmorillonite-catalyzed oligomerization of racemic adenosine 5'-phosphorimidazolide. *Nucleosides Nucleotides Nucleic Acids* 2008, 27 (4), 421-30.
2. Mehne, F. M.; Schroder-Tittmann, K.; Eijlander, R. T.; Herzberg, C.; Hewitt, L.; Kaever, V.; Lewis, R. J.; Kuipers, O. P.; Tittmann, K.; Stulke, J., Control of the diadenylate cyclase CdaS in *Bacillus subtilis*: an autoinhibitory domain limits cyclic di-AMP production. *J Biol Chem* 2014, 289 (30), 21098-107.
3. Li, L.; Yin, Q.; Kuss, P.; Maliga, Z.; Millan, J. L.; Wu, H.; Mitchison, T. J., Hydrolysis of 2'3'-cGAMP by ENPP1 and design of nonhydrolyzable analogs. *Nat Chem Biol* 2014, 10 (12), 1043-8.

4. Gaffney, B. L.; Veliath, E.; Zhao, J.; Jones, R. A., One-flask syntheses of c-di-GMP and the [Rp,Rp] and [Rp,Sp] thiophosphate analogues. *Org Lett* 2010, 12 (14), 3269-71.
5. Gao, P.; Ascano, M.; Wu, Y.; Barchet, W.; Gaffney, B. L.; Zillinger, T.; Serganov, A. A.; Liu, Y.; Jones, R. A.; Hartmann, G.; Tuschl, T.; Patel, D. J., Cyclic [G(2',5')pA(3',5')p] is the metazoan second messenger produced by DNA-activated cyclic GMP-AMP synthase. *Cell* 2013, 153 (5), 1094-107.
6. Parsch, J.; Engels, J. W., C-F . . . H-C hydrogen bonds in ribonucleic acids. *J Am Chem Soc* 2002, 124 (20), 5664-72.
7. Krass, J. D.; Jastorff, B.; Genieser, H. G., Determination of lipophilicity by gradient elution high-performance liquid chromatography. *Anal Chem* 1997, 69 (13), 2575-81.
8. Margolin A. L.; Borcherding D. R.; Wolf-Kugel D.; Margolin N., AMP deaminase as a novel practical catalyst in the synthesis of 6-oxopurine ribosides and their analogs. *J. Org. Chem.* 1994, 59(24), 7214-7218.

The invention claimed is:

1. A compound having a structure in accordance with Formula (I):

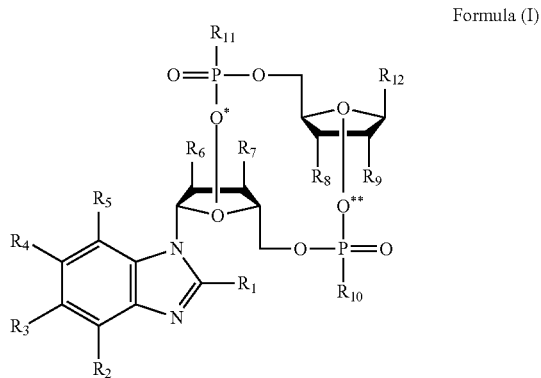

Formula (I)

wherein one of $R_6$ and $R_7$ is a bond to the oxygen marked with one asterisk (*) and one of $R_8$ and $R_9$ is a bond to the oxygen marked with two asterisks (**);

$R_1$ is:
H, Cl, Br, I, F, $N_3$, $NO_2$, OH, SH, $NH_2$, $CF_3$, alkyl, aryl, aralkyl, acyl, aracyl, S-alkyl, S-aryl, S-aralkyl, S-acyl, S-aracyl, S(O)-alkyl, S(O)-aryl, S(O)-aralkyl, S(O)-acyl, S(O)-aracyl, $S(O)_2$-alkyl, $S(O)_2$-aryl, $S(O)_2$-aralkyl, $S(O)_2$-acyl, $S(O)_2$-aracyl, $NR_{13}R_{14}$ wherein $R_{13}$ and $R_{14}$ can independently be H, alkyl, aryl or aralkyl, 2-furyl, 3-furyl, 2-bromo-5-furyl, (2-furyl)thio, (3-(2-methyl)furyl)thio, (3-furyl)thio, 2-thienyl, 3-thienyl, (5-(1-methyl)tetrazolyl)thio, 2-(N-(7-nitrobenz-2-oxa-1,3-diazol-4-yl)amino)ethylthio, (4-bromo-2,3-dioxobutyl)thio, [2-[(fluoresceinylthioureido)amino]ethyl]thio, (7-(4-methyl)coumarinyl)thio, (4-(7-methoxy)coumarinyl)thio, (2-naphtyl)thio, 4-pyridyl, (4-pyridyl)thio, 2-pyridylthio, 5-amino-3-oxopentylamino, 8-amino-3,6-dioxaoctylamino, 19-amino-4,7,10,13,16-pentaoxanonadecylamino, 17-amino-9-aza-heptadecylamino, 4-(N-methylanthranoyl)aminobutylamino, dimethylamino, diethylamino, 4-morpholino, 1-piperidino or 1-piperazino or the residue $R_1$ is as defined in the following Groups 1 or 2:

Group 1:

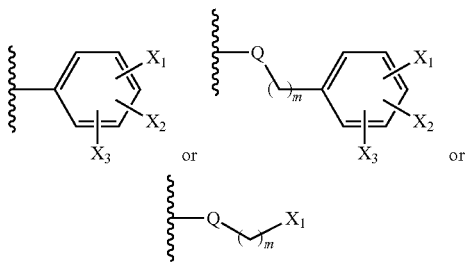

wherein
m=0-6;
Q=S, S(O), $S(O)_2$, O, NH, $CH_2$ or C(O);
$X_1$, $X_2$ and $X_3$ are independently of each other H, OH, $NH_2$, $N_3$, SH, CN, $NO_2$, F, Cl, Br, I, $(CH_2)_nCH_3$ (with n=0-5), i-Pr, t-Bu, (with n=0-5), $(CH_2)_nCH=CH_2$ (with n=0-5), $CH_2OH$, $(CH_2)nOCH_3$ (with n=1-2), $CH_2N(CH_3)_2$, $O(CH_2)_nCH_3$ (with n=0-5), Oi-Pr, OCy, OCyp, OBn, $OC(O)CH_3$, OC(O)Ph, $OCF_3$, $N(CH_3)_2$, $NH(CH_2)_nCH_3$ (with n=0-5), NHC(O)t-Bu, NHC(O)Ph, NHC(O)Ot-Bu, $NHC(O)CH_3$, $NHC(O)CH_2N_3$, $B(OH)_2$, $CF_3$, C(O)OH, $C(O)OCH_3$, C(O)Oi-Pr, C(O)Ot-Bu, C(O)OPh, C(O)OBn, $C(O)NH_2$, $C(O)N(CH_3)_2$, C(O)NHPh, C(O)NHBn, $C(O)CF_3$, $CH_2C(O)OH$, $CH_2C(O)OCH_3$, $CH_2C(O)Oi$-Pr, $CH_2C(O)Ot$-Bu, $CH_2C(O)OBn$, $S(CH_2)_nCH_3$ (with n=0-5), $S(CH_2)_nOEt$ (with n=1-4), SBn, $SO_2CH_3$, $SO_2CF_3$,

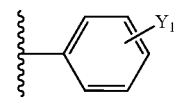

(with $Y_1$=H, SH, CN, Ph, F, $CH_3$, $OCH_3$, $SCH_3$, 4-thiophenyl, $NO_2$, pentyl),

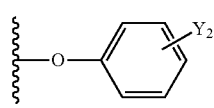

(with $Y_2$=H, SH, F),

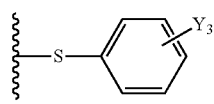

(with $Y_3$=H, SH),

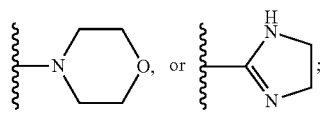

Group 2:

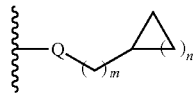

wherein
m=0-6;
n=1-6;
Q=S, S(O), S(O)$_2$, O or NH;
R$_2$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_3$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_4$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_5$ is H, F, Cl, Br, NH$_2$, NO$_2$, CN, CH$_3$, OH, CF$_3$, SH, O—CH$_3$, OCF$_3$, N(CH$_3$)$_2$, S—CH$_3$ or C(O)OH;
R$_6$ or R$_7$ is H, OH, NH$_2$, F, O—CH$_3$, S—CH$_3$, OCH$_2$C≡C, OCH$_2$CH═CH$_2$, O-acyl, O-aracyl, O—C(O)NH—(CH$_2$)$_6$NH$_2$ or O— (N'-methylanthraniloyl), while the other residue R$_6$ or R$_7$ represents the connection with the oxygen marked with one asterisk (*);
R$_8$ or R$_9$ is H, OH, NH$_2$, F, O—CH$_3$, S—CH$_3$, OCH$_2$C≡C, OCH$_2$CH═CH$_2$, O-acyl, O-aracyl, O—C(O)NH—(CH$_2$)$_6$NH$_2$ or, O— (N'-methylanthraniloyl), while the other residue R$_8$ or R$_9$ represents the connection with the oxygen marked with two asterisks (**);
R$_{10}$ is OH, SH, borano (BH$_3$), S-PAS, O-PAS, S-BAS or O-BAS,
 wherein PAS is a photo-activatable protecting group, and
 wherein BAS is a bio-activatable protecting group selected from methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, and 4-benzoyloxybenzyl;
R$_{11}$ is OH, SH, borano (BH$_3$), S-PAS, O-PAS, S-BAS or O-BAS,
 wherein PAS is a photo-activatable protecting group, and wherein BAS is a bio-activatable protecting group selected from methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, and 4-benzoyloxybenzyl, and
R$_{12}$ is

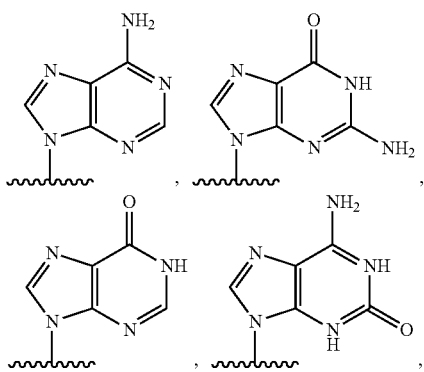

-continued

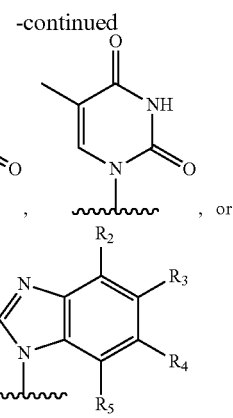

wherein R$_1$ up to R$_5$ are defined as described above.

2. The compound according to claim 1, wherein R$_{12}$ has the following structure:

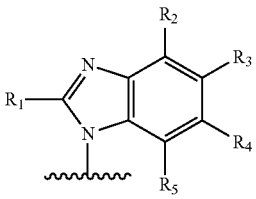

wherein one, two, three, four or all residues R$_1$, R$_2$, R$_3$, R$_4$ and R$_5$ are identical or different compared to the other residue with the same index.

3. The compound according to claim 1, wherein R$_{10}$ and/or R$_{11}$ is SH; or R$_{10}$ and/or R$_{11}$ is BH$_3$; or R$_{10}$ is SH and R$_{11}$ is BH$_3$; or R$_{10}$ is BH$_3$ and R$_{11}$ is SH.

4. The compound according to claim 1, wherein the connections via O* and O** are realized by R$_7$ and R$_8$ leading to compounds assigned as 3', 5'-3', 5'-connected.

5. The compound according to claim 1, wherein the connections via O* and O** are realized by R$_6$ and R$_8$ leading to compounds assigned as 2', 5'-3', 5'-connected.

6. The compound according to claim 1, wherein R$_3$ and R$_4$ each are Cl; or each R$_1$, R$_3$ and R$_4$ are Cl; or R$_1$ is CF$_3$ and R$_3$ and R$_4$ each are Cl.

7. The compound according to claim 1, wherein R$_6$ or R$_7$ and R$_8$ or R$_9$ each are OH; or R$_6$ or R$_7$ is F and R$_8$ or R$_9$ is OH; or R$_6$ or R$_7$ is OH and R$_8$ or R$_9$ is F; or R$_6$ or R$_7$ and R$_8$ or R$_9$ each are F.

8. The compound according to claim 1, wherein the structure in accordance with Formula (I) is chosen from:
 (1) cyclic (benzimidazole riboside-(3'→5')-monophosphate-benzimidazole riboside-(3'→5')-monophosphate);
 (2) cyclic (benzimidazole riboside-(2'→5')-monophosphate-benzimidazole riboside-(3'→5')-monophosphate);
 (3) cyclic (benzimidazole riboside-(2'→5')-monophosphate-benzimidazole riboside-(2'→5')-monophosphate);
 (4) cyclic (benzimidazole riboside-(3'→5')-monophosphorothioate-benzimidazole riboside-(3'→5')-monophosphorothioate);
 (5) cyclic (benzimidazole riboside-(2'→5')-monophosphorothioate-benzimidazole riboside-(3'→5')-monophosphorothioate);

(6) cyclic (benzimidazole riboside-(2'→5')-monophosphorothioate-benzimidazole riboside-(2'→5')-monophosphorothioate);
(7) cyclic (5,6-dichlorobenzimidazole riboside-(3'→5')-monophosphate-5,6-dichlorobenzimi-dazole riboside-(3'→5')-monophosphate);
(8) cyclic (5,6-dichlorobenzimidazole riboside-(2'→5')-monophosphate-5,6-dichlorobenzimi-dazole riboside-(3'→5')-monophosphate);
(9) cyclic (5,6-dichlorobenzimidazole riboside-(2'→5')-monophosphate-5,6-dichlorobenzimi-dazole riboside-(2'→5')-monophosphate);
(10) cyclic (5,6-dichlorobenzimidazole riboside-(3'→5')-monophosphorothioate-5,6-dichloro-benzimidazole riboside-(3'→5')-monophosphorothioate);
(11) cyclic (5,6-dichlorobenzimidazole riboside-(2'→5')-monophosphorothioate-5,6-dichloro-benzimidazole riboside-(3'→5')-monophosphorothioate);
(12) cyclic (5,6-dichlorobenzimidazole riboside-(2'→5')-monophosphorothioate-5,6-dichloro-benzimidazole riboside-(2'→5')-monophosphorothioate);
(13) cyclic (2,5,6-trichlorobenzimidazole riboside-(3'→5')-monophosphate-2,5,6-trichlorobenzimidazole riboside-(3'→5')-monophosphate);
(14) cyclic (2,5,6-trichlorobenzimidazole riboside-(2'→5')-monophosphate-2,5,6-trichloro-benzimidazole riboside-(3'→5')-monophosphate);
(15) cyclic (2,5,6-trichlorobenzimidazole riboside-(2'→5')-monophosphate-2,5,6-trichloro-benzimidazole riboside-(2'→5')-monophosphate);
(16) cyclic (2,5,6-trichlorobenzimidazole riboside-(3'→5')-monophosphorothioate-2,5,6-tri-chlorobenzimidazole riboside-(3'→5')-monophosphorothioate);
(17) cyclic (2,5,6-trichlorobenzimidazole riboside-(2'→5')-monophosphorothioate-2,5,6-tri-chlorobenzimidazole riboside-(3'→5')-monophosphorothioate);
(18) cyclic (2,5,6-trichlorobenzimidazole riboside-(2'→5')-monophosphorothioate-2,5,6-tri-chlorobenzimidazole riboside-(2'→5')-monophosphorothioate);
(19) cyclic (guanosine-(3'→5')-monophosphate-benzimidazole riboside-(3'→5')-mono-phosphate);
(20) cyclic (guanosine-(2'→5')-monophosphate-benzimidazole riboside-(3'→5')-mono-phosphate);
(21) cyclic (guanosine-(2'→5')-monophosphate-benzimidazole riboside-(2'→5')-mono-phosphate);
(22) cyclic (guanosine-(3'→5')-monophosphorothioate-benzimidazole riboside-(3'→5')-monophosphorothioate);
(23) cyclic (guanosine-(2'→5')-monophosphorothioate-benzimidazole riboside-(3'→5')-monophosphorothioate);
(24) cyclic (guanosine-(2'→5')-monophosphorothioate-benzimidazole riboside-(2' →5')-monophosphorothioate);
(25) cyclic (guanosine-(3'→5')-monophosphate-5,6-dichlorobenzimidazole riboside-(3'→5')-monophosphate);
(26) cyclic (guanosine-(2'→5')-monophosphate-5,6-dichlorobenzimidazole riboside-(3'→5')-monophosphate);
(27) cyclic (guanosine-(2'→5')-monophosphate-5,6-dichlorobenzimidazole riboside-(2'→5')-monophosphate);
(28) cyclic (guanosine-(3'→5')-monophosphorothioate-5,6-dichlorobenzimidazole riboside-(3'→5')-monophosphorothioate);
(29) cyclic (guanosine-(2'→5')-monophosphorothioate-5,6-dichlorobenzimidazole riboside-(3'→5')-monophosphorothioate);
(30) cyclic (guanosine-(2'→5')-monophosphorothioate-5,6-dichlorobenzimidazole riboside-(2'→5')-monophosphorothioate);
(31) cyclic (guanosine-(3'→5')-monophosphate-2,5,6-trichlorobenzimidazole riboside-(3'→5')-monophosphate);
(32) cyclic (guanosine-(2'→5')-monophosphate-2,5,6-trichlorobenzimidazole riboside-(3'→5')-monophosphate);
(33) cyclic (guanosine-(2'→5')-monophosphate-2,5,6-trichlorobenzimidazole riboside-(2'→5')-monophosphate);
(34) cyclic (guanosine-(3'→5')-monophosphorothioate-2,5,6-trichlorobenzimidazole riboside-(3'→5')-monophosphorothioate);
(35) cyclic (guanosine-(2'→5')-monophosphorothioate-2,5,6-trichlorobenzimidazole riboside-(3'→5')-monophosphorothioate);
(36) cyclic (guanosine-(2'→5')-monophosphorothioate-2,5,6-trichlorobenzimidazole riboside-(2'→5')-monophosphorothioate);
(37) cyclic (adenosine-(3'→5')-monophosphate-benzimidazole riboside-(3'→5')-mono-phosphate);
(38) cyclic (adenosine-(2'→5')-monophosphate-benzimidazole riboside-(3'→5')-mono-phosphate);
(39) cyclic (adenosine-(2'→5')-monophosphate-benzimidazole riboside-(2'→5')-mono-phosphate);
(40) cyclic (adenosine-(3'→5')-monophosphorothioate-benzimidazole riboside-(3'→5')-monophosphorothioate);
(41) cyclic (adenosine-(2'→5')-monophosphorothioate-benzimidazole riboside-(3'→5')-monophosphorothioate);
(42) cyclic (adenosine-(2'→5')-monophosphorothioate-benzimidazole riboside-(2'→5')-mono-phosphorothioate);
(43) cyclic (adenosine-(3'→5')-monophosphate-5,6-dichlorobenzimidazole riboside-(3'→5')-monophosphate);
(44) cyclic (adenosine-(2'→5')-monophosphate-5,6-dichlorobenzimidazole riboside-(3'→5')-monophosphate);
(45) cyclic (adenosine-(2'→5')-monophosphate-5,6-dichlorobenzimidazole riboside-(2'→5')-monophosphate);
(46) cyclic (adenosine-(3'→5')-monophosphorothioate-5,6-dichlorobenzimidazole riboside-(3'→5')-monophosphorothioate);
(47) cyclic (adenosine-(2'→5')-monophosphorothioate-5,6-dichlorobenzimidazole riboside-(3'→5')-monophosphorothioate);
(48) cyclic (adenosine-(2'→5')-monophosphorothioate-5,6-dichlorobenzimidazole riboside-(2'→5')-monophosphorothioate);
(49) cyclic (adenosine-(3'→5')-monophosphate-2,5,6-trichlorobenzimidazole riboside-(3'→5')-monophosphate);
(50) cyclic (adenosine-(2'→5')-monophosphate-2,5,6-trichlorobenzimidazole riboside-(3'→5')-monophosphate);
(51) cyclic (adenosine-(2'→5')-monophosphate-2,5,6-trichlorobenzimidazole riboside-(2'→5')-monophosphate);

(52) cyclic (adenosine-(3'→5')-monophosphorothioate-2,5,6-trichlorobenzimidazole riboside-(3'→5')-monophosphorothioate);
(53) cyclic (adenosine-(2'→5')-monophosphorothioate-2,5,6-trichlorobenzimidazole riboside-(3'→5')-monophosphorothioate);
(54) cyclic (adenosine-(2'→5')-monophosphorothioate-2,5,6-trichlorobenzimidazole riboside-(2'→5')-monophosphorothioate);
(55) cyclic (inosine-(3'→5')-monophosphate-benzimidazole riboside-(3'→5')-mono-phosphate)
(56) cyclic (inosine-(2'→5')-monophosphate-benzimidazole riboside-(3'→5')-mono-phosphate);
(57) cyclic (inosine-(2'→5')-monophosphate-benzimidazole riboside-(2'→5')-mono-phosphate);
(58) Cyclic (inosine-(3'→5')-monophosphorothioate-benzimidazole riboside-(3'→5')-mono-phosphorothioate);
(59) cyclic (inosine-(2'→5')-monophosphorothioate-benzimidazole riboside-(3'→5')-mono-phosphorothioate);
(60) cyclic (inosine-(2'→5')-monophosphorothioate-benzimidazole riboside-(2'→5')-mono-phosphorothioate);
(61) cyclic (inosine-(3'→5')-monophosphate-5,6-dichlorobenzimidazole riboside-(3'→5')-monophosphate);
(62) cyclic (inosine-(2'→5')-monophosphate-5,6-dichlorobenzimidazole riboside-(3'→5')-monophosphate);
(63) cyclic (inosine-(2'→5')-monophosphate-5,6-dichlorobenzimidazole riboside-(2'→5')-monophosphate);
(64) cyclic (inosine-(3'→5')-monophosphorothioate-5,6-dichlorobenzimidazole riboside-(3'→5')-monophosphorothioate);
(65) cyclic (inosine-(2'→5')-monophosphorothioate-5,6-dichlorobenzimidazole riboside-(3'→5')-monophosphorothioate);
(66) cyclic (inosine-(2'→5')-monophosphorothioate-5,6-dichlorobenzimidazole riboside-(2'→5')-monophosphorothioate);
(67) cyclic (inosine-(3'→5')-monophosphate-2,5,6-trichlorobenzimidazole riboside-(3'→5')-monophosphate);
(68) cyclic (inosine-(2'→5')-monophosphate-2,5,6-trichlorobenzimidazole riboside-(3'→5')-monophosphate);
(69) cyclic (inosine-(2'→5')-monophosphate-2,5,6-trichlorobenzimidazole riboside-(2'→5')-monophosphate);
(70) cyclic (inosine-(3'→5')-monophosphorothioate-2,5,6-trichlorobenzimidazole riboside-(3'→5')-monophosphorothioate);
(71) cyclic (inosine-(2'→5')-monophosphorothioate-2,5,6-trichlorobenzimidazole riboside-(3'→5')-monophosphorothioate);
(72) cyclic (inosine-(2'→5')-monophosphorothioate-2,5,6-trichlorobenzimidazole riboside-(2'→5')-monophosphorothioate);
(73) cyclic (2'-fluoro-2'-deoxyguanosine-(3'→5')-monophosphate-benzimidazole riboside-(3'→5')-monophosphate);
(74) cyclic (2'-fluoro-2'-deoxyguanosine-(3'→5')-monophosphorothioate-benzimidazole riboside-(3'→5')-monophosphorothioate);
(75) cyclic (2'-fluoro-2'-deoxyguanosine-(3'→5')-monophosphate-5,6-dichlorobenzimidazole riboside-(3'→5')-monophosphate);
(76) cyclic (2'-fluoro-2'-deoxyguanosine-(3'→5')-monophosphate-5,6-dichlorobenzimidazole riboside-(3'→5')-monophosphate);
(77) cyclic (2'-fluoro-2'-deoxyguanosine-(3'→5')-monophosphate-2,5,6-trichlorobenzimida-zole riboside-(3'→5')-monophosphate);
(78) cyclic (2'-fluoro-2'-deoxyguanosine-(3'→5')-monophosphorothioate-5,6-dichlorobenzi-midazole riboside-(3'→5')-monophosphorothioate);
(79) cyclic (2'-fluoro-2'-deoxyadenosine-(3'→5')-monophosphate-benzimidazole riboside-(3'→5')-monophosphate);
(80) cyclic (2'-fluoro-2'-deoxyadenosine-(3'→5')-monophosphorothioate-benzimidazole riboside-(3'→5')-monophosphorothioate);
(81) cyclic (2'-fluoro-2'-deoxyadenosine-(3'→5')-monophosphate-5,6-dichlorobenzimidazole riboside-(3'→5')-monophosphate);
(82) cyclic (2'-fluoro-2'-deoxyadenosine-(3'→5')-monophosphorothioate-5,6-dichloroben-zimidazole riboside-(3'→5')-monophosphorothioate);
(83) cyclic (2'-fluoro-2'-deoxyadenosine-(3'→5')-monophosphate-2,5,6-trichlorobenz-imidazole riboside-(3'→5')-monophosphate);
(84) cyclic (2'-fluoro-2'-deoxyadenosine-(3'→5')-monophosphorothioate-2,5,6-trichlorobenz-imidazole riboside-(3'→5')-monophosphorothioate);
(85) cyclic (2'-fluoro-2'-deoxyinosine-(3'→5')-monophosphate-benzimidazole riboside-(3'→5')-monophosphate);
(86) cyclic (2'-fluoro-2'-deoxyinosine-(3'→5')-monophosphorothioate-benzimidazole riboside-(3'→5')-monophosphorothioate);
(87) cyclic (2'-fluoro-2'-deoxyinosine-(3'→5')-monophosphate-5,6-dichlorobenzimidazole riboside-(3'→5')-monophosphate);
(88) cyclic (2'-fluoro-2'-deoxyinosine-(3'→5')-monophosphorothioate-5,6-dichlorobenzimidazole riboside-(3'→5')-monophosphorothioate);
(89) cyclic (2'-fluoro-2'-deoxyinosine-(3'→5')-monophosphate-2,5,6-trichlorobenzimidazole riboside-(3'→5')-monophosphate);
(90) cyclic (2'-fluoro-2'-deoxyinosine-(3'→5')-monophosphorothioate-2,5,6-trichlorobenz-imidazole riboside-(3'→5')-monophosphorothioate);
(91) cyclic (guanosine-(3'→5')-monophosphate-benzimidazole riboside-(2'→5')-mono-phosphate);
(92) cyclic (guanosine-(3'→5')-monophosphorothioate-benzimidazole riboside-(2'→5')-monophosphorothioate);
(93) cyclic (guanosine-(3'→5')-monophosphate-5,6-dichlorobenzimidazole riboside-(2'→5')-monophosphate);
(94) cyclic (guanosine-(3'→5')-monophosphorothioate-5,6-dichlorobenzimidazole riboside-(2'→5')-monophosphorothioate);
(95) cyclic (guanosine-(3'→5')-monophosphate-2,5,6-trichlorobenzimidazole riboside-(2'→5')-monophosphate);
(96) cyclic (guanosine-(3'→5')-monophosphorothioate-2,5,6-trichlorobenzimidazole riboside-(2'→5')-monophosphorothioate);
(97) cyclic (adenosine-(3'→5')-monophosphate-benzimidazole riboside-(2'→5')-mono-phosphate);
(98) cyclic (adenosine-(3'→5')-monophosphorothioate-benzimidazole riboside-(2'→5')-monophosphorothioate);
(99) cyclic (adenosine-(3'→5')-monophosphate-5,6-dichlorobenzimidazole riboside-(2'→5')-monophosphate);

(100) cyclic (adenosine-(3'→5')-monophosphorothioate-5,6-dichlorobenzimidazole riboside-(2'→5')-monophosphorothioate);
(101) cyclic (adenosine-(3'→5')-monophosphate-2,5,6-trichlorobenzimidazole riboside-(2'→5')-monophosphate);
(102) cyclic (adenosine-(3'→5')-monophosphorothioate-2,5,6-trichlorobenzimidazole riboside-(2'→5')-monophosphorothioate);
(103) cyclic (inosine-(3'→5')-monophosphate-benzimidazole riboside-(2'→5')-monophosphate);
(104) cyclic (inosine-(3'→5')-monophosphorothioate-benzimidazole riboside-(2'→5')-monophosphorothioate);
(105) cyclic (inosine-(3'→5')-monophosphate-5,6-dichlorobenzimidazole riboside-(2'→5')-monophosphate);
(106) cyclic (inosine-(3'→5')-monophosphorothioate-5,6-dichlorobenzimidazole riboside-(2'→5')-monophosphorothioate);
(107) cyclic (inosine-(3'→5')-monophosphate-2,5,6-trichlorobenzimidazole riboside-(2'→5')-monophosphate);
(108) cyclic (inosine-(3'→5')-monophosphorothioate-2,5,6-trichlorobenzimidazole riboside-(2'→5')-monophosphorothioate);
(109) cyclic (2'-fluoro-2'-deoxyguanosine-(3'→5')-monophosphate-benzimidazole riboside-(2'→5')-monophosphate);
(110) cyclic (2'-fluoro-2'-deoxyguanosine-(3'→5')-monophosphorothioate-benzimidazole riboside-(2'→5')-monophosphorothioate);
(111) cyclic (2'-fluoro-2'-deoxyguanosine-(3'→5')-monophosphate-5,6-dichlorobenzimidazole riboside-(2'→5')-monophosphate);
(112) cyclic (2'-fluoro-2'-deoxyguanosine-(3'→5')-monophosphate-5,6-dichlorobenzimidazole riboside-(2'→5')-monophosphate);
(113) cyclic (2'-fluoro-2'-deoxyguanosine-(3'→5')-monophosphate-2,5,6-trichlorobenzimidazole riboside-(2'→5')-monophosphate);
(114) cyclic (2'-fluoro-2'-deoxyguanosine-(3'→5')-monophosphorothioate-5,6-dichlorobenzimidazole riboside-(2'→5')-monophosphorothioate);
(115) cyclic (2'-fluoro-2'-deoxyadenosine-(3'→5')-monophosphate-benzimidazole riboside-(2'→5')-monophosphate);
(116) cyclic (2'-fluoro-2'-deoxyadenosine-(3'→5')-monophosphorothioate-benzimidazole riboside-(2'→5')-monophosphorothioate);
(117) cyclic (2'-fluoro-2'-deoxyadenosine-(3'→5')-monophosphate-5,6-dichlorobenzimidazole riboside-(2'→5')-monophosphate);
(118) cyclic (2'-fluoro-2'-deoxyadenosine-(3'→5')-monophosphorothioate-5,6-dichlorobenzimidazole riboside-(2'→5')-monophosphorothioate);
(119) cyclic (2'-fluoro-2'-deoxyadenosine-(3'→5')-monophosphate-2,5,6-trichlorobenzimidazole riboside-(2'→5')-monophosphate);
(120) cyclic (2'-fluoro-2'-deoxyadenosine-(3'→5')-monophosphorothioate-2,5,6-trichlorobenzimidazole riboside-(2'→5')-monophosphorothioate);
(121) cyclic (2'-fluoro-2'-deoxyinosine-(3'→5')-monophosphate-benzimidazole riboside-(2'→5')-monophosphate);
(122) cyclic (2'-fluoro-2'-deoxyinosine-(3'→5')-monophosphorothioate-benzimidazole riboside-(2'→5')-monophosphorothioate);
(123) cyclic (2'-fluoro-2'-deoxyinosine-(3'→5')-monophosphate-5,6-dichlorobenzimidazole riboside-(2'→5')-monophosphate);
(124) cyclic (2'-fluoro-2'-deoxyinosine-(3'→5')-monophosphorothioate-5,6-dichlorobenzimidazole riboside-(2'→5')-monophosphorothioate);
(125) cyclic (2'-fluoro-2'-deoxyinosine-(3'→5')-monophosphate-2,5,6-trichlorobenzimidazole riboside-(2'→5')-monophosphate);
(126) cyclic (2'-fluoro-2'-deoxyinosine-(3'→5')-monophosphorothioate-2,5,6-trichlorobenzimidazole riboside-(2'→5')-monophosphorothioate);
(127) cyclic (adenosine-(3'→5')-monophosphate-5,6-dimethylbenzimidazole riboside-(2'→5')-monophosphate);
(128) cyclic (adenosine-(3'→5')-monoboranophosphate-benzimidazole riboside-(3'→5')-monophosphate);
(129) cyclic (guanosine-(2'→5')-monoboranophosphate-benzimidazole riboside-(3'→5')-monophosphate);
(130) cyclic (guanosine-(2'→5')-monoboranophosphate-benzimidazole riboside-(3'→5')-monophosphorothioate);
(131) cyclic (adenosine-(2'→5')-monophosphorothioate-benzimidazole riboside-(3'→5')-monoboranophosphate);
(132) cyclic (adenosine-(3'→5')-monophosphate-benzimidazole riboside-(2'→5')-monophosphorothioate); and
(133) cyclic (adenosine-(2'→5')-monoboranophosphate-benzimidazole riboside-(2' →5')-monophosphate).

9. The compound according to claim 1 in pharmacologically acceptable form for the treatment of diseases chosen from cancer, infectious diseases of bacterial or viral origin, acute organ transplant rejection, diabetes mellitus type I, rheumatoid arthritis, psoriasis, Crohn's disease, restenosis, allergic asthma and other diseases, which can be improved or healed by activation of the STING signalling pathway.

10. The compound of claim 1, wherein the PAS of $R_{10}$ is o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged), or 6,7-bis(carboxymethoxy)coumarin-4-yl)methyl (BCMCM-caged).

11. The compound of claim 1, wherein the BAS of $R_{10}$ is a methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, or 4-benzoyloxybenzyl.

12. The compound of claim 1, wherein the PAS of $R_{11}$ is o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged), or 6,7-bis(carboxymethoxy)coumarin-4-yl)methyl (BCMCM-caged).

13. The compound of claim 1, wherein the BAS of $R_{11}$ is a methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, or 4-benzoyloxybenzyl.

14. The compound of claim 1, wherein
the PAS of $R_{10}$ is o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged), or 6,7-bis(carboxymethoxy)coumarin-4-yl)methyl (BCMCM-caged);

the BAS of $R_{10}$ is a methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, or 4-benzoyloxybenzyl;

the PAS of $R_{11}$ is o-nitro-benzyl, 1-(o-nitrophenyl)-ethylidene, 4,5-dimethoxy-2-nitro-benzyl, 7-dimethylamino-coumarin-4-yl (DMACM-caged), 7-diethylamino-coumarin-4-yl (DEACM-caged), or 6,7-bis(carboxymethoxy)coumarin-4-yl)methyl (BCMCM-caged); and the BAS of $R_{11}$ is a methyl, acetoxymethyl, pivaloyloxymethyl, methoxymethyl, propionyloxymethyl, butyryloxymethyl, cyanoethyl, phenyl, benzyl, 4-acetoxybenzyl, 4-pivaloyloxybenzyl, 4-isobutyryloxybenzyl, 4-octanoyloxybenzyl, or 4-benzoyloxybenzyl.

15. A method for the chemoenzymatic production of a compound according to claim 1, wherein the structure in accordance with Formula (I) has a structural unit $[N_1(2',5')pN_2(3',5')p]$ or $c[N_1(3',5')pN_2(3',5')p]$ by transglycosylation of c-diAMP, c-diGMP, 2',3'-cGAMP or 3',3'-cGAMP with purine nucleoside phosphorylase (PNPase).

16. A method for the chemoenzymatic production of a compound according to claim 1, wherein the structure in accordance with Formula (I) has a structural unit $c[N_1(2',5')pN_2(3',5')p]$, $c[N_1(2',5')pS-N_2(3',5')p]$, $c[N_1(2',5')pS-N_2(3',5')pS]$, $c[N_1(2',5')pB-N_2(3',5')p]$, $c[N_1(2',5')pB-N_2(3',5')pB]$, $c[N_1(2',5')pB-N_2(3',5')pS]$ or $c[N_1(2',5')pS-N_2(3',5')pB]$ by dimerisation and cyclisation of 5'-O-triphosphates, 5'-O-(1-thiotriphosphates) or 5'-O-(1-boranotriphosphates) with a cGAMP synthase (cGAS).

17. A method for the chemoenzymatic production of a compound according to claim 1, wherein the structure in accordance with Formula (I) has a structural unit $c[N_1(3',5')pN_2(3',5')p]$, $c[N_1(3',5')pB-N_2(3',5')p]$, $c[N_1(3',5')p-N_2(3',5')pB]$, or $c[N_1(3',5')pB-N_2(3',5')pB]$, wherein alternatively the benzimidazole residue in $N_1$ can be replaced by a possibly substituted purine base, via dimerization and cyclisation of 5'-O-triphosphates or 5'-O-(1-boranotriphosphates) with an Enzyme DNA integrity scanning protein (DisA) from *Bacillus subtilis*.

* * * * *